US012611392B2

(12) United States Patent
Boulghobra et al.

(10) Patent No.: US 12,611,392 B2
(45) Date of Patent: Apr. 28, 2026

(54) MITOCHONDRIA-TARGETING ANTIOXIDANTS

(71) Applicants: GIVAUDAN SA, Vernier (CH); AVIGNON UNIVERSITÉ, Avignon (FR); L'UNIVERSITÉ DE MONTPELLIER, Montpellier (FR); CENTRE NATIONAL DE LA RECHERCHE SCIENTIFIQUE, Paris (FR); L'INSTITUT NATIONAL DE LA SANTE ET DE LA RECHERCHE MEDICALE, Paris (FR)

(72) Inventors: Doria Boulghobra, Avignon (FR); Michael Laguerre, Le Pontet (FR); Mathieu Tenon, Malemort du Comtat (FR); Jérémy Fauconnier, Montpellier (FR); Simona Birtic, Cavaillon (FR); Pascale Elizabeth Renée Fança-Berthon, Le Thor (FR); Cyril Reboul, Avignon (FR); Olivier Cazorla, Montpellier (FR)

(73) Assignees: Givaudan SA, Vernier (CH); Avignon Universite, Avignon (FR); L 'Universite De Montpellier, Montpellier (FR); Centre National De La Recherche Scientifique, Paris (FR); L 'Institut National De La Sante Et De La Recherche Medicale, Paris (FR)

( * ) Notice: Subject to any disclaimer, the term of this patent is extended or adjusted under 35 U.S.C. 154(b) by 1029 days.

(21) Appl. No.: 17/774,684

(22) PCT Filed: Nov. 6, 2020

(86) PCT No.: PCT/EP2020/081308
§ 371 (c)(1),
(2) Date: May 5, 2022

(87) PCT Pub. No.: WO2021/089790
PCT Pub. Date: May 14, 2021

(65) Prior Publication Data

US 2022/0370394 A1 Nov. 24, 2022

(30) Foreign Application Priority Data

Nov. 7, 2019 (GB) ..................................... 1916219

(51) Int. Cl.

| | |
|---|---|
| ***A61K 31/216*** | (2006.01) |
| ***A23L 33/105*** | (2016.01) |
| ***A61K 36/31*** | (2006.01) |
| ***A61P 21/06*** | (2006.01) |

(52) U.S. Cl.
CPC .......... *A61K 31/216* (2013.01); *A23L 33/105* (2016.08); *A61K 36/31* (2013.01); *A61P 21/06* (2018.01)

(58) Field of Classification Search
None
See application file for complete search history.

(56) References Cited

FOREIGN PATENT DOCUMENTS

| | | | |
|---|---|---|---|
| CN | 1069724 | A | 3/1993 |
| CN | 103804207 | A | 5/2014 |
| CN | 109044900 | A | 12/2018 |
| EP | 1437117 | A1 | 7/2004 |

OTHER PUBLICATIONS

Silambarasan et al. "Sinapic acid protects heart against ischemia/reperfusion injury and H9c2 cardiomyoblast cells against oxidative stress," Biochemical and Biophysical Research Communications 456 (2015) 853-859; (Year: 2015).*
Lateef et al. "Langendorff's isolated perfused rat heart technique: a review," International Journal of Basic & Clinical Pharmacology, Dec. 2015, vol. 4, Issue 6, p. 1314; (Year: 2015).*
Chen "Sinapic Acid and Its Derivatives as Medicine in Oxidative Stress-Induced Diseases and Aging," Oxidative Medicine and Cellular Longevity vol. 2016; (Year: 2016).*
Vuorela et al. "Preclinical Evaluation of Rapeseed, Raspberry, and Pine Bark Phenolics for Health Related Effects," J. Agric. Food Chem. 2005, 53, 5922-5931. (Year: 2005).*
International Search Report for Application No. PCT/EP2020/081308 dated Jan. 26, 2021.
Written Opinion for Application No. PCT/EP2020/081308 dated Jan. 26, 2021.
Great Britain Search Report for Application No. 1916219.7 dated May 15, 2020.
Franziska Pohl, et al., GST-4-Dependent Suppression of Neurodegeneration in C. elegans Models of Parkinson's and Machado-Joseph Disease by Rapeseed Pomace Extract Supplementation, Frontiers in Neuroscience, Oct. 17, 2019, vol. 13, Article 1091.
Rapeflower Capsule Pack, Mintel, Jan. 2016.

(Continued)

*Primary Examiner* — Jeffrey S Lundgren
*Assistant Examiner* — Michael J Schmitt
(74) *Attorney, Agent, or Firm* — Curatolo Sidoti & Trillis Co., LPA; Salvatore A. Sidoti; Floyd Trillis, III

(57) ABSTRACT

The present invention relates to compounds having a lipid affinity of less than 15% by weight of the compound (such as a log P of −0.75 or less) for use in targeting mitochondria to reduce, inhibit or prevent the formation of mitochondrial reactive oxygen species and for use in treating or preventing a pathological condition associated with increased levels of mitochondrial reactive oxygen species, and for non-therapeutic uses, such as enhancing sports performance and reducing, inhibiting or preventing the formation of mitochondrial reactive oxygen species during exercise, resulting in maintenance of muscle strength and/or a reduction in muscle fatigue, and associated methods. The present invention also relates to extracts and compositions comprising compounds having a lipid affinity of less than 15% (such as a log P of −0.75 or less) for the same uses.

23 Claims, 22 Drawing Sheets

(56) References Cited

OTHER PUBLICATIONS

Kyari Yates, et al., Determination of sinapine in rapeseed pomace extract: Its antioxidant and acetylcholinesterase inhibition properties, Food Chemistry, Oct. 10, 2018, pp. 768-775, vol. 276, Elsevier.
Yang Chun-Yan, et al., Neuroprotective Effects of Sinapine on PC12 Cells Apoptosis Induced by Sodium Dithionite, Chinese Journal of Natural Medicines, May 20, 2008, pp. 205-209, vol. 6, Issue 3, Science Direct, Elsevier.
Kesheng Zhao, et al., Cell-permeable Peptide Antioxidants Targeted to Inner Mitochondrial Membrane inhibit Mitochondrial Swelling, Oxidative Cell Death, and Reperfusion Injury, The Journal of Biological Chemistry, Jun. 2, 2004, pp. 34682-34690, vol. 279, Issue 33, The American Society for Biochemistry and Molecular Biology, Inc., U.S.A.
Erwann Durand, et al., Evaluation of the ROS Inhibiting Activity and Mitochondrial Targeting of Phenolic Compounds in Fibroblast Cells Model System and Enhancement of Efficiency by Natural Deep Eutectic Solvent (NADES) Formulation, Pharm Res, Feb. 21, 2017, pp. 1134-1146, vol. 34, Issue 5, Springer.
Thangarasu Silambarasan, et al., Sinapic acid protects heart against ischemia/reperfusion injury and H9c2 cardiomyoblast cells against oxidative stress, Biochemical and Biophysical Research Communications, Dec. 13, 2014, pp. 853-859, vol. 456, Issue 4, Elsevier.
Youdong Li, et al., Sinapine reduces non-alcoholic fatty liver disease in mice by modulating the composition of the gut microbiota, Food & Function, Royal Society of Chemistry, May 24, 2019, pp. 3637-3649, vol. 18, Issue 6, The Royal Society of Chemistry.
Andres Hernandez, et al., Antioxidants and skeletal muscle performance: "Common knowledge" vs. experimental evidence, Frontiers in Physiology, Mar. 12, 2012, pp. 1-6, vol. 3, Article 46.
Doria Boulghobra, et al., Sinapine, but not sinapic acid, counteracts mitochondrial oxidative stress in cardiomyocytes, Redox Biology, May 19, 2020, pp. 1-11, vol. 34, Issue 101554, Elsevier B.V.
P.K. Jensen, Antimycin-insensitive oxidation of succinate and reduced nicotinamide-adenine dinucleotide in electron-transport particles I. pH dependency and hydrogen peroxide formation, Biochimica et Biophysica Acta (BBA)—Enzymology and Biological Oxidation, Aug. 10, 1966, pp. 157-166, vol. 122, Issue 2, Elsevier.
Saima Kausar, et al., The Role of Mitochondria in Reactive Oxygen Species Generation and Its Implications for Neurodegenerative Diseases, Cells, Dec. 17, 2018, pp. 1-19, vol. 7, Issue 274, MDPI.
Charlotte Bonnard, et al., Mitochondrial dysfunction results from oxidative stress in the skeletal muscle of diet-induced insulin-resistant mice, The Journal of Clinical Investigation, Feb. 1, 2008, pp. 789-800, vol. 118, Issue 2, The American Society for Clinical Investigation.
Heiko Bugger, et al., Mitochondria in the diabetic heart, Cardiovascular Research, Jul. 16, 2010, pp. 229-240, vol. 88.
Simran S. Sabharwal, et al., Mitochondrial ROS in cancer: initiators, amplifiers or an Achilles' heel?, National Rev. Cancer, Nov. 2014, pp. 709-721, vol. 14, Issue 11.
Gabriel Loor, et al., Mitochondrial oxidant stress triggers cell death in simulated ischemia-reperfusion, Biochim Biophys Acta, Jul. 2011, pp. 1382-1394, vol. 1813, Issue 7, Elsevier B.V.
Edward T. Chouchani, et al., A Unifying Mechanism for Mitochondrial Superoxide Production during Ischemia-Reperfusion Injury, Cell Metabolism, pp. 254-263, Feb. 9, 2016, vol. 23, Issue 2, Cell Press.
Tomomi Ide, et al., Mitochondrial Electron Transport Complex I Is a Potential Source of Oxygen Free Radicals in the Failing Myocardium, Circulation Research, Aug. 20, 1999, pp. 357-363, vol. 85, Issue 4, American Heart Association, Inc.
Lucas Andre, et al., Subendocardial increase in reactive oxygen species production affects regional contractile function in ischemic heart failure, Antioxidants & Redox Signaling, Feb. 14, 2013, pp. 1009-1020, vol. 18, Issue 9.
David A. Brown, et al., Mitochondrial function as a therapeutic target in heart failure, Nature Reviews Cardiology, Apr. 1, 2017, pp. 235-250, vol. 14, Issue 4.
Corey R. Hart, et al., Increased skeletal muscle mitochondrial free radical production in peripheral arterial disease despite preserved mitochondrial respiratory capacity, Experimental Physiology, Jun. 2018, pp. 838-850, vol. 103, Issue 6.
Takeshi Nishikawa, et al., Normalizing Mitochondrial Superoxide Production Blocks Three Pathways of Hyperglycaemic Damage, Nature, Apr. 13, 2000, pp. 787-790, vol. 404, Macmillan Magazines Ltd.
Coeh H. Wiegman, et al., Oxidative stress-induced mitochondrial dysfunction drives inflammation and airway smooth muscle remodeling in patients with chronic obstructive pulmonary disease, The Journal of Allergy and Clinical Immunology, Sep. 2015, pp. 769-780, vol. 136, Issue 3.
L. Puente-Maestu, et al., Abnormal mitochondrial function in locomotor and respiratory muscles of COPD patients, European Respiratory Journal, 2009, pp. 1045-1052, vol. 33, Issue 5.
Luis Puente-Maestu, et al., Abnormal transition pore kinetics and cytochrome C release in muscle mitochondria of patients with chronic obstructive pulmonary disease, American Journal of Respiratory Cell and Molecular Biology, Jun. 2009, pp. 746-750, vol. 40, Issue 6.
Luis Puente-Maestu, et al., Site of mitochondrial reactive oxygen species production in skeletal muscle of chronic obstructive pulmonary disease and its relationship with exercise oxidative stress, American Journal of Respiratory Cell and Molecular Biology, Sep. 2012, pp. 358-362, vol. 47, Issue 3.
Anna E. Dikalova, et al., Therapeutic targeting of mitochondrial superoxide in hypertension, Circulation Research, Jul. 9, 2010, pp. 106-116, vol. 107, Issue 1.
Ariel C. Bulua, et al., Mitochondrial reactive oxygen species promote production of proinflammatory cytokines and are elevated in TNFR1-associated periodic syndrome (TRAPS), Journal of Experimental Medicine, pp. 519-533, Mar. 14, 2011, vol. 208, Issue 3.
E.A. Liberman, et al., Mechanism of Coupling of Oxidative Phosphorylation and the Membrane Potential of Mitochondria, Nature, Jun. 14, 1969, pp. 1076-1078, vol. 222.
L. E. Bakeeva, et al., Conversion of biomembrane-produced energy into electric form. II. Intact mitochondria, Biochimica et Biophysica Acta (BBA)—Bioenergetics, Aug. 4, 1970, pp. 13-21, vol. 216, Issue 1, Elsevier.
Geoffrey F. Kelso, et al., Selective targeting of a redox-active ubiquinone to mitochondria within cells: antioxidant and antiapoptotic properties, The Journal of Biological Chemistry, pp. 4588-4596, Feb. 16, 2001, vol. 276, Issue 7, JBC Papers in Press, U.S.A.
Robin A. J. Smith, et al., Selective targeting of an antioxidant to mitochondria, European Journal of Biochemistry, Aug. 1999, pp. 709-716, vol. 263, Issue 3.
Lucia Biasutto, et al., Development of mitochondria-targeted derivatives of resveratrol, Bioorganic & Medicinal Chemistry Letters, Oct. 15, 2008, pp. 5594-5597, vol. 18, Issue 20, Elsevier.
Jan Trnka, et al., A mitochondria-targeted nitroxide is reduced to its hydroxylamine by ubiquinol in mitochondria, Free Radical Biology and Medicine, Apr. 1, 2008, pp. 1406-1419, vol. 44, Issue 7, Elsevier.
M. F. Ross, et al., Lipophilic triphenylphosphonium cations as tools in mitochondrial bioenergetics and free radical biology, Biochemistry (Mosc), Feb. 2005, pp. 273-283, vol. 70, Issue 2, Pleiades Publishing, Inc.
M. P. Murphy, Selective targeting of bioactive compounds to mitochondria, Trends in Biotechnology, Aug. 1, 1997, pp. 326-330, vol. 15, Issue 8, CellPress.

* cited by examiner

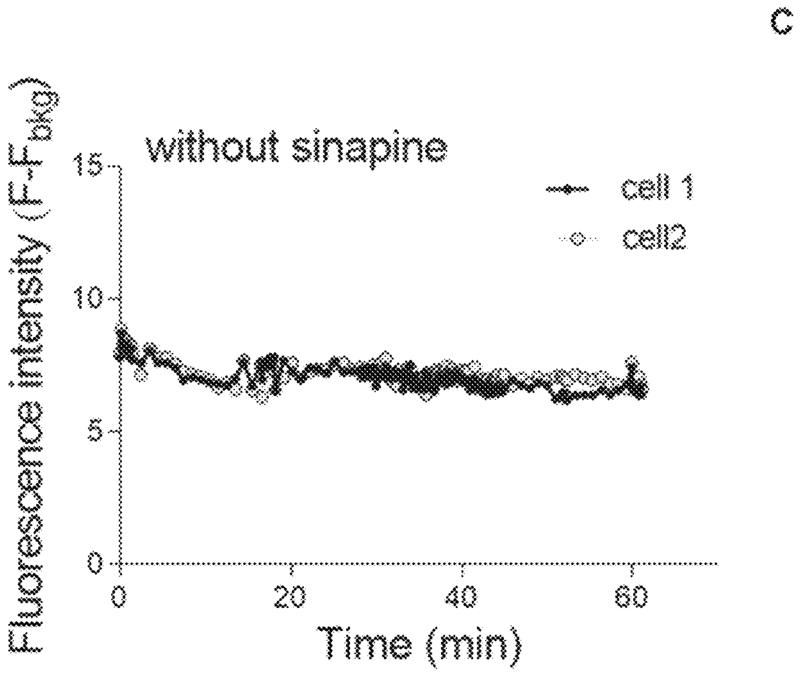
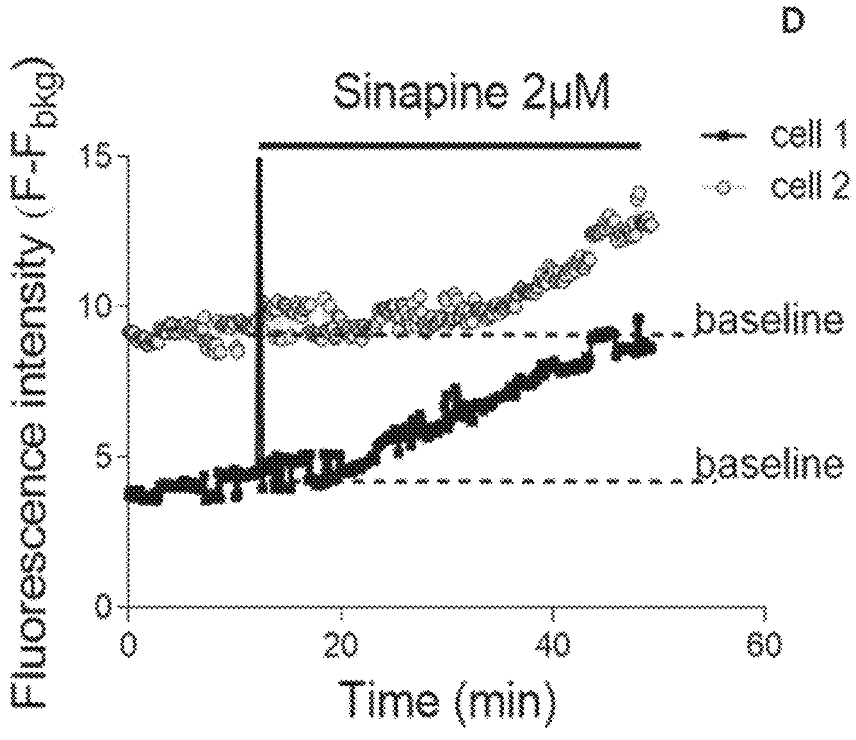
Figure 3 C and D

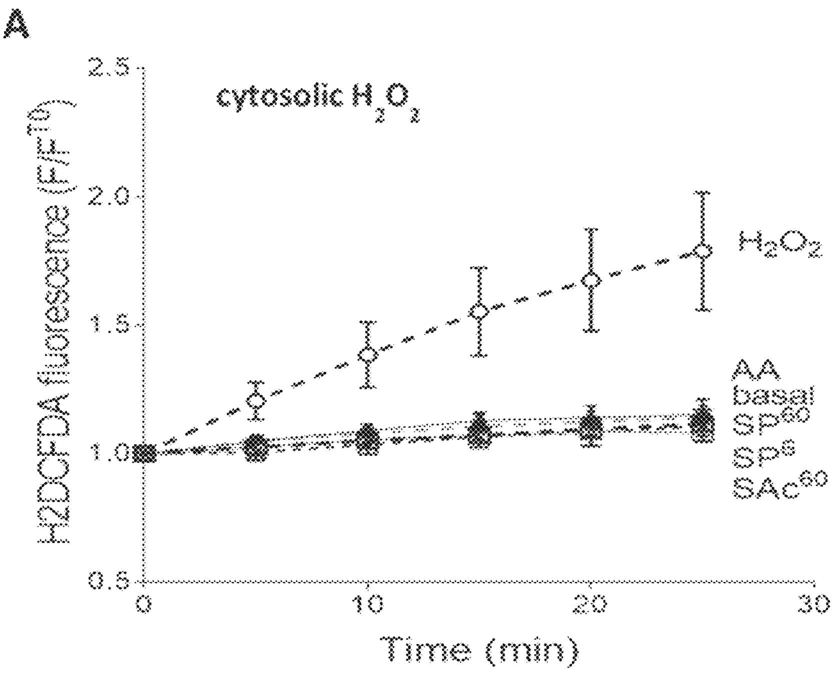
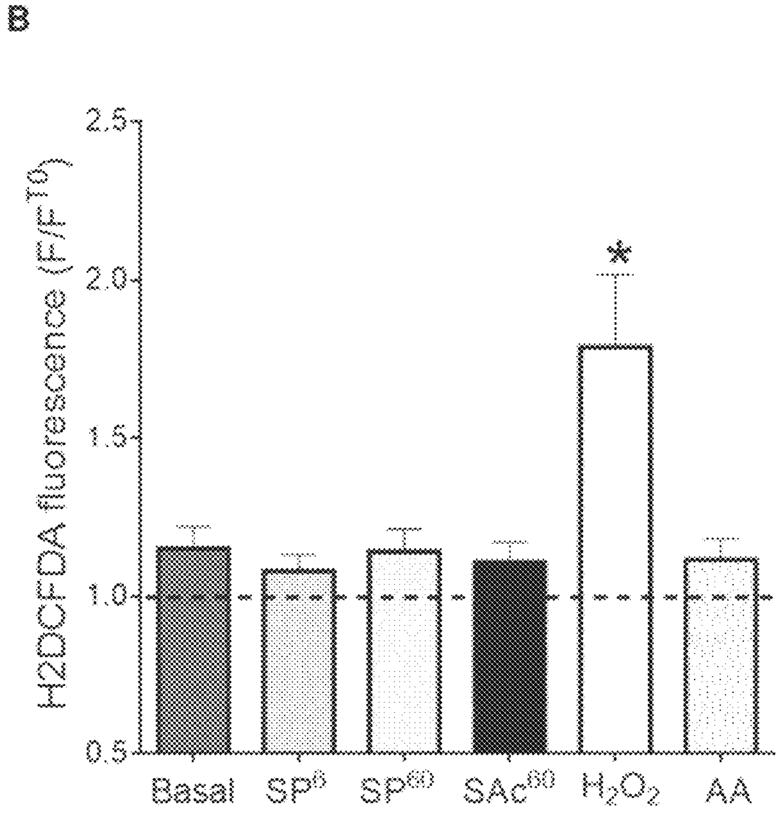
Figure 6 A and B

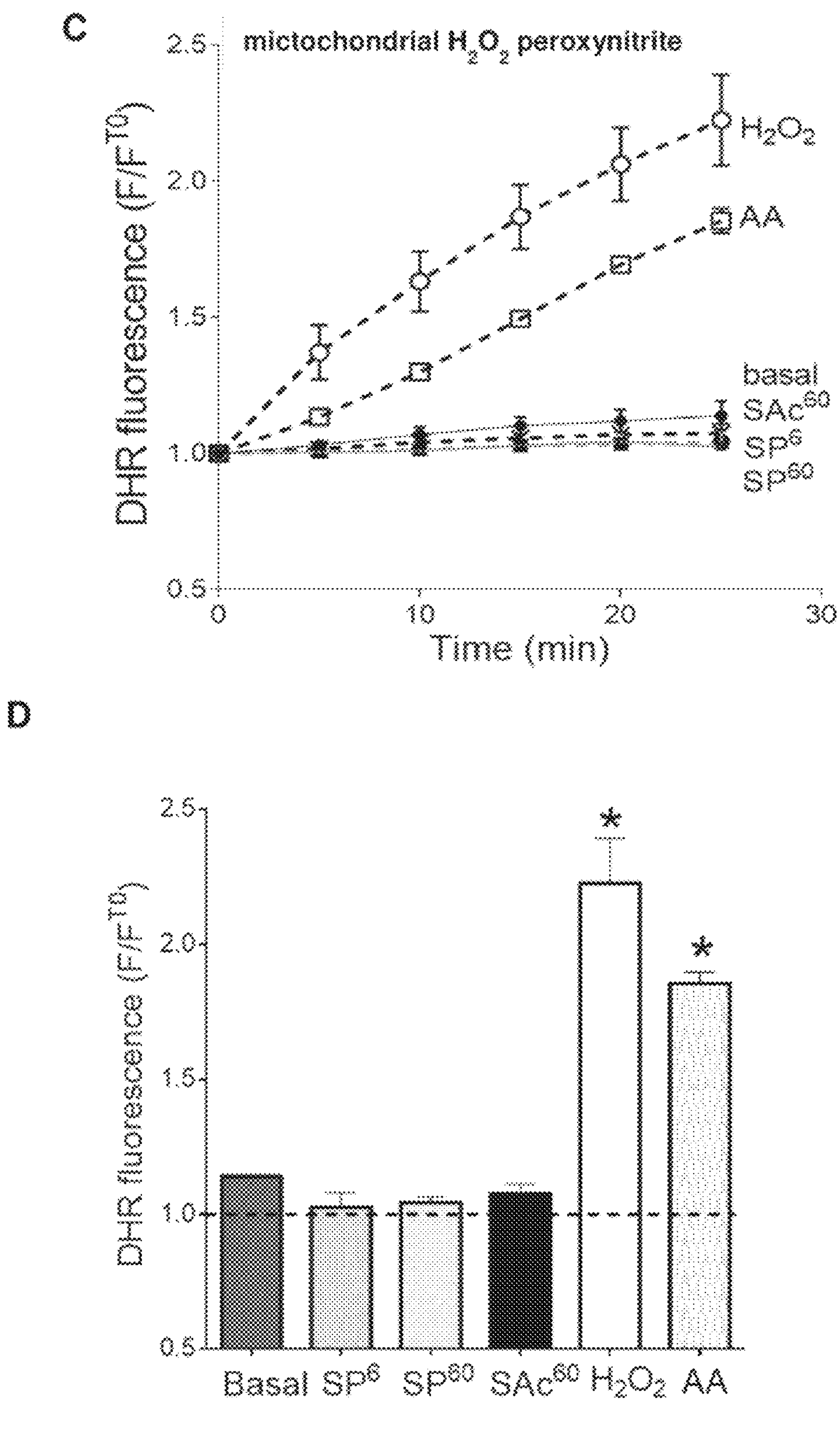
Figure 6 C and D

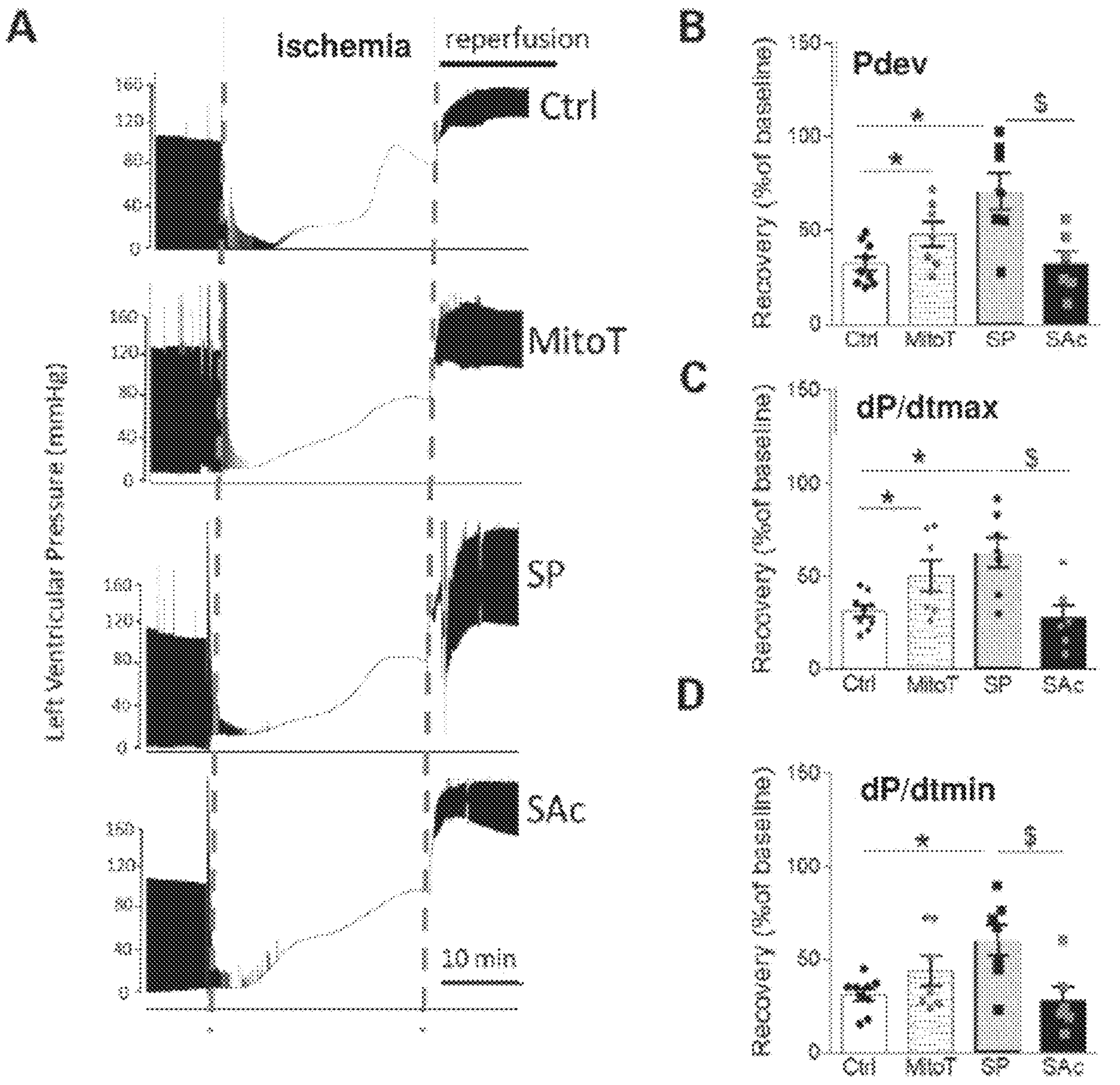
Figure 8 A, B, C and D

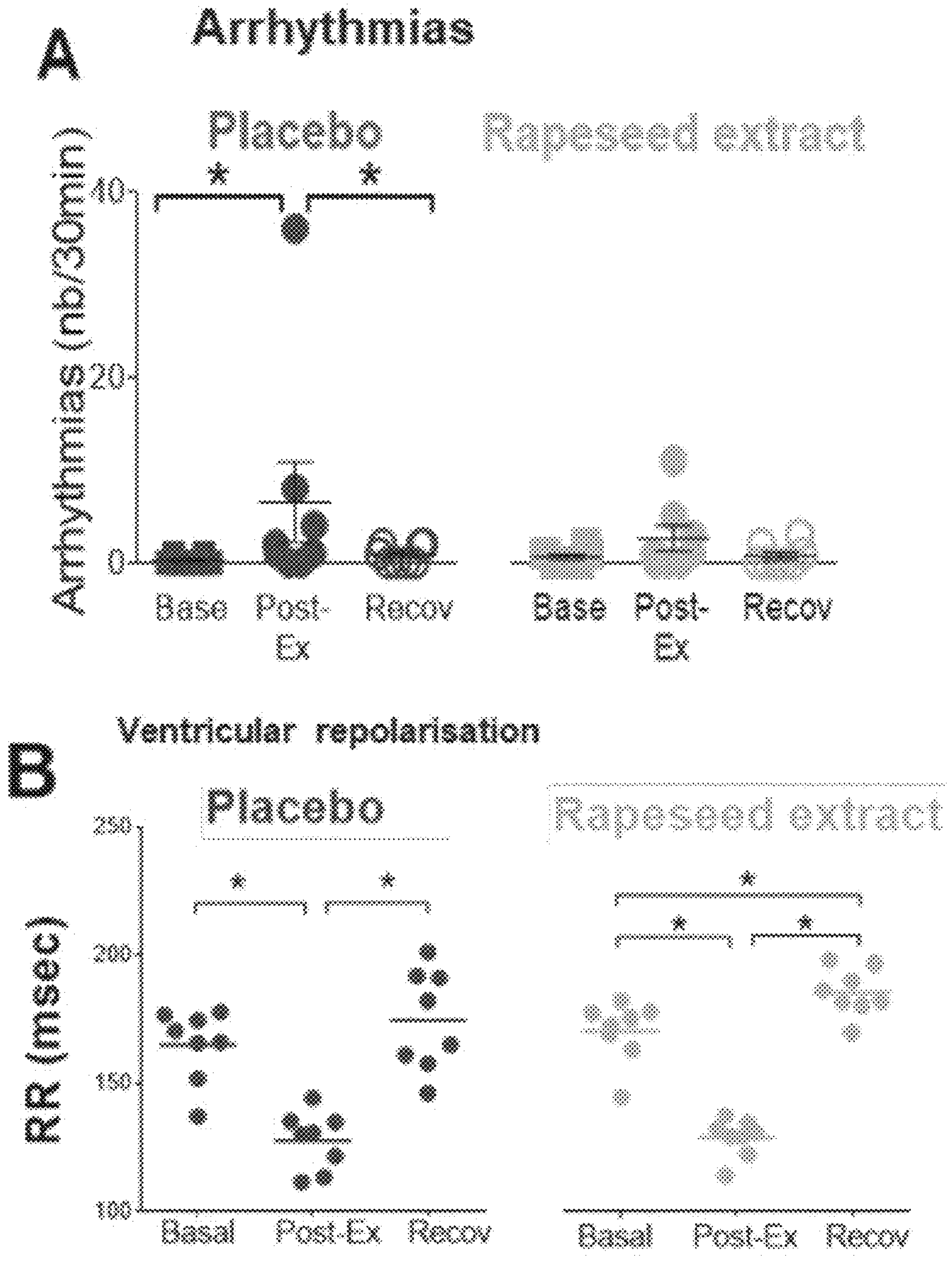
Figure 12 A and B

MITOCHONDRIA-TARGETING ANTIOXIDANTS

CROSS REFERENCE TO RELATED APPLICATIONS

This application is a national stage application of International Application No. PCT/EP2020/81308, filed 6 Nov. 2020, which claims priority from Great Britain Patent Application No. 1916219.7, filed 7 Nov. 2019, both of which applications are incorporated herein by reference.

The present invention relates to compounds having a lipid affinity of less than 15% by weight of the compound (such as a log P of −0.75 or less) for use in targeting mitochondria to reduce, inhibit or prevent the formation of mitochondrial reactive oxygen species and for use in treating or preventing a pathological condition associated with increased levels of mitochondrial reactive oxygen species and for non-therapeutic uses, such as enhancing sports performance and reducing, inhibiting or preventing the formation of mitochondrial reactive oxygen species during exercise, resulting in maintenance of muscle strength and/or a reduction in muscle fatigue and associated methods. The present invention also relates to extracts and compositions comprising compounds having a lipid affinity of less than 15% (such as a log P of −0.75 or less) for the same uses.

The listing or discussion of an apparently prior-published document in this specification should not necessarily be taken as an acknowledgement that the document is part of the state of the art or is common general knowledge.

Mitochondria are intracellular organelles responsible for energy metabolism and are present in all eukaryotic cells. However, they are believed to be the major intracellular source of reactive oxygen species (ROS). Mitochondrial ROS (mtROS) are reactive oxygen species (ROS) that are produced by mitochondria and are referred to as "mitochondrial" as long as they are located in mitochondria. For example, $H_2O_2$, hydroxyradicals, and superoxide anions that are located in mitochondria, which are damaging, particularly to neural and muscle tissues which have high energy demand.

An imbalance between ROS and the antioxidant defenses can disturb the normal redox state of cells and cause a pathological condition known as oxidative stress.

Since the discovery in 1966 that mitochondria produce ROS (mtROS) (Jensen PK. Antimycin-insensitive oxidation of succinate and reduced nicotinamide-adenine dinucleotide in electron-transport particles, II. Steroid effects. Biochim. Biophys. Acta 1966, 122, 167-174), these partially reduced forms of oxygen, have been associated with a growing number of pathological conditions, particularly when present in excess compared to antioxidants. For example, neurodegenerative diseases (Kausar et al. The role of mitochondria in reactive oxygen species generation and its implications for neurodegenerative diseases. Cell 2018, 7, 274-293), such as Parkinson's disease. Alzheimers disease, and Huntington's Chorea; diabetes and insulin-resistance (Bonnard et al. Mitochondrial dysfunction results from oxidative stress in the skeletal muscle of diet-induced insulin-resistant mice. J Clin Invest. 2008, 118, 789-800; Bugger and Abel. Mitochondria in the diabetic heart. Cardiovasc. Res. 2010, 88, 229-240); as well as cancer, where mitochondrial ROS amplify the tumorigenic phenotype and accelerate the accumulation of additional mutations that lead to metastatic behaviour (Sabharwal and Schumacker, Mitochondrial ROS in cancer: initiators, amplifiers or an Achilles' heel? Nat. Rev. Cancer volume 2014, 14, 709-721); inflammation and ischemic-reperfusion (Loor et al., Mitochondrial oxidant stress triggers cell death in simulated ischemia-reperfusion. Biochim. Biophys. Acta-Mol. Cell Res. 2011, 1813, 1382-1394; Chouchani et al, A unifying mechanism for mitochondrial superoxide production during ischemia-reperfusion injury): heart failure (Ide et al. Mitochondrial electron transport complex I is a potential source of oxygen free radicals in the failing myocardium. Circ. Res. 1999, 85, 357-363, Andre et alt Subendocardial increase in reactive oxygen species production affects regional contractile function in ischemic heart failure. Antiox. Redox Signal. 2013, 18, 1009-1020; Brown et al. Mitochondrial function as a therapeutic target in heart failure. Nat. Rev. Cardiol. 2017, 14, 238-250); peripheral artery diseases (Hart et al. Increased skeletal muscle mitochondrial free radical production in peripheral arterial disease despite preserved mitochondrial respiratory capacity. Exp. Physiol. 2018, 103, 838-850); hyperglycemia (Nishikawa et al. Normalizing mitochondrial superoxide production blocks three pathways of hyperglycaemic damage. Nature 2000, 404, 787-790); chronic obstructive pulmonary diseases (Wiegman et al. Oxidative stress-induced mitochondrial dysfunction drives inflammation and airway smooth muscle remodeling in patients with chronic obstructive pulmonary disease. J. Allergy Clin. Immunol. 2015, 136, 769-780; Puente-Maestu et al. Abnormal mitochondrial function in locomotor and respiratory muscles of COPD patients. Eur. Respir J. 2009, 33, 1045-1052; Puente-Maestu et al. Abnormal transition pore kinetics and cytochrome C release in muscle mitochondria of patients with chronic obstructive pulmonary disease. Am. J. Respir. Cell Mol. Biol. 2009, 40, 746-750; Puente-Maestu et al. Site of mitochondrial reactive oxygen species production in skeletal muscle of chronic obstructive pulmonary disease and its relationship with exercise oxidative stress. Am. J. Respir. Cell Mol. Biol. 2012, 47, 358-362), hypertension (Dikalova et al. Therapeutic targeting of mitochondrial superoxide in hypertension. Circ Res. 2010, 107, 106-116), and inflammatory diseases (Bulua et al. Mitochondrial reactive oxygen species promote production of proinflammatory cytokines and are elevated in TNFR1-associated periodic syndrome (TRAPS). J. Exp. Med. 2011, 208, 519-533).

Given the important role played by mtROS in human pathophysiology, mitochondria are an obvious target for antioxidants capable to reduce mtROS and restore the balance between pro- and antioxidants.

An interesting feature of mitochondria that can be utilized for this purpose is the negatively charged compartments they form. The mitochondrial respiratory chain participates in transfer of electrons to $O_2$. This transport generates a proton gradient that is used to drive the production of ATP by ATP synthase. Thus, a negative potential of 150-180 mV is generated across the inner mitochondrial membrane.

Fifty years ago, dibenzylammonium cation was shown to accumulate in the mitochondrial matrix in response to this negative potential (Liberman et al., Mechanism of coupling of oxidative phosphorylation and the membrane potential of mitochondria. Nature 1969, 222, 1076-1078).

Later, other synthetic substances, such as the methyltriphenylphosphonium cation, were used to enter mitochondria (Bakeeva et al., Conversion of biomembrane-produced energy into electric form. II, Intact mitochondria. Biochim. Biophys. Acta 1970, 216, 13-21).

The finding that some synthetic cations can be taken up by mitochondria has resulted in the specific development of antioxidants in which a cationic moiety, such as the triphenylphosphonium cation ($TPP^+$), is covalently grafted to a neutral antioxidant, thus imparting the latter with mitochondria-targeting properties.

Since the negative membrane potential is not found in any other subcellular compartments, this electromotive force offers a very selective way to deliver antioxidants to these organelles.

Examples of such mitochondriotropic antioxidants include TPP-ubiquinone, the so-called MitoQ (Kelso et al. Selective targeting of a redox-active ubiquinone to mitochondria within cells: antioxidant and antiapoptotic properties. J. Biol. Chem. 2001, 276, 4588-4596), TPP-tocopherol (Smith et al. Selective targeting of an antioxidant to mitochondria. Eur. J. Biochem. 1999, 263, 709-716), TPP-resveratrol (Biasutto et al. Development of mitochondria-targeted derivatives of resveratrol. Bioorg. Med. Chem. Lett. 2008, 18, 5594-5597), and TPP-nitroxide, the so-called MitoTEMPO (Trnka et al. A mitochondria-targeted nitroxide is reduced to its hydroxylamine by ubiquinol in mitochondria. Free Rad. Biol. Med. 2008, 44, 1406-1419). These TPP-conjugates have been reported to significantly decrease the level of various reactive species including ROS (e.g. $H_2O_2$, *NO. $ONOO^-$, peroxyradicals, and alkoxyradicals).

However, the uptake of cations by mitochondria is thought to not only be caused by the positive charge of the cation, but also by the hydrophobicity of the molecule (Ross et al. Lipophilic triphenylphosphonium cations as tools in mitochondrial bioenergetics and free radical biology. Biochem. (Moscow) 2005, 70, 222-230). For example, the hydrophobicity of tetraphenylphosphonium or triphenylmethylphosphonium is thought to allow them to pass easily through the phospholipid bilayers into mitochondria (Murphy. Trends Biotechnol. 1997, 15, 326-330). According to Murphy and colleagues, this contrasts with hydrophilic cations which cannot cross biological membrane except when transport is facilitated by ionophores or carrier proteins (Ross et al. Lipophilic triphenylphosphonium cations as tools in mitochondrial bioenergetics and free radical biology. Biochem. (Moscow) 2005, 70, 222-230).

The relative impermeability of biological membranes to hydrophilic cations is thought to be largely due to the high energy demand of moving an ion from an aqueous environment to the non-polar lipid interior of the membrane. Thus, currently only lipophilic antioxidant cations (such as MitoQ3, MitoQ5, or MitoQ10) or amphiphilic antioxidant cations, which equally partition between lipids and water (such as MitoTEMPO), can be taken up by mitochondria.

The present inventors have surprisingly and unexpectedly found that compounds having a lipid affinity of less than 15% by weight of the compound (such as a log P of −0.75 or less), such as sinapine, can (i) enter mitochondria very efficiently, (ii) reduce, inhibit or prevent the formation of mitochondrial reactive oxygen species, and/or (i) prevent or treat a pathological condition associated with increased levels of mitochondrial reactive oxygen species.

Accordingly, the present invention provides a compound having a lipid affinity of less than 15% by weight of the compound (such as a log P of −0.75 or less) for use in reducing, inhibiting or preventing the formation of mitochondrial reactive oxygen species.

The term "lipid affinity" as used herein, refers to the percentage of the compound that partitions into a lipid phase when this compound is placed in a two phase-system containing water and an immiscible phase, usually octanol. For example, in the present invention, the compound having a lipid affinity of less than 15% by weight of the compound, means that less than 15% of the compound partitions into a lipid phase.

The compound having a lipid affinity of less than 15% as defined above may have a lipid affinity of less than 10% or less than 5%. For example, the compound having a lipid affinity of less than 15% may have a lipid affinity of from about 0.001% to about 10%, such as from about 0.1% to about 5%, or from about 0.5% to about 10% or from about 1% to about 5% by weight of the compound.

Typically, the compound having a lipid affinity of less than 15% as defined above has a log P of −0.75 or less, such as a log P of −1.5 or less. For example, a log P of from about −5.0 to about −0.75, or from about −2.5 to about −1.0.

As used herein, the term "log P" is the partition coefficient of a molecule between an aqueous and lipophilic phases, usually octanol and water.

The present invention also provides a compound having a lipid affinity of less than 15% (such as a log P of −0.75 or less), for use in treating or preventing a pathological condition associated with increased levels of mitochondrial reactive oxygen species.

The present invention also provides a method of reducing, inhibiting or preventing the formation of mitochondrial reactive oxygen species comprising the administration of a therapeutically effective amount of a compound having a lipid affinity of less than 15% (such as a log P of −0.75 or less).

The present invention also provides the use of a compound having a lipid affinity of less than 15% (such as a log P of −0.75 or less) in the manufacture of a medicament for reducing, inhibiting or preventing the formation of mitochondrial reactive oxygen species.

The present invention also provides the use (for example, the non-therapeutic use) of a compound having a lipid affinity of less than 15% (such as a log P of −0.75 or less) for reducing, inhibiting or preventing the formation of mitochondrial reactive oxygen species, for example, in-vitro.

The present invention also provides a method of treating or preventing a pathological condition associated with increased levels of mitochondrial reactive oxygen species comprising the administration of a therapeutically effective amount of a compound having a lipid affinity of less than 15% (such as a log P of −0.75 or less).

The present invention also provides the use of a compound having a lipid affinity of less than 15% (such as a log P of −0.75 or less), in the manufacture of a medicament for treating or preventing a pathological condition associated with increased levels of mitochondrial reactive oxygen species.

The present invention also provides a method of enhancing sports performance, comprising the administration of an effective amount of a compound having a lipid affinity of less than 15% (such as a log P of −0.75 or less) to a subject in need thereof to reduce, inhibit or prevent the formation of mitochondrial reactive oxygen species.

Also provided is a method of reducing, inhibiting or preventing the formation of mitochondrial reactive oxygen species during and/or after exercise comprising the administration of an effective amount of a compound having a lipid affinity of less than 15% (such as a log P of −0.75 or less) to a subject in need thereof.

Further also provided is a method of enhancing muscle recovery during and/or after exercise comprising the administration of an effective amount of a compound having a lipid affinity of less than 15% (such as a log P of −0.75 or less) to a subject in need thereof.

It is thought that in the methods described above, the administration of an effective amount of a compound having a lipid affinity of less than 15% (such as a log P of −0.75 or less) reduces, inhibits or prevents the deleterious effects that mtROS generated during exercise have on muscle (i.e. skeletal muscle) resulting in maintenance of muscle strength and/or a reduction in muscle fatigue and/or improved muscle recovery during and/or after exercise.

As used herein, the term "exercise" or "physical exercise" means that the heart rate is from about 40% to about 100% of maximum, such as from about 50% to about 90% or from about 60% to about 80%, or about 70%. For example, a 20 year old human would be expected to have a maximum heart rate of 220-200=200 beats per minute (BPM). Thus, exercise would be considered to be when the heart rate reached a rate from 80 BPM to 200 BPM, or from 100 BPM to 180 BPM or from about 120 BPM to 160 BPM, or about 140 BPM.

The compound having a lipid affinity of less than 15% may be a mitochondria targeting compound. For example, the present invention may provide a mitochondria targeting compound having a lipid affinity of less than 15% (such as a log P of −0.75 or less) for use in reducing, inhibiting or preventing the formation of mitochondrial reactive oxygen species.

The present invention also provides a method of reducing, inhibiting or preventing the formation of mitochondrial reactive oxygen species comprising the administration of a therapeutically effective amount of a mitochondria targeting compound having a lipid affinity of less than 15% (such as a log P of −0.75 or less).

The present invention may also provide the use of a mitochondria targeting compound having a lipid affinity of less than 15% (such as a log P of −0.75 or less) in the manufacture of a medicament for reducing, inhibiting or preventing the formation of mitochondrial reactive oxygen species.

The present invention also provides the use (for example, the non-therapeutic use) of a mitochondria targeting compound having a lipid affinity of less than 15% (such as a log P of −0.75 or less) for reducing, inhibiting or preventing the formation of mitochondrial reactive oxygen species, for example, in-vitro.

The present invention may also provide a mitochondria targeting compound having a lipid affinity of less than 15% (such as a log P of −0.75 or less) for use in treating or preventing a pathological condition associated with increased levels of mitochondrial reactive oxygen species.

The present invention also provides a method of treating or preventing a pathological condition associated with increased levels of mitochondrial reactive oxygen species comprising the administration of a therapeutically effective amount of a mitochondria targeting compound having a lipid affinity of less than 15% (such as a log P of −0.75 or less).

The present invention may also provide the use of a mitochondria targeting compound having a lipid affinity of less than 15% (such as a log P of −0.75 or less) in the manufacture of a medicament for treating or preventing a pathological condition associated with increased levels of mitochondrial reactive oxygen species.

The present invention also provides a method of enhancing sports performance, comprising the administration of an effective amount a mitochondria targeting compound having a lipid affinity of less than 15% (such as a log P of −0.75 or less) to a subject in need thereof to reduce, inhibit or prevent the formation of mitochondrial reactive oxygen species.

Also provided is a method of reducing, inhibiting or preventing the formation of mitochondrial reactive oxygen species during and/or after exercise comprising the administration of an effective amount of a mitochondria targeting compound having a lipid affinity of less than 15% (such as a log P of −0.75 or less) to a subject in need thereof.

Further also provided is a method of enhancing muscle recovery during and/or after exercise comprising the administration of an effective amount of a mitochondria targeting compound having a lipid affinity of less than 15% (such as a log P of −0.75 or less) to a subject in need thereof.

The compound having a lipid affinity of less than 15% may be a compound that is capable of reducing, inhibiting or preventing the formation of mitochondrial reactive oxygen species. For example, the present invention may provide a compound having a lipid affinity of less than 15% (such as a log P of −0.75 or less) capable of reducing, inhibiting or preventing the formation of mitochondrial reactive oxygen species for use in reducing, inhibiting or preventing the formation of mitochondrial reactive oxygen species.

The present invention also provides a method of reducing, inhibiting or preventing the formation of mitochondrial reactive oxygen species comprising the administration of a compound having a lipid affinity of less than 15% (such as a log P of −0.75 or less) capable of reducing, inhibiting or preventing the formation of mitochondrial reactive oxygen species.

The present invention may also provide the use of a compound having a lipid affinity of less than 15% (such as a log P of −0.75 or less) capable of reducing, inhibiting or preventing the formation of mitochondrial reactive oxygen species in the manufacture of a medicament for reducing, inhibiting or preventing the formation of mitochondrial reactive oxygen species.

The present invention also provides the use (for example, the non-therapeutic use) of a compound having a lipid affinity of less than 15% (such as a log P of −0.75 or less) capable of reducing, inhibiting or preventing the formation of mitochondrial reactive oxygen species for reducing, inhibiting or preventing the formation of mitochondrial reactive oxygen species, for example, in-vitro.

The present invention may also provide a compound having a lipid affinity of less than 15% (such as a log P of −0.75 or less) capable of reducing, inhibiting or preventing the formation of mitochondrial reactive oxygen species for use in treating or preventing a pathological condition associated with increased levels of mitochondrial reactive oxygen species.

The present invention also provides a method of treating or preventing a pathological condition associated with increased levels of mitochondrial reactive oxygen species comprising the administration of a compound having a lipid affinity of less than 15% (such as a log P of −0.75 or less) capable of reducing, inhibiting or preventing the formation of mitochondrial reactive oxygen species.

The present invention may also provide the use of a compound having a lipid affinity of less than 15% (such as a log P of −0.75 or less) capable of reducing, inhibiting or preventing the formation of mitochondrial reactive oxygen species in the manufacture of a medicament for treating or preventing a pathological condition associated with increased levels of mitochondrial reactive oxygen species.

The present invention also provides a method of enhancing sports performance, comprising the administration of an effective amount of a compound having a lipid affinity of less than 15% (such as a log P of −0.75 or less) capable of reducing, inhibiting or preventing the formation of mitochondrial reactive oxygen species to a subject in need thereof to reduce, inhibit or prevent the formation of mitochondrial reactive oxygen species.

Also provided is a method of reducing, inhibiting or preventing the formation of mitochondrial reactive oxygen species during and/or after exercise comprising the administration of an effective amount of a compound having a lipid affinity of less than 15% (such as a log P of −0.75 or less) capable of reducing, inhibiting or preventing the formation of mitochondrial reactive oxygen species to a subject in need thereof.

Further also provided is a method of enhancing muscle recovery during and/or after exercise comprising the administration of an effective amount of a compound having a lipid affinity of less than 15% (such as a log P of −0.75 or less) capable of reducing, inhibiting or preventing the formation of mitochondrial reactive oxygen species to a subject in need thereof.

Thus, the present invention may also provide a mitochondria targeting compound having a lipid affinity of less than 15% (such as a log P of −0.75 or less) capable of reducing, inhibiting or preventing the formation of mitochondrial reactive oxygen species for use in reducing, inhibiting or preventing the formation of mitochondrial reactive oxygen species.

The present invention also provides a method of reducing, inhibiting or preventing the formation of mitochondrial reactive oxygen species comprising the administration of a mitochondria targeting compound having a lipid affinity of less than 15% (such as a log P of −0.75 or less) capable of reducing, inhibiting or preventing the formation of mitochondrial reactive oxygen species.

The present invention may also provide the use of a mitochondria targeting compound having a lipid affinity of less than 15% (such as a log P of −0.75 or less) capable of reducing, inhibiting or preventing the formation of mitochondrial reactive oxygen species in the manufacture of a medicament for reducing, inhibiting or preventing the formation of mitochondrial reactive oxygen species.

The present invention also provides the use (for example, the non-therapeutic use) of a mitochondria targeting compound having a lipid affinity of less than 15% (such as a log P of −0.75 or less) capable of reducing, inhibiting or preventing the formation of mitochondrial reactive oxygen species for reducing, inhibiting or preventing the formation of mitochondrial reactive oxygen species, for example, in-vitro.

The present invention may also provide a mitochondria targeting compound having a lipid affinity of less than 15% (such as a log P of −0.75 or less) capable of reducing, inhibiting or preventing the formation of mitochondrial reactive oxygen species for use in treating or preventing a pathological condition associated with increased levels of mitochondrial reactive oxygen species.

The present invention also provides a method of treating or preventing a pathological condition associated with increased levels of mitochondrial reactive oxygen species comprising the administration of a mitochondria targeting compound having a lipid affinity of less than 15% (such as a log P of −0.75 or less) capable of reducing, inhibiting or preventing the formation of mitochondrial reactive oxygen species.

The present invention may also provide the use of a mitochondria targeting compound having a lipid affinity of less than 15% (such as a log P of −0.75 or less) capable of reducing, inhibiting or preventing the formation of mitochondrial reactive oxygen species in the manufacture of a medicament for treating or preventing a pathological condition associated with increased levels of mitochondrial reactive oxygen species.

The present invention also provides a method of enhancing sports performance, comprising the administration of an effective amount of a mitochondria targeting compound having a lipid affinity of less than 15% (such as a log P of −0.75 or less) capable of reducing, inhibiting or preventing the formation of mitochondrial reactive oxygen species to a subject in need thereof to reduce, inhibit or prevent the formation of mitochondrial reactive oxygen species.

Also provided is a method of reducing, inhibiting or preventing the formation of mitochondrial reactive oxygen species during and/or after exercise comprising the administration of an effective amount of a mitochondria targeting compound having a lipid affinity of less than 15% (such as a log P of −0.75 or less) capable of reducing, inhibiting or preventing the formation of mitochondrial reactive oxygen species to a subject in need thereof.

Further also provided is a method of enhancing muscle recovery during and/or after exercise comprising the administration of an effective amount of a mitochondria targeting compound having a lipid affinity of less than 15% (such as a log P of −0.75 or less) capable of reducing, inhibiting or preventing the formation of mitochondrial reactive oxygen species to a subject in need thereof.

The term "mitochondria-targeting compound" as used herein, refers to the ability of the compound to accumulate within mitochondria. For example, in the present invention, "mitochondria targeting compound" refers to a compound where about 0.5% or more, such as about 1% or more of about 2.5% of more of the compound accumulates within mitochondria after a 1 hour incubation. Typically, in the present invention, from about 0.5% to about 100%, such as from about 1% to about 80% or from about 2.5% to about 60% of the "mitochondria targeting compound" will accumulate within mitochondria after a 1 hour incubation. For example, from about 0.5% to about 10% or from about 1% to about 5% of the "mitochondria targeting compound" will accumulate within mitochondria after a 1 hour incubation.

The compound having a lipid affinity of less than 15% may be cationic, for example, the compound may be a cationic mitochondria targeting compound.

Therefore, the present invention may also provide a cationic compound, for example a cationic mitochondria targeting compound, having a lipid affinity of less than 15% (such as a log P of −0.75 or less) for use in reducing, inhibiting or preventing the formation of mitochondrial reactive oxygen species or may provide a cationic compound, for example a cationic mitochondria targeting compound, having a lipid affinity of less than 15% (such as a log P of −0.75 or less) capable of reducing, inhibiting or preventing the formation of mitochondrial reactive oxygen species for use in reducing, inhibiting or preventing the formation of mitochondrial reactive oxygen species.

The present invention also provides a method of reducing, inhibiting or preventing the formation of mitochondrial reactive oxygen species comprising the administration of a cationic compound, for example a cationic mitochondria targeting compound, having a lipid affinity of less than 15% (such as a log P of −0.75 or less) or may provide a method of reducing, inhibiting or preventing the formation of mitochondrial reactive oxygen species comprising the administration of a cationic compound, for example a cationic mitochondria targeting compound, having a lipid affinity of less than 15% (such as a log P of −0.75 or less) capable of reducing, inhibiting or preventing the formation of mitochondrial reactive oxygen species.

The present invention may also provide the use of a cationic compound, for example a cationic mitochondria targeting compound, having a lipid affinity of less than 15% (such as a log P of −0.75 or less) in the manufacture of a medicament for reducing, inhibiting or preventing the formation of mitochondrial reactive oxygen species or may provide the use of a cationic compound, for example a cationic mitochondria targeting compound, having a lipid affinity of less than 15% (such as a log P of −0.75 or less) capable of reducing, inhibiting or preventing the formation of mitochondrial reactive oxygen species in the manufacture of a medicament for reducing, inhibiting or preventing the formation of mitochondrial reactive oxygen species.

The present invention also provides the use (for example, the non-therapeutic use) of a cationic compound, for example a cationic mitochondria targeting compound, having a lipid affinity of less than 15% (such as a log P of −0.75 or less) for reducing, inhibiting or preventing the formation of mitochondrial reactive oxygen species, for example, in-vitro or may provide the use (for example, the non-therapeutic use) of a cationic compound, for example a cationic mitochondria targeting compound, having a lipid affinity of less than 15% (such as a log P of −0.75 or less) capable of reducing, inhibiting or preventing the formation of mitochondrial reactive oxygen species for reducing, inhibiting or preventing the formation of mitochondrial reactive oxygen species, for example, in-vitro.

The present invention may also provide a cationic compound, for example a cationic mitochondria targeting compound having a lipid affinity of less than 15% (such as a log P of −0.75 or less) for use in treating or preventing a pathological condition associated with increased levels of mitochondrial reactive oxygen species or may provide a cationic compound, for example a cationic mitochondria targeting compound having a lipid affinity of less than 15% (such as a log P of −0.75 or less) capable of reducing, inhibiting or preventing the formation of mitochondrial reactive oxygen species for use in treating or preventing a pathological condition associated with increased levels of mitochondrial reactive oxygen species.

The present invention also provides a method of treating or preventing a pathological condition associated with increased levels of mitochondrial reactive oxygen species comprising the administration of a cationic compound, for example a cationic mitochondria targeting compound, having a lipid affinity of less than 15% (such as a log P of −0.75 or less) or may provide a method of treating or preventing a pathological condition associated with increased levels of mitochondrial reactive oxygen species comprising the administration of a cationic compound, for example a cationic mitochondria targeting compound, having a lipid affinity of less than 15% (such as a log P of −0.75 or less) capable of reducing, inhibiting or preventing the formation of mitochondrial reactive oxygen species.

The present invention may also provide the use of a cationic compound, for example a cationic mitochondria-targeting compound having a lipid affinity of less than 15% (such as a log P of −0.75 or less) in the manufacture of a medicament for treating or preventing a pathological condition associated with increased levels of mitochondrial reactive oxygen species or may provide the use of a cationic compound, for example a cationic mitochondria targeting compound having a lipid affinity of less than 15% (such as a log P of −0.75 or less) capable of reducing, inhibiting or preventing the formation of mitochondrial reactive oxygen species in the manufacture of a medicament for treating or preventing a pathological condition associated with increased levels of mitochondrial reactive oxygen species.

The present invention may also provide a method of enhancing sports performance, comprising the administration of an effective amount of a cationic compound, for example a cationic mitochondria targeting compound, having a lipid affinity of less than 15% (such as a log P of −0.75 or less) or may provide a method of enhancing sports performance, comprising the administration of an effective amount of a cationic compound, for example a cationic mitochondria targeting compound, having a lipid affinity of less than 15% (such as a log P of −0.75 or less) capable of reducing, inhibiting or preventing the formation of mitochondrial reactive oxygen species to a subject in need thereof to reduce, inhibit or prevent the formation of mitochondrial reactive oxygen species.

Also provided is a method of reducing, inhibiting or preventing the formation of mitochondrial reactive oxygen species during and/or after exercise comprising the administration of an effective amount of a cationic compound, for example a cationic mitochondria targeting compound, having a lipid affinity of less than 15% (such as a log P of −0.75 or less) or a method of reducing, inhibiting or preventing the formation of mitochondrial reactive oxygen species during and/or after exercise comprising the administration of an effective amount of a cationic compound, for example a cationic mitochondria targeting compound, having a lipid affinity of less than 15% (such as a log P of −0.75 or less) capable of reducing, inhibiting or preventing the formation of mitochondrial reactive oxygen species to a subject in need thereof.

Further also provided is a method of enhancing muscle recovery during and/or after exercise comprising the administration of an effective amount of a cationic compound, for example a cationic mitochondria targeting compound, having a lipid affinity of less than 15% (such as a log P of −0.75 or less) or a method of enhancing muscle recovery during and/or after exercise comprising the administration of an effective amount of a cationic compound, for example a cationic mitochondria targeting compound, having a lipid affinity of less than 16% (such as a log P of −0.75 or less) capable of reducing, inhibiting or preventing the formation of mitochondrial reactive oxygen species to a subject in need thereof.

The compound having a lipid affinity of less than 15% may be an anti-oxidant, for example a (cationic) mitochondria-targeting anti-oxidant.

Therefore, the present invention may also provide a (cationic) anti-oxidant, for example a (cationic) mitochondria-targeting anti-oxidant, having a lipid affinity of less than 15% (such as a log P of −0.75 or less) for use in reducing, inhibiting or preventing the formation of mitochondrial reactive oxygen species or may provide a (cationic) anti-oxidant, for example a (cationic) mitochondria targeting anti-oxidant, having a lipid affinity of less than 15% (such as a log P of −0.75 or less) capable of reducing, inhibiting or preventing the formation of mitochondrial reactive oxygen species for use in reducing, inhibiting or preventing the formation of mitochondrial reactive oxygen species.

The present invention also provides a method of reducing, inhibiting or preventing the formation of mitochondrial reactive oxygen species comprising the administration of a (cationic) anti-oxidant, for example a (cationic) mitochondria targeting anti-oxidant, having a lipid affinity of less than 15% (such as a log P of −0.75 or less) or may provide a method of reducing, inhibiting or preventing the formation of mitochondrial reactive oxygen species comprising the administration of a (cationic) anti-oxidant, for example a (cationic) mitochondria targeting anti-oxidant, having a lipid affinity of less than 15% (such as a log P of −0.75 or less) capable of reducing, inhibiting or preventing the formation of mitochondrial reactive oxygen species.

The present invention may also provide the use of a (cationic) anti-oxidant, for example a (cationic) mitochondria targeting anti-oxidant, having a lipid affinity of less than 15% (such as a log P of −0.75 or less) in the manufacture of a medicament for reducing, inhibiting or preventing the formation of mitochondrial reactive oxygen species or may provide the use of a (cationic) anti-oxidant, for example a (cationic) mitochondria targeting anti-oxidant, having a lipid affinity of less than 15% (such as a log P of −0.75 or less) capable of reducing, inhibiting or preventing the formation of mitochondrial reactive oxygen species in the manufacture of a medicament for reducing, inhibiting or preventing the formation of mitochondrial reactive oxygen species.

The present invention also provides the use (for example, the non-therapeutic use) of a (cationic) anti-oxidant, for example a (cationic) mitochondria targeting anti-oxidant, having a lipid affinity of less than 15% (such as a log P of −0.75 or less) for reducing, inhibiting or preventing the formation of mitochondrial reactive oxygen species, for example, in-vitro or may provide the use (for example, the non-therapeutic use) of a (cationic) anti-oxidant, for example a (cationic) mitochondria targeting anti-oxidant, having a lipid affinity of less than 15% (such as a log P of −0.75 or less) capable of reducing, inhibiting or preventing the formation of mitochondrial reactive oxygen species for reducing, inhibiting or preventing the formation of mitochondrial reactive oxygen species, for example, in-vitro.

The present invention may also provide a (cationic) anti-oxidant, for example a (cationic) mitochondria targeting anti-oxidant having a lipid affinity of less than 15% (such as a log P of −0.75 or less) for use in treating or preventing a pathological condition associated with increased levels of mitochondrial reactive oxygen species or may provide a (cationic) anti-oxidant, for example a (cationic) mitochondria targeting anti-oxidant having a lipid affinity of less than 15% (such as a log P of −0.75 or less) capable of reducing, inhibiting or preventing the formation of mitochondrial reactive oxygen species for use in treating or preventing a pathological condition associated with increased levels of mitochondrial reactive oxygen species.

The present invention also provides a method of treating or preventing a pathological condition associated with increased levels of mitochondrial reactive oxygen species comprising the administration of a (cationic) anti-oxidant, for example a (cationic) mitochondria targeting anti-oxidant, having a lipid affinity of less than 15% (such as a log P of −0.75 or less) or may provide a method of treating or preventing a pathological condition associated with increased levels of mitochondrial reactive oxygen species comprising the administration of a (cationic) anti-oxidant, for example a (cationic) mitochondria targeting anti-oxidant, having a lipid affinity of less than 15% (such as a log P of −0.75 or less) capable of reducing, inhibiting or preventing the formation of mitochondrial reactive oxygen species.

The present invention may also provide the use of a (cationic) anti-oxidant, for example a (cationic) mitochondria targeting anti-oxidant having a lipid affinity of less than 15% (such as a log P of −0.75 or less) in the manufacture of a medicament for treating or preventing a pathological condition associated with increased levels of mitochondrial reactive oxygen species or may provide the use of a (cationic) anti-oxidant, for example a (cationic) mitochondria targeting anti-oxidant having a lipid affinity of less than 15% (such as a log P of −0.75 or less) capable of reducing, inhibiting or preventing the formation of mitochondrial reactive oxygen species in the manufacture of a medicament for treating or preventing a pathological condition associated with increased levels of mitochondrial reactive oxygen species.

The present invention may also provide a method of enhancing sports performance, comprising the administration of an effective amount of a (cationic) anti-oxidant, for example a (cationic) mitochondria targeting anti-oxidant having a lipid affinity of less than 15% (such as a log P of −0.75 or less) or may provide a method of enhancing sports performance, comprising the administration of an effective amount of a (cationic) anti-oxidant, for example a (cationic) mitochondria targeting anti-oxidant having a lipid affinity of less than 15% (such as a log P of −0.75 or less) capable of reducing, inhibiting or preventing the formation of mitochondrial reactive oxygen species to a subject in need thereof to reduce, inhibit or prevent the formation of mitochondrial reactive oxygen species.

Also provided is a method of reducing, inhibiting or preventing the formation of mitochondrial reactive oxygen species during and/or after exercise comprising the administration of an effective amount of a (cationic) anti-oxidant, for example a (cationic) mitochondria targeting anti-oxidant having a lipid affinity of less than 15% (such as a log P of −0.75 or less) or a method of reducing, inhibiting or preventing the formation of mitochondrial reactive oxygen species during and/or after exercise comprising the administration of an effective amount of a (cationic) anti-oxidant, for example a (cationic) mitochondria targeting anti-oxidant having a lipid affinity of less than 15% (such as a log P of −0.75 or less) capable of reducing, inhibiting or preventing the formation of mitochondrial reactive oxygen species to a subject in need thereof.

Further also provided is a method of enhancing muscle recovery during and/or after exercise comprising the administration of an effective amount of a cationic compound, for example a (cationic) anti-oxidant, for example a (cationic) mitochondria targeting anti-oxidant having a lipid affinity of less than 15% (such as a log P of −0.75 or less) or a method of enhancing muscle recovery during and/or after exercise comprising the administration of an effective amount of a (cationic) anti-oxidant, for example a (cationic) mitochondria targeting anti-oxidant having a lipid affinity of less than 15% (such as a log P of −0.75 or less) capable of reducing, inhibiting or preventing the formation of mitochondrial reactive oxygen species to a subject in need thereof.

The compound having a lipid affinity of less than 15% as defined above may be a compound of formula (I), or a pharmaceutically acceptable salt, derivative or salt of a derivative thereof, (I)

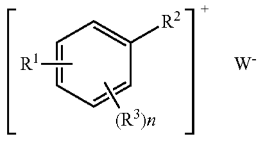

wherein, $R^1$ is —OH, $R^2$ is a cationic moiety, $W^-$ is a counterion, and each $R^3$ is independently H or $OR^4$, wherein $R^4$ is H or $C_{1-8}$ alkyl, preferably $C_{1-4}$ alkyl or $C_{1-2}$ alkyl and n is 0 to 4, preferably 2.

Pharmaceutically acceptable salts include acid addition salts and base addition salts. Such salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared using techniques known to those skilled in the art, such as by exchanging a counter-ion of a compound of the invention in the form of a salt with another counter-ion, for example using a suitable ion exchange resin.

Typically, the cationic moiety has a single positive charge. However, it is envisaged that the cationic moiety may have a charge of 2+ or 3+.

"Counterion" as used herein, refers to an anionic ion particle that is present to balance the charge of a corresponding oppositely charged molecule or atom. Examples of anionic counterions include inorganic or organic anions, such as halide-based anions, i.e. chloride, fluoride, bromide and iodide.

$R^2$ may be

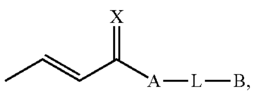

wherein X is O or S; A is O, NH; L is a linker group and B is a cationic group.

The linker may be a $C_{1-8}$ alkylene or alkenylene group, such as a $C_{1-4}$ alkylene or alkenylene group or a $C_{1-2}$ alkylene group.

B may be a cationic quaternary ammonium group, for example $N^+(R^5)_3$, wherein each $R^5$ is independently selected from H or $C_{1-8}$ alkyl, such as a $C_{1-4}$ or $C_{1-2}$ alkyl group.

For example, the compound of formula (I) may be a compound of formula (IA)

(IA)

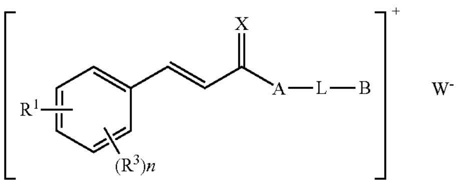

Wherein $R^1$, $R^3$, n, X, $W^-$, A, L and B are as defined above.

$R^1$ may be present in the meta or para position relative to the $R^2$ group. For example, $R^1$ may preferably be in the para position relative to the $R^2$ group.

Each $R^3$ may be in the ortho or meta position relative to the $R^2$ group. Typically, $R^3$ is in the meta position relative to the $R^2$ group.

The compound of formula (IA) may be:

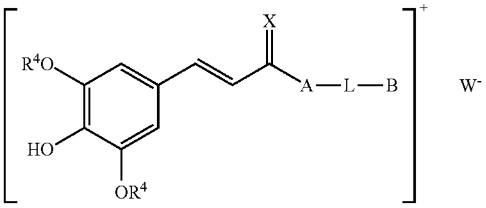

Wherein $R^4$, X, $W^-$, A, L and B are as defined above. For example, the compound of formula (IA) may be:

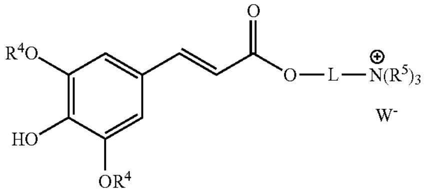

In certain aspects, the compound of formula (IA) may be:

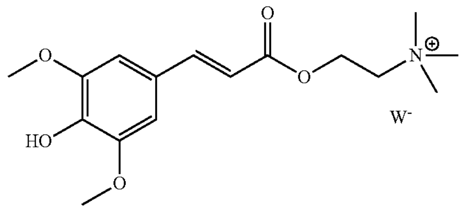

For example, the compound having a lipid affinity of less than 15% as defined above may be sinapine or a pharmaceutically acceptable salt, derivative or salt of a derivative thereof.

Thus, the present invention may also provide a compound of formula (I) or a pharmaceutically acceptable salt, derivative or salt of a derivative thereof (for example, sinapine, or a pharmaceutically acceptable salt, derivative or salt of a derivative thereof), for use in reducing, inhibiting or preventing the formation of mitochondrial reactive oxygen species. For example, the present invention may provide a mitochondria targeting compound of formula (I), (for example, sinapine, or a pharmaceutically acceptable salt, derivative or salt of a derivative thereof), for use in reducing, inhibiting or preventing the formation of mitochondrial reactive oxygen species, and/or may provide a compound of formula (I) or a pharmaceutically acceptable salt, derivative or salt of a derivative thereof (for example, sinapine, or a pharmaceutically acceptable salt, derivative or salt of a derivative thereof), capable of reducing, inhibiting or preventing the formation of mitochondrial reactive oxygen species for use in reducing, inhibiting or preventing the formation of mitochondrial reactive oxygen species.

The present invention may also provide a method of reducing, inhibiting or preventing the formation of mitochondrial reactive oxygen species comprising the administration of a compound of formula (I) or a pharmaceutically acceptable salt, derivative or salt of a derivative thereof (for example, sinapine, or a pharmaceutically acceptable salt, derivative or salt of a derivative thereof). For example, the present invention may provide a method of reducing, inhibiting or preventing the formation of mitochondrial reactive oxygen species comprising the administration of a mitochondria targeting compound of formula (I), (for example, sinapine, or a pharmaceutically acceptable salt, derivative or salt of a derivative thereof), and/or may provide a method of reducing, inhibiting or preventing the formation of mitochondrial reactive oxygen species comprising the administration of a compound of formula (I) or a pharmaceutically acceptable salt, derivative or salt of a derivative thereof (for example, sinapine, or a pharmaceutically acceptable salt, derivative or salt of a derivative thereof), capable of reducing, inhibiting or preventing the formation of mitochondrial reactive oxygen species.

The present invention may also provide the use of a compound of formula (I) or a pharmaceutically acceptable salt, derivative or salt of a derivative thereof (for example, sinapine, or a pharmaceutically acceptable salt, derivative or salt of a derivative thereof), in the manufacture of a medicament for reducing, inhibiting or preventing the formation of mitochondrial reactive oxygen species. For example, the present invention may provide the use of a mitochondria targeting compound of formula (I), (for example, sinapine, or a pharmaceutically acceptable salt, derivative or salt of a derivative thereof), in the manufacture of a medicament for reducing, inhibiting or preventing the formation of mitochondrial reactive oxygen species, and/or may provide the use of a compound of formula (I) or a pharmaceutically acceptable salt, derivative or salt of a derivative thereof (for example, sinapine, or a pharmaceutically acceptable salt, derivative or salt of a derivative thereof), capable of reducing, inhibiting or preventing the formation of mitochondrial reactive oxygen species in the manufacture of a medicament for reducing, inhibiting or preventing the formation of mitochondrial reactive oxygen species.

The present invention also provides the use (for example, the non-therapeutic use) of a compound of formula (I) or a pharmaceutically acceptable salt, derivative or salt of a derivative thereof (for example, sinapine, or a pharmaceutically acceptable salt, derivative or salt of a derivative thereof) for reducing, inhibiting or preventing the formation of mitochondrial reactive oxygen species, for example, in-vitro. For example, the present invention may provide the use (for example, the non-therapeutic use) of a mitochondria targeting compound of formula (I). (for example, sinapine, or a pharmaceutically acceptable salt, derivative or salt of a derivative thereof) for reducing, inhibiting or preventing the formation of mitochondrial reactive oxygen species, for example, in-vitro and/or may provide the use of a mitochondria targeting compound of formula (I), (for example, sinapine, or a pharmaceutically acceptable salt, derivative or salt of a derivative thereof) capable of reducing, inhibiting or preventing the formation of mitochondrial reactive oxygen species for reducing, inhibiting or preventing the formation of mitochondrial reactive oxygen species, for example, in-vitro.

The present invention may also provide a compound of formula (I) or a pharmaceutically acceptable salt, derivative or salt of a derivative thereof (for example, sinapine, or a pharmaceutically acceptable salt, derivative or salt of a derivative thereof), for use in treating or preventing a pathological condition associated with increased levels of mitochondrial reactive oxygen species. For example, the present invention may provide a mitochondria targeting compound of formula (I), (for example, sinapine, or a pharmaceutically acceptable salt, derivative or salt of a derivative thereof), for use in treating or preventing a pathological condition associated with increased levels of mitochondrial reactive oxygen species and/or may provide a compound of formula (I) or a pharmaceutically acceptable salt, derivative or salt of a derivative thereof (for example, sinapine, or a pharmaceutically acceptable salt, derivative or salt of a derivative thereof), capable of reducing, inhibiting or preventing the formation of mitochondrial reactive oxygen species for use in treating or preventing a pathological condition associated with increased levels of mitochondrial reactive oxygen species.

The present invention may also provide a method of treating or preventing a pathological condition associated with increased levels of mitochondrial reactive oxygen species comprising the administration of a compound of formula (I) or a pharmaceutically acceptable salt, derivative or salt of a derivative thereof (for example, sinapine, or a pharmaceutically acceptable salt, derivative or salt of a derivative thereof). For example, the present invention may provide a method of treating or preventing a pathological condition associated with increased levels of mitochondrial reactive oxygen species comprising the administration of a mitochondria targeting compound of formula (I), (for example, sinapine, or a pharmaceutically acceptable salt, derivative or salt of a derivative thereof), and/or may provide a method of treating or preventing a pathological condition associated with increased levels of mitochondrial reactive oxygen species comprising the administration of a compound of formula (I) or a pharmaceutically acceptable salt, derivative or salt of a derivative thereof (for example, sinapine, or a pharmaceutically acceptable salt, derivative or salt of a derivative thereof), capable of reducing, inhibiting or preventing the formation of mitochondrial reactive oxygen species.

The present invention may also provide the use of a compound of formula (I) or a pharmaceutically acceptable salt, derivative or salt of a derivative thereof (for example, sinapine, or a pharmaceutically acceptable salt, derivative or salt of a derivative thereof), in the manufacture of a medicament for treating or preventing a pathological condition associated with increased levels of mitochondrial reactive oxygen species. For example, the present invention may provide the use of a mitochondria targeting compound of formula (I), (for example, sinapine, or a pharmaceutically acceptable salt, derivative or salt of a derivative thereof), in the manufacture of a medicament for treating or preventing a pathological condition associated with increased levels of mitochondrial reactive oxygen species and/or may provide the use of a compound of formula (I) or a pharmaceutically acceptable salt, derivative or salt of a derivative thereof (for example, sinapine, or a pharmaceutically acceptable salt, derivative or salt of a derivative thereof), capable of reducing, inhibiting or preventing the formation of mitochondrial reactive oxygen species in the manufacture of a medicament for treating or preventing a pathological condition associated with increased levels of mitochondrial reactive oxygen species.

The present invention may also provide a method of enhancing sports performance, comprising the administration of an effective amount of a compound of formula (I) or a pharmaceutically acceptable salt, derivative or salt of a derivative thereof (for example, sinapine, or a pharmaceutically acceptable salt, derivative or salt of a derivative thereof). For example, the present invention may provide a method of enhancing sports performance, comprising the administration of an effective amount of a mitochondria targeting compound of formula (I), (for example, sinapine, or a pharmaceutically acceptable salt, derivative or salt of a derivative thereof) or may provide a method of enhancing sports performance, comprising the administration of an effective amount of a compound of formula (I) or a pharmaceutically acceptable salt, derivative or salt of a derivative thereof (for example, sinapine, or a pharmaceutically acceptable salt, derivative or salt of a derivative thereof), capable of reducing, inhibiting or preventing the formation of mitochondrial reactive oxygen species, to a subject in need thereof.

Also provided is a method of reducing, inhibiting or preventing the formation of mitochondrial reactive oxygen species during and/or after exercise comprising the administration of an effective amount of a compound of formula (I) or a pharmaceutically acceptable salt, derivative or salt of a derivative thereof (for example, sinapine, or a pharmaceutically acceptable salt, derivative or salt of a derivative thereof). For example, the present invention may provide a method of reducing, inhibiting or preventing the formation of mitochondrial reactive oxygen species during and/or after exercise comprising the administration of an effective amount of a mitochondria targeting compound of formula (I), (for example, sinapine, or a pharmaceutically acceptable salt, derivative or salt of a derivative thereof) or a method of reducing, inhibiting or preventing the formation of mitochondrial reactive oxygen species during exercise comprising the administration of an effective amount of a compound of formula (I) or a pharmaceutically acceptable salt, derivative or salt of a derivative thereof (for example, sinapine, or a pharmaceutically acceptable salt, derivative or salt of a derivative thereof), capable of reducing, inhibiting or preventing the formation of mitochondrial reactive oxygen species, to a subject in need thereof.

Further also provided is a method of enhancing muscle recovery during and/or after exercise comprising the administration of an effective amount of a compound of formula (I) or a pharmaceutically acceptable salt, derivative or salt of a derivative thereof (for example, sinapine, or a pharmaceutically acceptable salt, derivative or salt of a derivative thereof). For example, also provided is a method of enhancing muscle recovery during and/or after exercise comprising the administration of an effective amount of a mitochondria targeting compound of formula (I), (for example, sinapine, or a pharmaceutically acceptable salt, derivative or salt of a derivative thereof) or a method of enhancing muscle recovery during and/or after exercise comprising the administration of an effective amount of a compound of formula (I) or a pharmaceutically acceptable salt, derivative or salt of a derivative thereof (for example, sinapine, or a pharmaceutically acceptable salt, derivative or salt of a derivative thereof), capable of reducing, inhibiting or preventing the formation of mitochondrial reactive oxygen species, to a subject in need thereof.

The compound having a lipid affinity of less than 15% as defined above may be obtained from or obtainable from a plant of the Brassicaceae family For example, the compound having a lipid affinity of less than 15% as defined above may be in the form of an extract obtained from or obtainable from a plant of the Brassicaceae family.

For example, the compound having a lipid affinity of less than 15% may be a compound or an extract obtained from or obtainable from *Brassica napus* (rapeseed).

The extract may be an aqueous extract, an alcoholic extract or a hydro-alcoholic extract. Preferably, the extract is a hydro-alcoholic extract, such as a hydro-methanolic or hydroethanolic extract. For example, the extract of the invention may be a hydroethanolic extract obtained using an extraction solvent comprising from about 1 to about 99% ethanol in water, such as from about 30% to about 70% ethanol in water.

The term "aqueous extract" as used herein, refers to the extract obtained from or obtainable from *Brassica napus* (rapeseed) when the extraction from the plant has been performed using water as the only solvent.

The term "alcohol extract" as used herein, refers to the extract obtained from or obtainable from *Brassica napus* (rapeseed) when the extraction from the plant has been performed using alcohol as the only solvent. For example, 100% methanol and/or 100% ethanol.

The term "hydro-alcoholic extract" as used herein, refers to the extract obtained from or obtainable from *Brassica napus* (rapeseed) when the extraction from the plant has been performed using a mixture of water and alcohol. For example, from about 1% to about 99% alcohol (e.g. ethanol) in water, such an extract would be termed a hydroethanolic extract.

The extract may be obtained from or obtainable from *Brassica napus* (rapeseed) using separation techniques that select for the required extract, which may be determined by those skilled in the art.

Typically, the extract may be obtained by the extraction and isolation processes as generally described herein below, or routine modifications thereof.

For example, processes for extraction and/or isolation of the extract may comprise (or consist essentially/consist of) the following steps:

(i) extraction of *Brassica* napus (rapeseed) (which may be ground) by a suitable solvent;

(ii) evaporation of the solvent; and, if required (iii) purification of the extract (e g, by chromatography).

The part of the *Brassica napus* (rapeseed) used in the extraction process, may typically be the seeds of the plant. For example, the extract may be obtained from defatted rapeseed meal (extraction cake) which is obtained as a by-product during the extraction of rapeseed oil from rapeseeds.

The process for extraction and/or isolation of the extract may therefore include the step of extracting oil from the seeds of *Brassica napus* (rapeseed) to obtain defatted rapeseed meal (extraction cake) before step (i).

Typically, *Brassica napus* (rapeseed, i.e. in the form of an extraction cake) is ground into granules with a particle size in a range from about 0.1 mm to about 30 mm, to increase the surface area for the solvent to contact and to increase extraction efficiency.

Particular solvents that may be used in the extraction process include alcohols such as methanol or ethanol), and alcohol/water mixtures (such as mixtures of methanol and water or ethanol and water). For example, the extraction solvents can be water or a water-alcohol mixture (i.e. from about 1% to about 99% alcohol in water or from about 30% to about 70% alcohol in water). Particular alcohols that may be mentioned include ethanol (EtOH) and methanol (MeOH).

In particular embodiments, the extraction solvent may be an ethanol-water mix, such as from about 1% to about 99% or from about 30% to about 70% ethanol in water.

In one embodiment, the temperature of extraction is in a range of from about 20° C. to about 100° C. In a particular embodiment, the temperature for extraction is in a range of from about 50° C. to about 70° C.

Typically, the ratio of plant material to solvent mixture used in the extraction process varies from about 1:1 to about 1:10 on a gram to millilitre basis, such as from about 1:3 to about 1:8.

The incubation period (i.e. the period during which the plant material is in contact with the solvent) is typically from about 1 hours to about 24 hours.

After the plant materials and solvent have been incubated, the solvent is separated from residual plant material and the extraction composition is concentrated (i.e. the solvent is removed) until the extraction composition has a solid component.

Thus, the present invention may provide a compound having a lipid affinity of less than 15% as defined above, wherein the compound is obtained from or obtainable from a plant of the Brassicaceae family, for example, obtained or obtainable from *Brassica napus* (rapeseed).

The present invention may also provide a compound having a lipid affinity of less than 15% as defined above, wherein the compound is in the form of an extract obtained from or obtainable from a plant of the Brassicaceae family for example, obtained or obtainable from *Brassica napus* (rapeseed).

The present invention may also provide uses and methods as defined above, wherein the compound having a lipid affinity of less than 15% may be obtained from or obtainable from a plant of the Brassicaceae family and/or may be in the form of an extract obtained from or obtainable from a plant of the Brassicaceae family. For example, in the uses and methods defined above, the compound having a lipid affinity of less than 15% may be a compound or an extract obtained from or obtainable from *Brassica napus* (rapeseed).

The compound having a lipid affinity of less than 15% as defined above may be provided in the form of a nutraceutical formulation, a dietary or food product for humans or animals, a nutritional supplement, a sports supplement, a fragrance or flavouring, a pharmaceutical or veterinary formulation (which may also be referred to as a pharmaceutical or veterinary composition), functional food composition, such as a food, feed or pet food or a food, feed or pet food supplement, an oenological or cosmetic formulation, consisting of, consisting essentially of or comprising a compound having a lipid affinity of less than 15% as defined above and optionally a pharmaceutically or veterinary acceptable excipient or (functional) food acceptable ingredient, as appropriate.

Thus, the present invention also provides a nutraceutical formulation, a dietary or food product for humans or animals, a nutritional supplement, a sports supplement, a fragrance or flavouring, a pharmaceutical or veterinary formulation (which may also be referred to as a pharmaceutical or veterinary composition), functional food composition, such as a food, feed or pet food or a food, feed or pet food supplement, an oenological or cosmetic formulation, consisting of, consisting essentially of or comprising a compound having a lipid affinity of less than 15% as defined above (for example, the compound in the form of an extract obtained from or obtainable from a plant of the Brassicaceae family) for use in reducing, inhibiting or preventing the formation of mitochondrial reactive oxygen species.

Typically, in the uses and methods described herein the compound having a lipid affinity of less than 15%, the compound of formula (I) or extract obtained from or obtainable from a plant of the Brassicaceae family is present in the nutraceutical formulation, a dietary or food product for humans or animals, a nutritional supplement, a sports supplement, a fragrance or flavouring, a pharmaceutical or veterinary formulation (which may also be referred to as a pharmaceutical or veterinary composition), functional food composition, such as a food, feed or pet food or a food, feed or pet food supplement, an oenological or cosmetic formulation in an amount from about 0.5% by weight to about 100% by weight.

The present invention also provides a method of reducing, inhibiting or preventing the formation of mitochondrial reactive oxygen species comprising the administration of an effective amount of a nutraceutical formulation, a dietary or food product for humans or animals, a nutritional supplement, a sports supplement, a fragrance or flavouring, a pharmaceutical or veterinary formulation (which may also be referred to as a pharmaceutical or veterinary composition), functional food composition, such as a food, feed or pet food or a food, feed or pet food supplement, an oenological or cosmetic formulation, consisting of, consisting essentially of or comprising a compound having a lipid affinity of less than 15% as defined above (for example, the compound in the form of an extract obtained from or obtainable from a plant of the Brassicaceae family).

The present invention also provides the use of a nutraceutical formulation, a dietary or food product for humans or animals, a nutritional supplement, a sports supplement, a fragrance or flavouring, a pharmaceutical or veterinary formulation (which may also be referred to as a pharmaceutical or veterinary composition), functional food composition, such as a food, feed or pet food or a food, feed or pet food supplement, an oenological or cosmetic formulation, consisting of, consisting essentially of or comprising a compound having a lipid affinity of less than 15% as defined above (for example, the compound in the form of an extract obtained from or obtainable from a plant of the Brassicaceae family) in the manufacture of a medicament for reducing, inhibiting or preventing the formation of mitochondrial reactive oxygen species.

The present invention also provides a nutraceutical formulation, a dietary or food product for humans or animals, a nutritional supplement, a sports supplement, a fragrance or flavouring, a pharmaceutical or veterinary formulation (which may also be referred to as a pharmaceutical or veterinary composition), functional food composition, such as a food, feed or pet food or a food, feed or pet food supplement, an oenological or cosmetic formulation, consisting of, consisting essentially of or comprising the compound having a lipid affinity of less than 15% as defined above (for example, the compound in the form of an extract obtained from or obtainable from a plant of the Brassicaceae family) for use in treating or preventing a pathological condition associated with increased levels of mitochondrial reactive oxygen species.

The present invention also provides a method of treating or preventing a pathological condition associated with increased levels of mitochondrial reactive oxygen species comprising the administration of a nutraceutical formulation, a dietary or food product for humans or animals, a nutritional supplement, a sports supplement, a fragrance or flavouring, a pharmaceutical or veterinary formulation (which may also be referred to as a pharmaceutical or veterinary composition), functional food composition, such as a food, feed or pet food or a food, feed or pet food supplement, an oenological or cosmetic formulation, consisting of, consisting essentially of or comprising a compound having a lipid affinity of less than 15% as defined above (for example, the compound in the form of an extract obtained from or obtainable from a plant of the Brassicaceae family).

The present invention also provides the use of a nutraceutical formulation, a dietary or food product for humans or animals, a nutritional supplement, a sports supplement, a fragrance or flavouring, a pharmaceutical or veterinary formulation (which may also be referred to as a pharmaceutical or veterinary composition), functional food composition, such as a food, feed or pet food or a food, feed or pet food supplement, an oenological or cosmetic formulation, consisting of, consisting essentially of or comprising the compound having a lipid affinity of less than 15% as defined above (for example, the compound in the form of an extract obtained from or obtainable from a plant of the Brassicaceae family) in the manufacture of a medicament for treating or preventing a pathological condition associated with increased levels of mitochondrial reactive oxygen species.

In the uses and methods described herein the pathological condition associated with increased levels of mitochondrial reactive oxygen species may be selected from cancer, ischemic reperfusion injury, heart failure, peripheral artery diseases, hyperglycemia, diabetes, insulin resistance, neurodegenerative diseases, chronic obstructive pulmonary diseases, hypertension and inflammatory diseases.

The present invention also provides a method of enhancing sports performance, comprising the administration of an effective amount of a nutraceutical formulation, a dietary or food product for humans or animals, a nutritional supplement, a sports supplement, a fragrance or flavouring, a pharmaceutical or veterinary formulation, an oenological or cosmetic formulation consisting of, consisting essentially of or comprising a compound having a lipid affinity of less than 15% as defined above (for example, the compound in the form of an extract obtained from or obtainable from a plant of the Brassicaceae family) to a subject in need thereof to reduce, inhibit or prevent the formation of mitochondrial reactive oxygen species.

The present invention also provides a method of reducing, inhibiting or preventing the formation of mitochondrial reactive oxygen species during and/or after exercise comprising the administration of an effective amount of a nutraceutical formulation, a dietary or food product for humans or animals, a nutritional supplement, a sports supplement, a fragrance or flavouring, a pharmaceutical or veterinary formulation, an oenological or cosmetic formulation consisting of, consisting essentially of or comprising a compound having a lipid affinity of less than 15% as defined above (for example, the compound in the form of an extract obtained from or obtainable from a plant of the Brassicaceae family) to a subject in need thereof.

The present invention also provides a method of enhancing muscle recovery during and/or after exercise comprising the administration of an effective amount of a nutraceutical formulation, a dietary or food product for humans or animals, a nutritional supplement, a sports supplement, a fragrance or flavouring, a pharmaceutical or veterinary formulation, an oenological or cosmetic formulation consisting of, consisting essentially of or comprising a compound having a lipid affinity of less than 15% as defined above (for example, the compound in the form of an extract obtained from or obtainable from a plant of the Brassicaceae family) to a subject in need thereof.

As used herein, references to pharmaceutically or veterinary acceptable excipients may refer to pharmaceutically or veterinary acceptable adjuvants, diluents and/or carriers as known to those skilled in the art.

Food acceptable ingredients include those known in the art (including those also referred to herein as pharmaceutically acceptable excipients) and can be natural or non-natural, i.e. their structure may occur in nature or not. In certain instances, they can originate from natural compounds and be later modified (e.g. maltodextrin).

By "pharmaceutically or veterinary acceptable" we mean that the additional components of the composition are generally safe, non-toxic, and neither biologically nor otherwise undesirable. For example, the additional components are generally sterile and pyrogen free. Such components must be "acceptable" in the sense of being compatible with the extract of the invention and not deleterious to the recipients thereof. Thus, "pharmaceutically acceptable excipients" includes any compound(s) used in forming a part of the formulation that is intended to act merely as an excipient, i.e. not intended to have biological activity itself.

The skilled person will understand that the compound having a lipid affinity of less than 15% as defined above (for example, the compound in the form of an extract obtained from or obtainable from a plant of the Brassicaceae family) (e.g. in the form of compositions, such as pharmaceutical or veterinary compositions) may be administered to a patient or subject (e.g. a human or animal patient or subject) by any suitable route, such as by the oral, rectal, nasal, pulmonary, buccal, sublingual, transdermal, intracisternal, intraperitoneal, and parenteral (including subcutaneous, intramuscular, intrathecal, intravenous and intradermal) route.

In particular, the compound having a lipid affinity of less than 15% as defined above (for example, the compound in the form of an extract obtained from or obtainable from a plant of the Brassicaceae family) may be administered orally. In such instances, pharmaceutical or veterinary compositions according to the present invention may be specifically formulated for administration by the oral route.

Pharmaceutical or veterinary compositions for oral administration include solid dosage forms such as hard or soft capsules, tablets, troches, dragees, pills, lozenges, powders and granules. Where appropriate, they can be prepared with coatings such as enteric coatings, or they can be formulated so as to provide controlled release of the active ingredient, such as sustained or prolonged release, according to methods well known in the art.

Liquid dosage forms for oral administration include solutions, emulsions, aqueous or oily suspensions, syrups and elixirs.

Compositions (e.g. pharmaceutical or veterinary or food compositions) described herein, such as those intended for oral administration, may be prepared according to methods known to those skilled in the art, such as by bringing the components of the composition into admixture.

The compositions of the invention may contain one or more additional components as food ingredients or pharmaceutical components, such as sweetening agents, flavouring agents, colouring agents and preserving agents. The compositions of the invention may contain the active ingredient (s) in admixture with non-toxic pharmaceutically acceptable excipients (or ingredients) which are suitable for the manufacture of tablets. These excipients (or ingredients) may, for example, be: inert diluents, such as calcium carbonate, sodium carbonate, lactose, calcium phosphate or sodium phosphate; granulating and disintegrating agents, for example, corn starch, maltodextrin or alginic acid; binding agents, for example, starch, gelatine or acacia; and lubricating agents, for example magnesium stearate, stearic acid or talc.

If in a solid form, the compositions of the invention may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Suitable pharmaceutical or veterinary carriers include inert solid diluents or fillers, sterile aqueous solutions and various organic solvents. Examples of solid carriers are lactose, terra alba, sucrose, cyclodextrin, maltodextrin, dextrin, talc, gelatine, agar, pectin, acacia, magnesium stearate, magnesium hydroxide; stearic acid, arabic gum, modified starch and lower alkyl ethers of cellulose, saccharose, silicon dioxide. Examples of liquid carriers are syrup, vegetables oils, phospholipids, fatty acids, fatty acid amines, polyoxyethylene and water. Moreover, the carrier or diluent may include any sustained release material known in the art, such as glyceryl monostearate or glyceryl distearate, alone or mixed with a wax.

Moreover, the carrier or diluent may include any sustained release material known in the art, such as glyceryl monostearate or glyceryl distearate, alone or mixed with a wax.

The term "carrier" as used herein, may refer to a natural product or a product originating from nature that has been transformed or modified so that it is distinct from the natural product from which it originated.

In an aspect of the invention, the compound having a lipid affinity of less than 15% as defined above (for example, the compound in the form of an extract obtained from or obtainable from a plant of the Brassicaceae family) may be provided in a composition comprising maltodextrin and/or silicon dioxide.

Depending on the disorder, and the subject, to be treated, as well as the route of administration, the compound having a lipid affinity of less than 15% as defined above (for example, the compound in the form of an extract obtained from or obtainable from a plant of the Brassicaceae family) may be administered at varying doses (i.e. therapeutically effective doses, as administered to a patient in need thereof). In this regard, the skilled person will appreciate that the dose administered to a mammal, particularly a human, in the context of the present invention should be sufficient to effect a therapeutic response in the mammal over a reasonable timeframe. One skilled in the art will recognize that the selection of the exact dose and composition and the most appropriate delivery regimen will also be influenced by inter ala the pharmacological properties of the formulation, the nature and seventy of the condition being treated, and the physical condition and mental acuity of the recipient, as well as the age, condition, body weight, sex and response of the patient to be treated, and the stage/severity of the disease.

The pharmaceutical or veterinary or food compositions may comprise the compound having a lipid affinity of less than 15% as defined above (for example, the compound in the form of an extract obtained from or obtainable from a plant of the Brassicaceae family) in a therapeutically effective amount. As used herein, the term "effective amount" is synonymous with "therapeutically effective amount", "effective dose", or "therapeutically effective dose" and when used in reference to treating or preventing a pathological condition associated with increased levels of mitochondrial reactive oxygen species refers to the minimum dose of the extract of the invention necessary to achieve the desired therapeutic effect and includes a dose sufficient to reduce a symptom associated with a pathological condition associated with increased levels of mitochondrial reactive oxygen species. Effectiveness in treating a pathological condition associated with increased levels of mitochondrial reactive oxygen species can be determined by observing an improvement in an individual based upon one or more clinical symptoms, and/or physiological indicators associated with the condition. An improvement in a pathological condition associated with increased levels of mitochondrial reactive oxygen species also can be indicated by a reduced need for a concurrent therapy.

The appropriate effective amount of the compound having a lipid affinity of less than 15% as defined above (for example, the compound in the form of an extract obtained from or obtainable from a plant of the Brassicaceae family) to be administered to an individual for a particular a pathological condition associated with increased levels of mitochondrial reactive oxygen species can be determined by a person of ordinary skill in the art by taking into account factors, including, without limitation, the type of pathological condition associated with increased levels of mitochondrial reactive oxygen species, the location of the pathological condition associated with increased levels of mitochondrial reactive oxygen species, the cause of the pathological condition associated with increased levels of mitochondrial reactive oxygen species, the severity of the pathological condition associated with increased levels of mitochondrial reactive oxygen species, the degree of relief desired, the duration of relief desired, the particular dosage of the compound having a lipid affinity of less than 15% as defined above (for example, the compound in the form of an extract obtained from or obtainable from a plant of the Brassicaceae family) that is used, the rate of excretion of the compound having a lipid affinity of less than 15% as defined above (for example, the compound in the form of an extract obtained from or obtainable from a plant of the Brassicaceae family) used, the pharmacodynamics of the compound having a lipid affinity of less than 15% as defined above (for example, the compound in the form of an extract obtained from or obtainable from a plant of the Brassicaceae family) used, the nature of other compounds that may be included in the composition, the particular formulation, the particular route of administration, the particular characteristics, history and risk factors of the patient, such as, e.g., age, weight, general health and the like, or any combination thereof.

Additionally, where repeated administration of the compound having a lipid affinity of less than 15% as defined above (for example, the compound in the form of an extract obtained from or obtainable from a plant of the Brassicaceae family) is used, an effective amount of the compound having a lipid affinity of less than 15% as defined above (for example, the compound in the form of an extract obtained from or obtainable from a plant of the Brassicaceae family) will further depend upon factors, including, without limitation, the frequency of administration, the half-life of the extract of the invention, or any combination thereof.

In the use or method of the invention the compound having a lipid affinity of less than 15% as defined above may be administered in an amount of from about 100 mg/day to about 2000 mg/day, or from about 500 mg/day to about 1500 mg/day, or about 1000 mg/day. If the compound having a lipid affinity of less than 15% is administered in the form of an extract (such as an extract obtained or obtainable from a plant of the Brassicaceae family) or a nutraceutical formulation, a dietary or food product for humans or animals, a nutritional supplement, a sports supplement, a fragrance or flavouring, a pharmaceutical or veterinary formulation (which may also be referred to as a pharmaceutical or veterinary composition), functional food composition, such as a food, feed or pet food or a food, feed or pet food supplement, an oenological or cosmetic formulation consisting of, consisting essentially of or comprising the compound having a lipid affinity of less than 15%, the compound

25 having a lipid affinity of less than 15% would be present in an amount to provide the above dosages of extract. For example, the food composition may comprise from about 100 mg to about 2000 mg or from about 500 mg to about 1500 mg, or about 1000 mg of the extract of the invention and the pharmaceutical composition may comprise 10 mg. 20 mg. 30 mg. 40 mg, 50 mg, 60 mg, 70 mg, 80 mg, 100 mg, 250 mg, 500 mg, 1000 mg, 1500 mg or 2000 mg of the extract of the invention, such that the food composition or the pharmaceutical or veterinary composition may be administered one or more times per day in order to provide from about 100 mg to about 2000 mg/day or from about 500 mg to about 1500 mg/day, or about 1000 mg/day of the extract of the invention.

When included within a composition (e.g. a pharmaceutical or veterinary composition or a food composition), the compound having a lipid affinity of less than 15% as defined above (for example, the compound in the form of an extract obtained from or obtainable from a plant of the Brassicaceae family) is typically present in an amount from about 0.5% by weight to about 100% by weight, for example, from about 1% by weight to about 90% by weight or about 2% by weight to about 80% or from about 30% by weight to about 70% or from about 40% by weight to about 60% by weight.

Pharmaceutical or veterinary or food compositions of the invention may consist of or consist essentially of the compound having a lipid affinity of less than 15% as defined above (for example, the compound in the form of an extract obtained from or obtainable from a plant of the Brassicaceae family).

For the avoidance of doubt, in this specification when we use the term "comprising" or "comprises" we mean that the extract or composition being described must contain the listed ingredient(s) but may optionally contain additional ingredients. When we use the term "consisting essentially of" or "consists essentially of" we mean that the extract or composition being described must contain the listed ingredient(s) and may also contain small (for example up to 5% by weight, or up to 1% or 0.1% by weight) of other ingredients provided that any additional ingredients do not affect the essential properties of the extract or composition. When we use the term "consisting of" or "consists of" we mean that the extract or composition being described must contain the listed ingredient(s) only.

For the avoidance of doubt, preferences, options, particular features and the like indicated for a given aspect, feature or parameter of the invention should, unless the context indicates otherwise, be regarded as having been disclosed in combination with any and all other preferences, options particular features and the like as indicated for the same or other aspects, features and parameters of the invention.

The term "about" as used herein, e.g. when referring to a measurable value (such as an amount or weight of a particular component in the reaction mixture), refers to variations of ±20%, ±10%, ±5%, ±1%, ±0.5%, or, particularly, ±0.1% of the specified amount.

As detailed above, the compound having a lipid affinity of less than 15% (below a log P of –0.75) as defined above may be used for treating or preventing a pathological condition associated with increased levels of mitochondrial reactive oxygen species.

Pathological conditions associated with increased levels of mitochondrial reactive oxygen species, include, but are not limited to cancer, ischemic reperfusion injury, heart failure, peripheral artery diseases, hyperglycemia, diabetes,

26 insulin resistance, neurodegenerative diseases, chronic obstructive pulmonary diseases, hypertension and inflammatory diseases.

BRIEF DESCRIPTION OF THE FIGURES

FIG. 6. $H_2O_2$ and antimycin A-induced oxidative stress in cardiomyocytes. Cardiomyocytes were loaded with fluorogenic dyes sensitive to ROS production. $H_2$DCF-DA dye (A, B) probes $H_2O_2$ production within the cytosol, while dihydrorhodamine 123 ($DHR_{123}$) dye (C, D) probes $H_2O_2$ and peroxynitrite production within the mitochondria. Fluorescence was measured every 5 min and was normalized by the fluorescence baseline ($T_0$) (A, C). In control cells (basal), the fluorescence increases modestly during the 30 min-period. Some myocytes were incubated for one hour with either 6 µM of sinapine (SP[6]), 60 µM of sinapine (SP[60]) or 60 µM of sinapic acid (SAc[50]) prior to measurement. Some cells were stimulated with 0.1 mM $H_2O_2$ or with a mitochondrial electron transport chain complex III blocker, antimycin A (AA, 10 μM) to force mitochondria to produce ROS. The fluorescence in each condition was compared with control cells (basal) (B, D). Average fluorescence after 25 min. (n=4 animals) *, p<0.05 vs basal condition, ANOVA followed by Bonferroni's post-hoc test.

EXAMPLES

Figure 1:
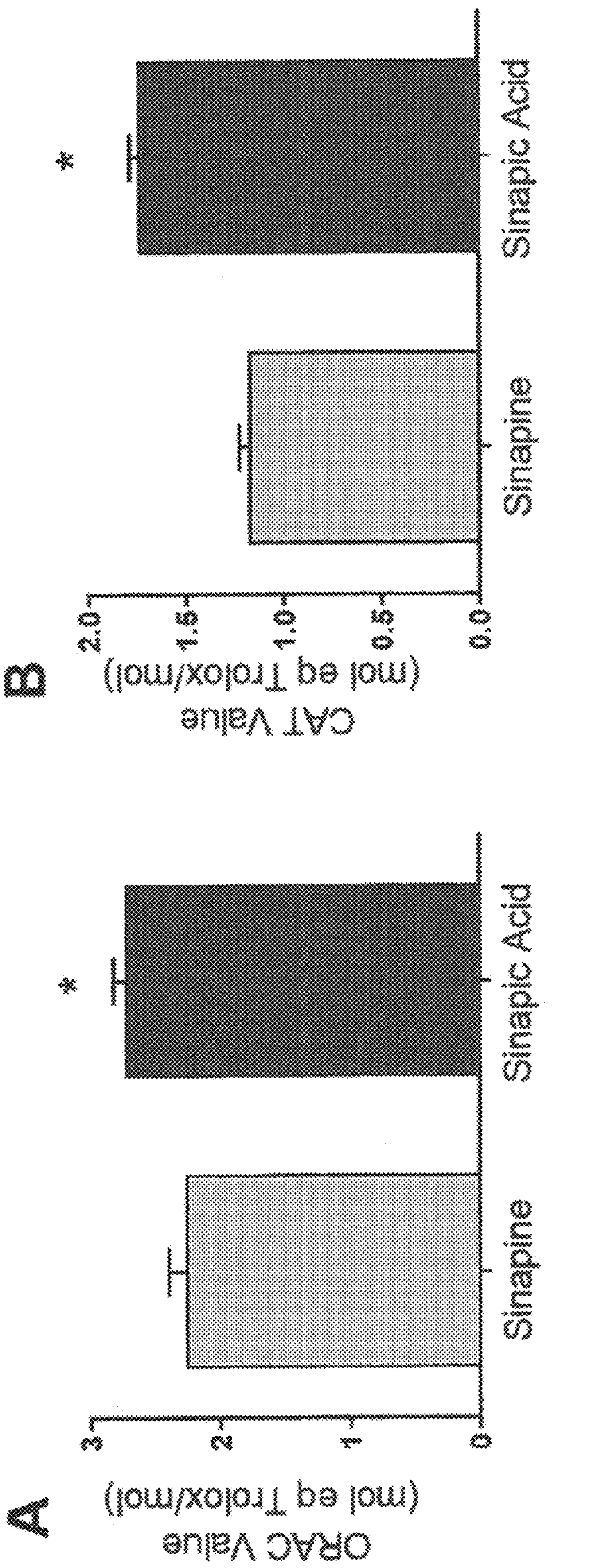
FIG. 1. Chemical antioxidant activity of sinapine and sinapic acid determined using the oxygen radical absorbance capacity (ORAC) and the conjugated autoxidizable triene (CAT) methods. * $p < 0.05$.

The present invention will be further described by reference to the following, non-limiting examples.

Material and Methods 1.1. Animal Studies.

Male Wistar rats (12-week-old, n=78; weight=361±4 g; Janvier. France) were housed with a 12-hour light-dark cycle and free access to water and food. All investigations conformed to the European Parliament Directive 2010/63/EU and were approved by the local ethics committee (Comite d'éthique pour l'expérimentation animale Languedoc-Roussillon, no CEEA-00322.03).

1.2. Antioxidant Activity Measurement Using the ORAC Assay

Experiments were conducted following the procedure of Ou et al. (Determination of total antioxidant capacity by oxygen radical absorbance capacity (ORAC) using fluorescein as the fluorescence probe: First Action 2012.23. JAOAC Int. 2013, 96, 1372-1376) wherein pure sinapine and sinapic acid are solubilized in 50:50 (v/v) acetone:water mixture. Dilutions were prepared in a phosphate buffer saline (PBS, 75 mM, pH 7.0) for each tested molecule. Twenty-five microliters of these solutions and PBS alone (blank) were transferred automatically into a 96-well microplate (BRAND. Germany). The plate was refrigerated (6° C.) before the sequence. After introducing the microplate in the reader (Infinite, Tecan. Switzerland), 150 μL of fluorescein solution (0.1 M) were added into each well. The plate was shaken for 8 s (2 mm amplitude) and incubated for 30 min at 37° C. After zero value measurement, 25 μL of APPH solution (152 mM) were added into each well, and the reaction kinetics was measured for 90 min every 90 s (60 measurements), corresponding to the decrease of fluorescein fluorescence (λex: 485 nm/λem: 535 nm). The antioxidant value of a molecule was calculated through the difference between the area under the curve of this sample and that of the blank (without antioxidant). The result of this operation gave the net area under the curve (AUC) which was then plotted on a graph as a function of the concentration. Only the linear part of the curve was considered to calculate the slope which was then divided by the slope of the Trolox (standard) calculated in the same conditions and analyzed on the same microplate. As such, ORAC values were expressed as mol Trolox equivalent/mol of molecule.

1.3. Antioxidant Activity Measurement Using the CAT Assay

These experiments were conducted following the procedure of Laguerre et al. (Conjugated autoxidizable triene (CAT) assay: a novel spectrophotometric method for determination of antioxidant capacity using triacylglycerol as ultraviolet probe. Anal. Biochem. 2008, 380, 282-290) wherein pure sinapine and sinapic acid were solubilized in 100 μL of DMSO and then in 50:50 (v/v) acetone water mixture at the desired concentration. Dilutions were then prepared in a phosphate buffer saline (PBS, 75 mM, pH 7.0) for each tested molecule. Fifty microliters of these solutions and PBS alone (blank) were transferred automatically into a 96-well microplate (Greiner, Austria). The plate was refrigerated (6° C.) before the sequence.

In parallel, to prepare the tung oil-in-water emulsion, twenty-five milliliters of PBS solution containing 34 μM Brij 35 (neutral emulsifier, estimated MW=1198 g/mol) was added to 8 mg tung oil in a brown glass flask. It is crucial to premix this mixture by stirring it for 10 s using a Vortex apparatus, before its homogenization in an Ultra Turrax homogenizer (Janke & Kunkel, Staufen, Germany) at approximately 2400 rpm for 90 seconds.

After introducing the microplate in the reader (Infinite, Tecan, Switzerland) and 4 min incubation at 37° C., 100 μL of tung oil-in-water emulsion (0.1 M) were added into each well.

The plate was shaken for 60 seconds (2 mm amplitude). Then, 50 μL of APPH solution (4 mM) were added into each well, and the reaction kinetics was measured for 120 min every 60 seconds (120 measurements), corresponding to the decrease of tung oil absorbance (at 280 nm).

The antioxidant value of a molecule was calculated through the difference between the area under the curve of this sample and that of the blank (without antioxidant). The result of this operation gave the net area under the curve (AUC) which was then plotted on a graph as a function of the concentration. Only the linear part of the curve was considered to calculate the slope which was then divided by the slope of the Trolox (standard) calculated in the same conditions and analyzed on the same microplate. As such, ORAC CAT values were expressed as mol Trolox equivalent/mol of molecule.

1.4. Log D (pH 7.0) Measurement

In a 10-mL glass tube, two milligrams of sinapine, sinapic acid or MitoTEMPO were added by 4 mL of a 75 mM $KH_2PO_4$ buffer solution (aqueous phase), and 4 mL of octan-1-ol. The mixture was then vortexed for 1 hour at room temperature and left to equilibrate for 30 min for sinapic acid and sinapine, and overnight for MitoTEMPO. Both phases were collected with a Pasteur pipette and extemporaneously analyzed by LC-MS using the procedure described below in section 2.7.

1.5. Isolated Cardiomyocytes

Ventricular cardiomyocytes were isolated from 200-250 g male adult Wistar rats as previously described (Cazorla et al. Transmural stretch-dependent regulation of contractile properties in rat heart and its alteration after myocardial infarction. FASEB J. 2005, 19, 88-90). The rats were anesthetized by i.p. injection of pentobarbital sodium (100 mg/kg) with heparin (100 U). The heart was rapidly excised, rinsed in ice-cold Hanks-HEPES buffer (in mM: NaCl 117, KCl 5.7. $NaHCO_3$ 4.4, $KH_2PO_4$ 1.5. $MgCl_2$ 1.7, HEPES 21, glucose 11.7, taurine 20. pH at 7.15) mounted on a Langendort perfusion system and perfused (3 mi/min, at 37° C.) first with a Hanks-HEPES buffer for 5 min to be cleared from blood, then with a buffer supplemented with 1.2 mg/mL collagenase type 4 (Worthington, Lakewood, N.J., USA) for 13-18 min. Small pieces of left ventricle were dissected and mechanically dissociated. The $Ca^{2+}$ concentration was gradually increased to 1 mM $Ca^{2+}$ and cells were used within the day. Experiments were performed in Tyrode solution with 1.8 mM $Ca^{2+}$.

1.6. Fluorimetric Detection of Intracellular Sinapine

Entry of sinapine (Fortochem Technology Limited, Hong Kong) in the cardiomyocytes was measured using the autofluorescence of sinapine. Cardiomyocytes were maintained in laminin-coated petri dish on a microscope stage (Axiovert, Zeiss, Germany; 20× objective). Cells were illuminated at 340 nm using a lambda DG-4 excitation system (Sutter Instrument Company, CA, USA). Images were captured digitally every 0.35 sec with a cooled CCD camera (Photometrics, Roper scientific, France) at 450 nm emission. Changes in fluorescence after correction for background (Metafluor software, Universal Imaging Corporation, USA).

1.7. HPLC Quantification of Cytosolic and Mitochondrial Levels of Sinapine and Sinapic Acid Antioxidants were also quantified in cardiomyocytes using LC-MS/MS. Cardiomyocytes (100,000 cells/mL) were incubated in Tyrode for 1 or 2 h with different concentrations of sinapine (2, 20, and 60 μM) or sinapic acid (Sigma Aldrich, 2, 20, and 60 μM). Extracellular, cytosolic and mitochondrial fractions were obtained and frozen in liquid nitrogen until HPLC measurement. After incubation, cells were sedimented and the supernatant collected for the extracellular fraction. The pellet of cells was rinsed twice in Tyrode. Cells were incubated with PBS containing digitonine (5 mg/mL) for 10 min on ice. Cells were centrifugated at 10,000 g for 20 min at 4° C., and the supernatant consisting in the cytosolic fraction was collected. The mitochondrial fraction was collected after rinsing five times the pellets in PBS to avoid contamination of the cytosolic fraction.

These different fractions were then analyzed using an Agilent Poroshell EC-C18 120, 2.7 microns, 2.1×150 mm analytical column on an Agilent 1290 Infinity II series pump. Injection volume was 1 μL. HPLC flow rate was 0.3 mL/min with the following mobile phases: water with 0.1% formic acid (A) and acetonitrile with 0.1% formic acid (B). The gradient was as follows: 0.0-3.0 min 0-30% B, 3.0-7.0 min 30-60% B, then a stabilization step of 4 min at the initial condition. Autosampler tray temperature was set to 10° C. and column temperature was set to 25° C. Detection was performed with an Agilent 6420 triple quadrupole in positive ionization mode with ESI source, gas temperature 325° C., gas flow 9 L/min, nebulizer 35 psi, and capillary voltage 3500 V. Mass spectrometer was working in MRM mode acquisition following the specific transition for Isoproturon-d3 (internal standard 210.2→75.0), Sinapine 310.2→251.1 (qualifier 175.0 and 91.0) and Sinapic acid 225.1→207.0 (qualifier 91.0 and 65.0).

1.8. Antioxidant Activity of Sinapine and Sinapic Acid in Cardiomyocytes

Cardiomyocytes (30,000 cell/mL) were incubated with sinapine or sinapic acid for 1 h. Thirty minutes before the end, a fluorogenic probe was added. We used dihydrorhodamine 123 ($DHR_{123}$) to probe mitochondrial $H_2O_2$ and peroxynitrites (Invitrogen Molecular probes Fischer scientific, D23806, Ex/Em: 508/529 nm, concentration=5 μM) and 2',7'-dichlorodihydrofluorescein diacetate ($H_2$DCF-DA) to probe cytosolic $H_2O_2$(Invitrogen Molecular probes Fischer scientific, D399 Ex/Em: 492/517 nm, concentration=5 μM). Cells were rinsed with a Tyrode solution and distributed in microplates for the various conditions. Some cells were stimulated with 0.1 mM $H_2O_2$(Sigma Aldrich) or with a 10 μM complex III blocker, antimycin A (AA, Sigma Aldrich) to force the cell to produce mitochondrial ROS. The microplate was immediately transferred to the microplate reader Tecan Infinite M200Pro. Fluorescence was measured at the different wavelengths every 5 min for 30 min.

1.9. Ischemia-Reperfusion (IR) on Isolated Hearts

Briefly, animals were anaesthetized (sodium pentobarbital, 120 mg/kg, i.p.), a thoracotomy was performed, the heart was removed and perfused retrogradely using a Langendorff apparatus. Hearts were paced at a rate of 300 beats/min (Low voltage stimulator, BSL MP35 SS58L, 3V) and a non-compliant balloon was inserted into the left ventricle (LV) to monitor the LV pressure. Hearts were stabilized for 20 min, perfused for 45 min with or without sinapine (60 μM), sinapic acid (60 μM) or MitoTEMPO (Sigma Aldrich, 0.1 μM), then subjected to global no-flow ischemia for 20 min, followed by 10 min of reperfusion. During the entire IR procedure, cardiac functional parameters such as LV developed pressure (LVDP) were recorded (MP35, BioPac System Inc) and coronary effluents were collected to evaluate coronary blood flow. After 10 min of post-ischemic reperfusion (Reperfusion), hearts were quickly removed, the right ventricle cleaned and LV samples frozen in liquid nitrogen for biochemical analysis or embedded in Optimal Cutting Temperature (OCT from Tissue-Tek) and flash-frozen in liquid nitrogen.

1.10. Measurements of ROS Production by Dihydroethidium (DHE) Staining

LV samples were embedded in Optimal Cutting Temperature (OCT from Tissue-Tek) and flash-frozen in liquid nitrogen. Frozen sections were covered with 10 μM DHE and incubated in alight-protected humidified chamber at 37° C. for 5 min. Images were obtained with a fluorescence microscope (Olympus BX60, Excitation: 488 nm; emission: 610 nm) at the Imaging facility 3A INRA/University of Avignon. SOD-mimetic TEMPOL (10 mM, Santa Cruz Biotechnology) was used as a negative control to confirm that the signals resulted from ROS production.

1.11. Sinapine Bioavailability

To evaluate plasmatic and tissular bioavailability of sinapine, rats received 200 mg/kg of sinapine by oral gavage. Blood samples were collected 15, 30, 60 and 120 min after sinapine administration from the right jugular vein. Sinapine and sinapic acid were then quantified in plasma using the following procedure: plasma (50 μL) is mixed with internal standard solution (50 μL in methanol at 10 ng/mL) and mix on a vortex for 1 minute. The solution is then centrifuge for 3 minutes at 12000 rpm, and the supernatant injected into HPLC/MS for quantification. At the end of the procedure the animals were sacrificed and hearts quickly removed. The right ventricle cleaned and LV samples frozen in liquid nitrogen. LV tissue was homogenized in 2 mL of mitochondria isolation buffer (pH 7.2; in mM: 300 saccharose, 5 TES. 0.2 EGTA), using a Polytron (Ultra Turrax T25, IKA Labortechnik). The homogenate was centrifugated at 1,000 g for 10 min at 4° C. To separate cytosolic fraction from the mitochondrial one, the supernatant was centrifugated at 12,000 g for 15 min to 4° C., then collected (cytosolic fraction), while the pellet was collected for mitochondria fraction. To optimize the release of mitochondria materials, the pellet was homogenized in 2% Triton-X lysis buffer during 10 min on ice. To remove Triton-X, mitochondrial fraction was washed, then centrifuged (12,000 g for 15 min at 4° C.) and the pellet was resuspended in mitochondria isolation buffer. Cytosolic and mitochondria fraction obtained were quickly frozen in liquid nitrogen until HPLC measurement. To do so, mitochondria was extracted with the same procedure as for plasma procedure. Cytosol (50 μL) was pipetted into 10 mL volumetric flask, spiked successively with internal standard solution (200 μL at 250 ng/mL in methanol) and 5 mL of methanol-water (50/50 v:v). The flask was ultrasonicated for 5 min, and once cooled down, completed to 10 mL with methanol-water (50/50 v:v). Both the mitochondrial and the cytosolic fractions were analyzed with the LC-MS/MS procedure described above.

1.12. Statistical Analysis.

Statistics were performed using StatView 5.0 (SAS Institute, Cary, N.C.). Data are presented as the mean±SEM. Differences were assessed with the one-way ANOVA when appropriate. When significant interactions were found, a Bonferroni post hoc test was applied with $p<0.05$. Some statistics were performed in a R programming environment (R Core Team R: a language and environment for statistical computing. Vienna, Austria. R Foundation for Statistical Computing; 2016. Available from: https://www.R-project.org/) using a linear mixed effect model via nlme package (Aarts et al. A solution to dependency: using multilevel analysis to accommodate nested data. Nat. Neurosci. 2014, 17, 491-496).

EXAMPLES

Example 1. Chemical Antioxidant Activity of Sinapine and Sinapic Acid

The chemical potential of sinapine (cationic) and sinapic acid (lacking the cationic moiety) for reducing peroxyradicals—i.e. their antioxidant activity—was measured using two methods known from the person skilled in the art: the radical oxygen absorbance capacity (ORAC) assay as described by Ou et al. (Determination of total antioxidant capacity by oxygen radical absorbance capacity (ORAC) using fluorescein as the fluorescence probe: First Action 2012.23. JAOAC Int. 2013, 96, 1372-1376) and the conjugated autoxidizable triene (CAT) assay as described by Laguerre et al. (Conjugated autoxidizable triene (CAT) assay: a novel spectrophotometric method for determination of antioxidant capacity using triacylglycerol as ultraviolet probe. Anal. Biochem. 2008, 380, 282-290).

In chemical media (aqueous solution, ORAC, and oil-in-water microemulsion, CAT) devoid of any living biological system, sinapine was systematically found less antioxidant than sinapic acid. Indeed, the ORAC and CAT values expressed in mol of Trolox equivalent per mol of compound were 2.28±0.25 (n=4) and 1.18 t 0.08 (n=3) for sinapine, respectively, and 2.73±0.176 (n=4) and 1.74±0.07 (n=3) for sinapic acid, respectively (FIG. 1).

The data highlights that the biological effects found in the next Examples cannot be inferred nor anticipated from their chemical potential.

Example 2. Lipid Affinity of Sinapine, Sinapic Acid, and Triphenylphosphonium-Based MitoTEMPO, MitoQ3, MitoQ3 and Mito Q10

The partition coefficient of sinapine, sinapic acid and MitoTEMPO (a commercially-available mitonchondria-targeting superoxide dismutase (SOD) mimetic) between two immiscible liquid phases (octan-1-ol and an aqueous solution at pH 7.0) was measured.

Figure 2:
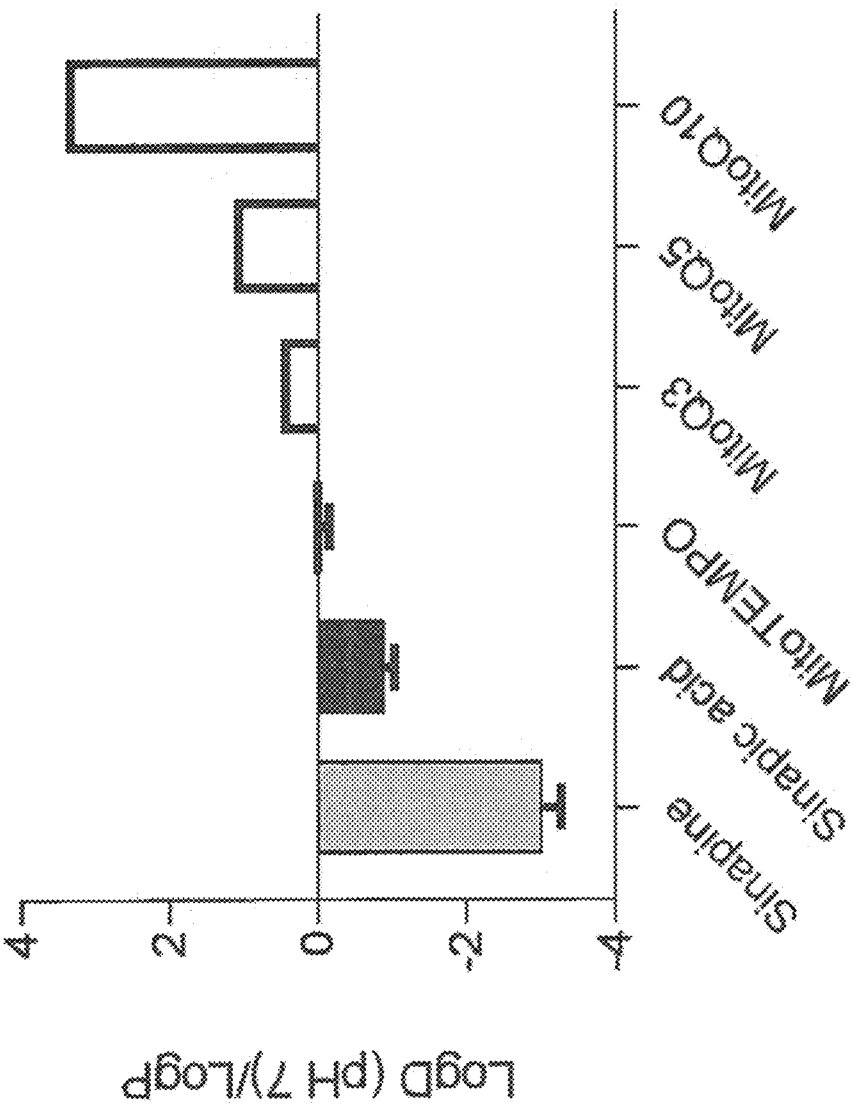
FIG. 2. Logarithm of the partition coefficient (log P) between octan-1-ol and water of sinapine, sinapic acid, MitoTEMPO, MitoQ3, MitoQ5, and MitoQ10. Values for the three latter compounds are available in literature (James et al. Interactions of mitochondria-targeted and untargeted ubiquinones with the mitochondrial respiratory chain and reactive oxygen species. J. Biol. Chem. 2005, 22, 21295-21312).

Sinapine partitions almost completely into water (log P–3.0, >99% in the aqueous phase), as well as sinapic acid, although in a much lesser extent (log P=–0.9; i.e. >85% in the aqueous phase) (FIG. 2). On the contrary, triphenylphosponium-based antioxidants such as MitoTEMPO. MitoQ3 (prior art), MitoQ5 (prior art), or MitoQ10 (prior art) only partition sparingly into the aqueous phase with a log D/log P (pH 7.0) of 0.0, 0.5, 1.1, and 3.4, respectively. For MitoTEMPO, a measured log D (pH 7.0) of 0.0 corresponds to a partitioning at 50/50% in both phases. It is considered here that a molecule with a high partition into the aqueous phase, hence a molecule with a negligible affinity for lipids, must partition less than 15% in the octan-1-ol phase, which corresponds to a log D/log P (pH 7.0) value above −0.75. Consequently, all considered triphenylphosponium-based antioxidants (MitoTEMPO, MitoQ3, MitoQ5, or MitoQ10) belong to the category of molecules having a significant lipid affinity, while sinapine and sinapic acid belongs to the category of molecules with no affinity for lipids. The log P values for compounds MitoQ3, MitoQ5, or MitoQ10 are given by James et al. (interactions of mitochondria-targeted and untargeted ubiquinones with the mitochondrial respiratory chain and reactive oxygen species. J. Biol. Chem. 2005, 22, 21295-21312).

Example 3. Sinapine Entry in Isolated Adult Cardiomyocytes in Rats

Figure 3B:
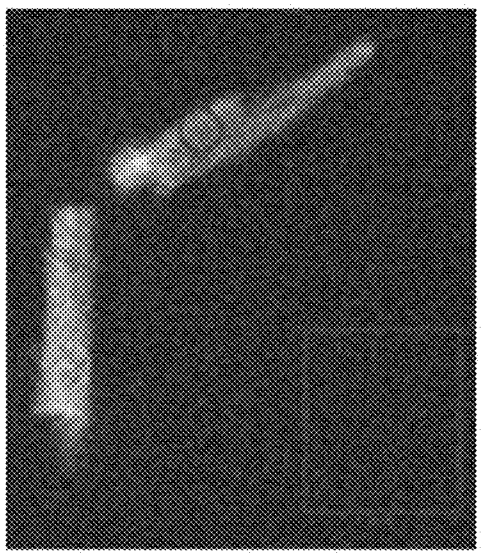
FIG. 3. Entry of sinapine in cardiomyocytes. (A) Fluorescence spectrum of sinapine ($\lambda_{max}$ Ex: 355 nm/$\lambda_{max}$ Em: 455 nm). (B) Measurement of autofluorescence of sinapine using Metafluor System (Ex 340 nm/Em 450 nm) within cardiomyocytes after subtraction of the background in the box 1 ($F_{kkg}$). (C-E) Example of the stability of fluorescence (Ex 340 nm/Em 450 nm) of two cardiomyocytes in absence of sinapine. (D) Increase of fluorescence (Ex 340 nm/Em 450 nm) in cardiomyocytes after a sinapine incubation (2 µM). (E) Fluorescence of individual control cells after 30 and 60 min (n=10 control cells, left panel, grey circles) and after incubation with 2 µM sinapine (n=41 cells, right panel, grey triangles). The average fluorescence of control (black circles) and sinapine (black triangles) incubated cardiomyocytes. *, $p < 0.05$, **, $p < 0.01$, ANOVA followed by Bonferroni's post-hoc tests.
Figure 3A:
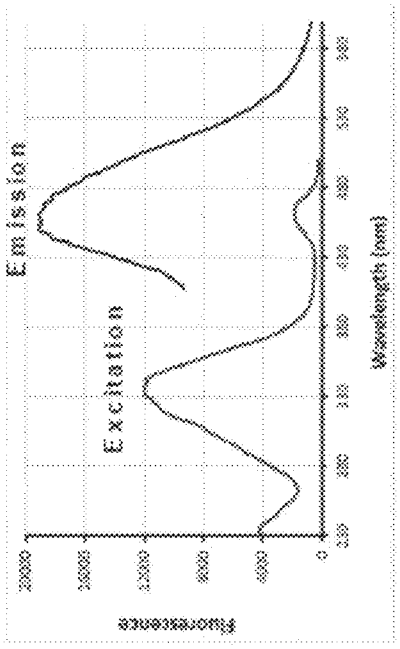
Figure 3E:
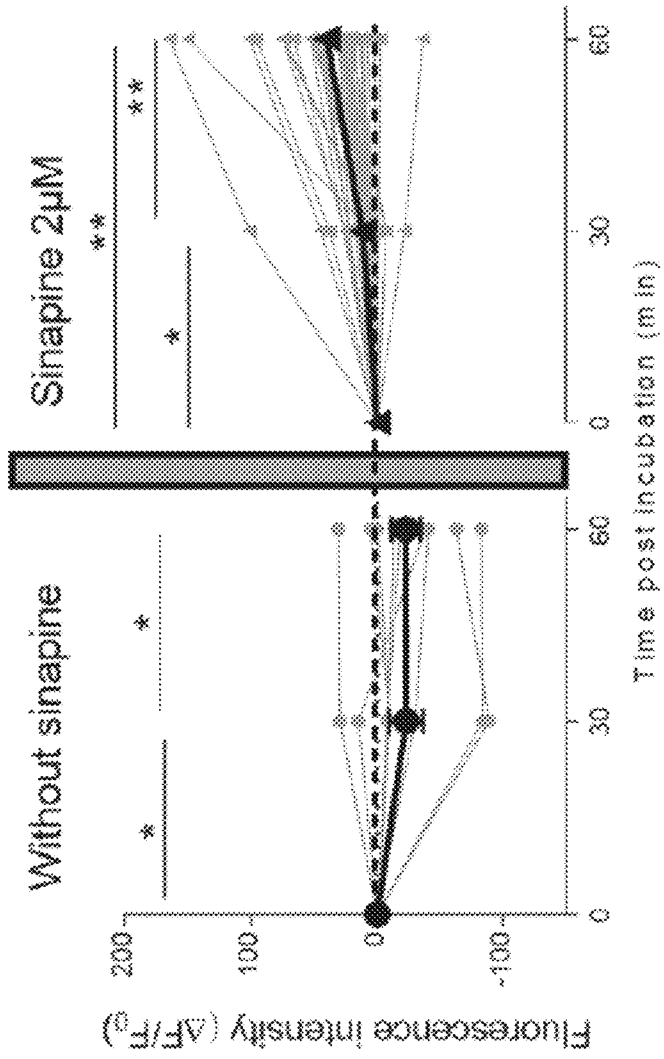

In this Example, we evaluated whether sinapine can enter in freshly isolated adult cardiomyocytes using its autofluorescence properties (355 nm excitation/450 nm emission) for the detection (FIG. 3A). After measuring the fluorescence every min for 1 h, the fluorescence decreases slightly with time in the control cells (FIG. 3C). For other cells, fluorescence was measured for 10 min to establish the baseline and then incubated with sinapine at low dose (2 μM). Fluorescence increased after 10-15 min demonstrating that sinapine was efficiently internalized into the cells (FIGS. 3D & E). The fluorescence further increased over the 1 h-period tested.

Example 4. Subcellular Partitioning of Sinapine and Sinapic Acid in Rat Cardiomyocytes To further evaluate if a positively charged moiety (such as choline) can endowed an antioxidant devoid of any lipid affinity with the ability to accumulate in mitochondria, we incubated sinapine and sinapic acid (lacking the choline group, i.e. negative control) in intact cardiomyocytes at three concentrations (2, 20, and 60 μM) for 1 or 2 h. Then, the mitochondrial fraction was separated from the cytosolic one using differential centrifugation. The levels of sinapine and sinapic acid were measured in each subcellular fraction using LC-MS/MS.

Figure 4:
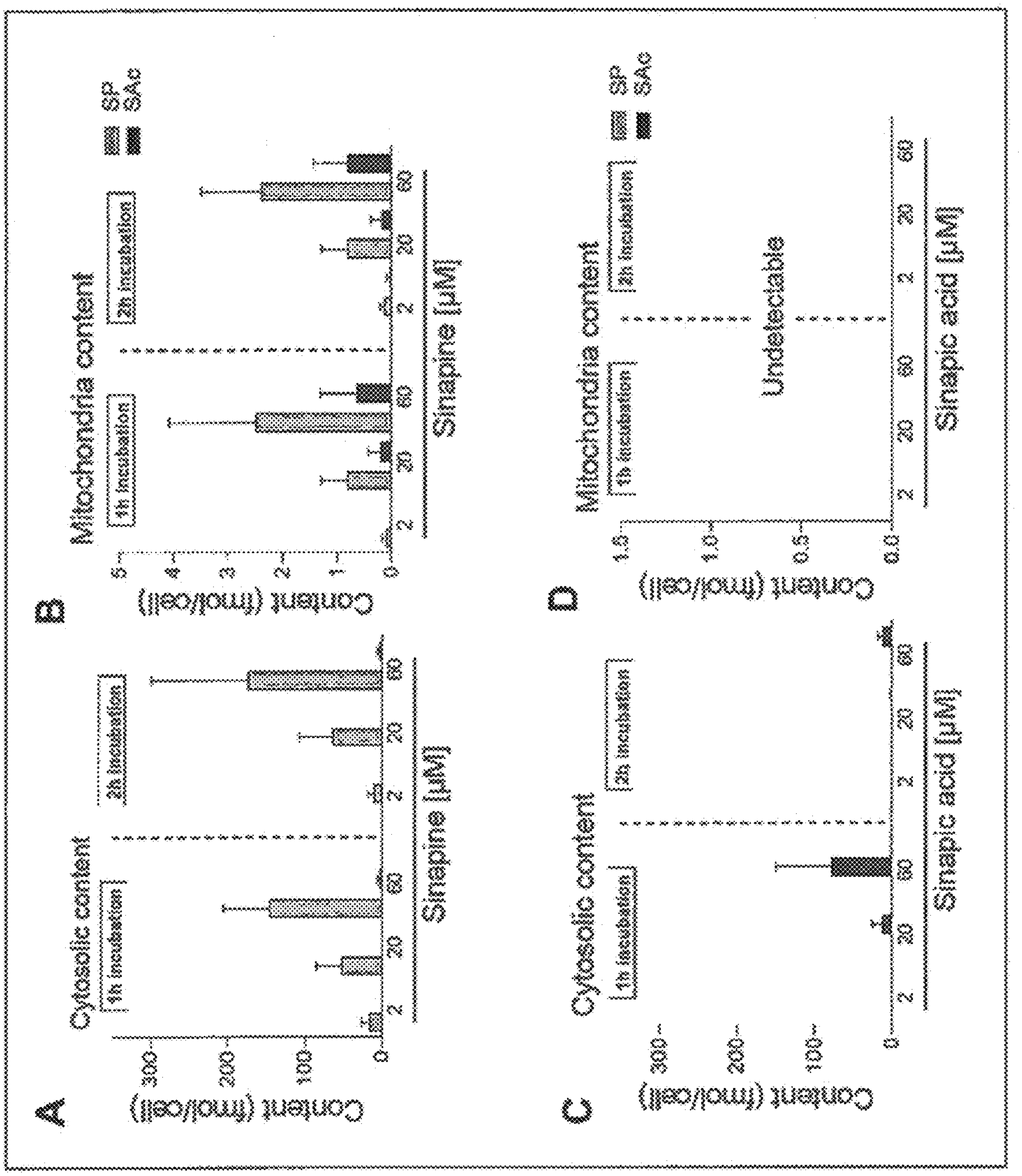
FIG. 4. Cytosol/mitochondria partitioning of sinapine and sinapic acid in cardiomyocytes. Myocytes were incubated for 1 (A, B) or 2 h (C, D) with different concentrations of sinapine or sinapic acid (2, 20, and 60 µM). After fractional separation, the amounts of sinapine and sinapic acid were measured by HPLC in the cytosol (A, C) or in isolated mitochondria (B, D) and were compared to a control without drug incubation. (n=6 experiments with sinapine, n=4 experiments with sinapic acid. *, $p < 0.05$ vs Ctrl, ANOVA followed by Bonferroni's post-hoc tests.

In cytosol, after one or two hours of sinapine incubation, we detected sinapine in a dose dependent manner (FIG. 4A), while sinapic acid was not detected, indicating no major sinapine hydrolysis. When sinapic acid was added to the medium, it entered the cardiomyocyte cytosol in a dose dependent manner particularly after 1 h (FIG. 4C). The level of sinapic acid in the cytosol was lower than that of sinapine. Logically, sinapine was not detected in the cytosolic fraction when cells were incubated with sinapic acid. The fact that no time-dependency of the incubation was found on cellular levels of sinapine and sinapic acid suggests that the entry of both molecules into cardiac cells is a rapid process taking place within an hour.

We also evaluated mitochondrial subfractions (FIGS. 48 and 0). After sinapine was incubated, it was detected in a dose-dependent manner in mitochondria, regardless of the incubation time (1 or 2 h). In this subfraction, we also detected sinapic acid, suggesting that approximately 25% of sinapine entering the mitochondria is hydrolyzed after 1 or 2 h. Interestingly, sinapic acid, which lacks the positively charged choline moiety, was not detected in mitochondria, regardless of incubation time and concentration.

Example 5. Mitochondria-Targeting of Orally Administered Sinapine in Rats

Figure 5:
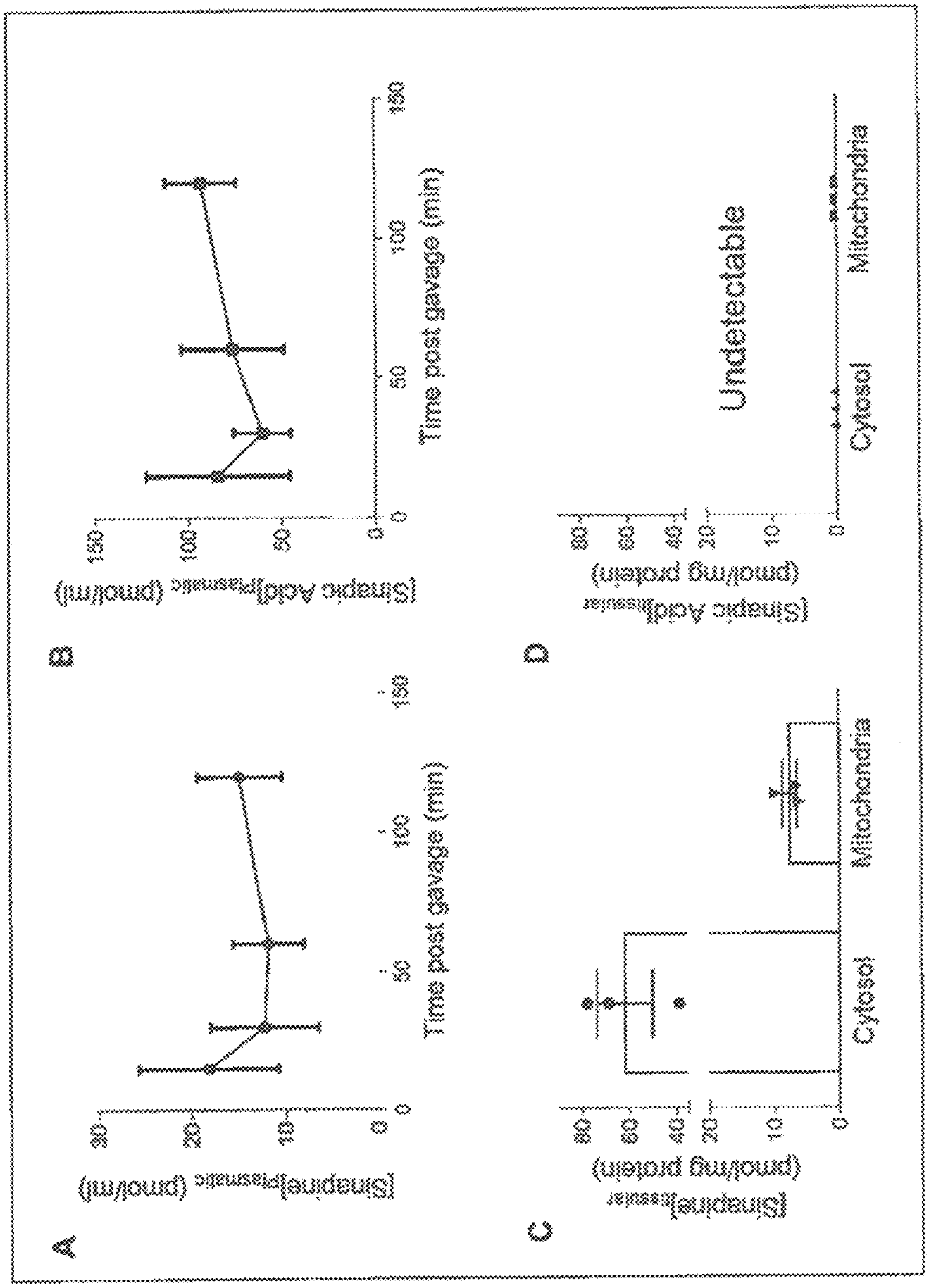
FIG. 5. Plasmatic and tissular levels of sinapine and sinapic acid after oral administration of sinapine (200 mg/kg). Blood samples were collected at 10, 30, 60 and 120 min after oral administration of sinapine. Plasmatic levels of sinapine (A) and sinapic acid (B) were measured by LC-MS-QQQ. At the end of the 120 min, the heart was removed, rinsed and frozen. Differential centrifugation was performed to separate the mitochondrial fraction from the cytosolic fraction. The level of sinapine (C) and sinapic acid (D) were measured in each cellular subfraction by LC-MS-QQQ (n=3 animals).

Using LC-MS-QQQ, we then measured plasmatic and tissular levels of sinapine and sinapic acid at 10, 30, 60, and 120 min after oral administration of sinapine (200 mg/kg) (Figures SA and SB). Both antioxidants were detected at all time points at a relatively stable level over the 2 h-period. Intriguingly, we found about five times more sinapic acid than sinapine in the plasma. After 120 min post-gavage, the heart was removed, rinsed and quickly frozen in liquid nitrogen. The concentrations of both antioxidants were determined in the cytosolic and mitochondrial fractions (FIGS. 5C and 5D). Unlike sinapic acid which was not found in any of the fractions (FIG. 5D), sinapine was detected and quantified in both the cytosol and mitochondria (FIG. 5C). Thus, sinapine administered orally is absorbed and is present in the blood stream, like sinapic acid, however, unlike this latter, sinapine is subsequently found in the cytosol and the mitochondria of cardiomyocytes; a subcellular distribution caused by the permanent positive charge provided to sinapine by the choline moiety.

Example 6. Antioxidant Activity of Sinapine Against Mitochondrial ROS Production in Isolated Rat Cardiomyocytes Considering the ability of a cationic antioxidant with no lipid affinity such as sinapine to accumulate within the mitochondrial subfraction, we evaluated the propensity of sinapine to limit mitochondrial ROS production in isolated adult rat cardiomyocytes during a stress (FIG. 6).

Two different ROS sensitive fluorogenic probes were used, $H_2$DCF-DA and $DHR_{123}$, which are specific of cytosolic and mitochondrial ROS production, respectively (Wei et al. Nitric oxide induces oxidative stress and apoptosis in neuronal cells. Biochim. Biophys. Acta-Mol. Cell Res. 2000, 1498, 72-79; Rego et al. Influence of the antioxidants vitamin E and idebenone on retinal cell injury mediated by chemical ischemia, hypoglycemia, or oxidative stress. Free Rad Biol. Med. 1999, 26, 1405-1417; Mark et al. Basic FGF attenuates amyloid β-peptide-induced oxidative stress, mitochondrial dysfunction, and impairment of Na+/K+-ATPase activity in hippocampal neurons. Brain Res. 1997, 756, 205-214).

Myocytes loaded with one of the probes were distributed in microplate wells. ROS production was determined by following the increase of fluorescence for 25 min. Fluorescence was measured every 5 min and was normalized by the baseline fluorescence (T0). Some cells were incubated with either sinapine (6 or 60 μM) or sinapic acid (60 μM) for 1 h prior measurement. After the incubations, cells were washed out. Some cells were stimulated with 0.1 mM $H_2O_2$ or with a mitochondrial electron transport chain complex III blocker, 10 μM antimycin A (AA) to force mitochondria to produce mitochondrial ROS (Quinlan et al. The mechanism of superoxide production by the antimycin-inhibited mitochondrial Q-cycle. J. Biol. Chem. 2011, 286, 31361-31372).

In control cells (basal), the fluorescence for both $H_2$DCF-DA and $DHR_{123}$ increases modestly within 25 min. Pre-incubations with sinapine or sinapic acid had no impact on the fluorescence level. In $H_2O_2$-stressed myocytes, $H_2$DCF-DA and $DHR_{123}$ fluorescences increased all along the 25 min-period. This indicates that treating cells with $H_2O_2$ leads to a cytosolic and mitochondrial ROS production. In contrast, in AA-stressed myocytes. $H_2$DCF-DA fluorescence did not vary, while that of $DHR_{123}$ increased continuously for 25 min, demonstrating that only mitochondrial ROS are produced when myocytes are incubated with AA. Therefore, we confirm in our experimental conditions the ability of $DHR_{123}$ to detect mitochondrial ROS.

Next to this, we pre-incubated cardiomyocytes with the two antioxidants before $H_2O_2$ or AA stress (FIG. 7). When a cytosolic oxidative stress was generated in presence of $H_2O_2$, both sinapine (6 and 60 μM) or sinapic acid (60 μM) prevented the increase in $H_2$DCF-DA (FIGS. 7A and 7B). This effect was dose-dependent for the sinapine. These results indicate that both sinapine and sinapic acid are efficient antioxidants under a global oxidative stress mediated by cytosolic ROS.

Figure 7B:
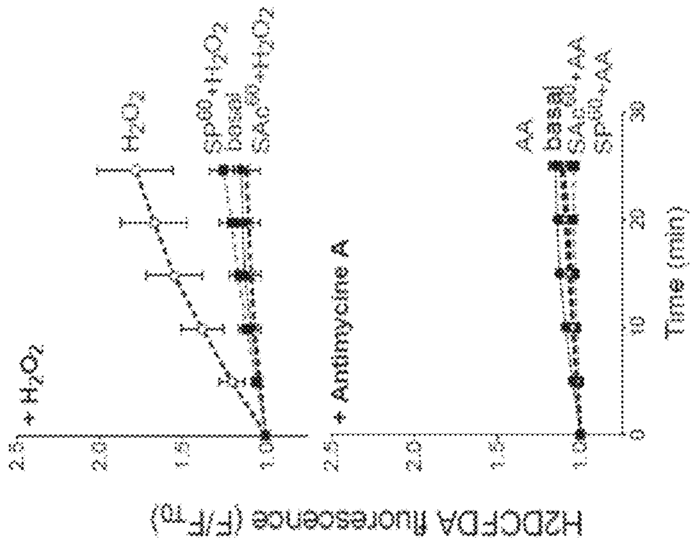
FIG. 7. Effect of sinapine and sinapic acid on $H_2O_2$ and antimycin A-induced oxidative stress in cardiomyocytes. Cardiomyocytes were loaded with fluorescent probes sensitive to ROS production. $H_2$DCF-DA (A, B) probes $H_2O_2$ production within the cytosol, while dihydrorhodamine 123 ($DHR_{123}$) (C, D) probes $H_2O_2$ and peroxynitrite production within the mitochondria. Fluorescence was measured every 5 min and was normalized by the fluorescence baseline (T0) (B, D). Cardiomyocytes were stimulated with 0.1 mM $H_2O_2$ or with a mitochondrial electron transport chain complex III blocker, antimycin A (AA, 10 μM) to force mitochondria to produce ROS. Some myocytes were incubated for one hour with either 6 μM of sinapine ($SP^6$), 60 μM of sinapine ($SP^{60}$) or 60 μM of sinapic acid ($SAc^{60}$) prior to $H_2O_2$ and AA stimulation. The fluorescence in each condition was compared with control cells (basal). (B, D) Average fluorescence after 25 min. (n=4 animals) *, p<0.05 vs basal condition, ANOVA followed by Bonferroni's post-hoc test.
Figure 7A:
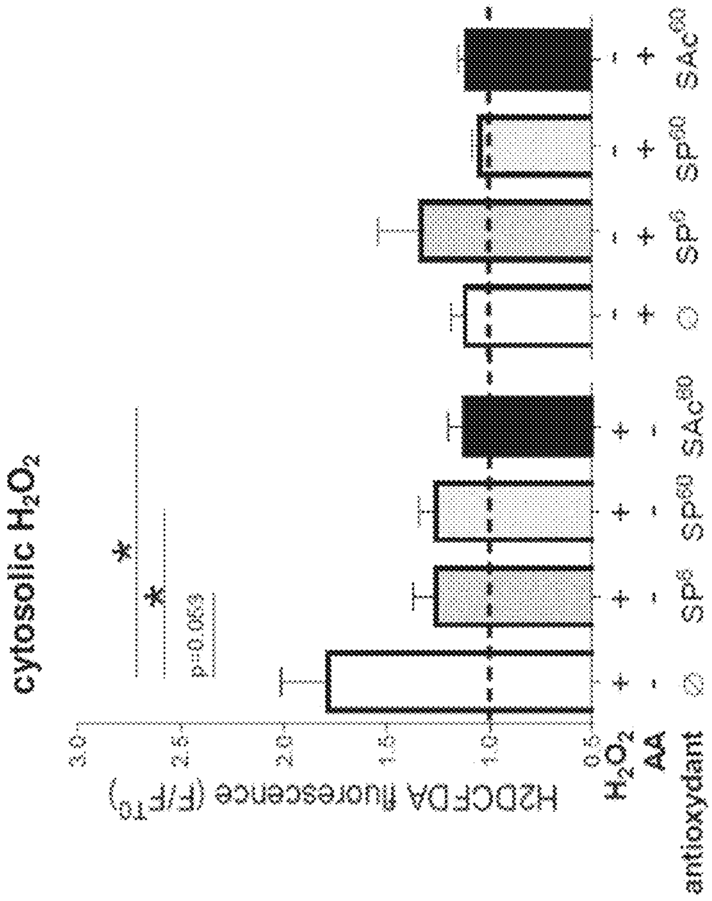
Figure 7D:
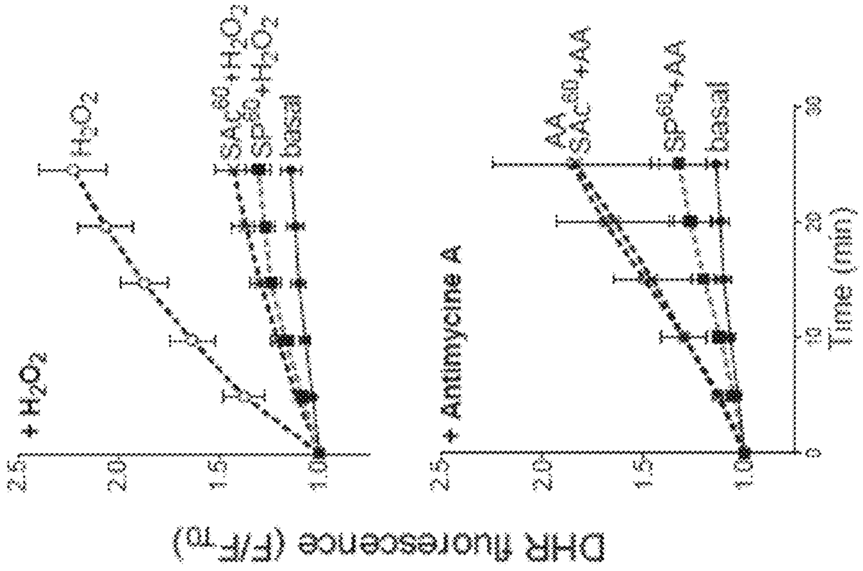
Figure 7C:
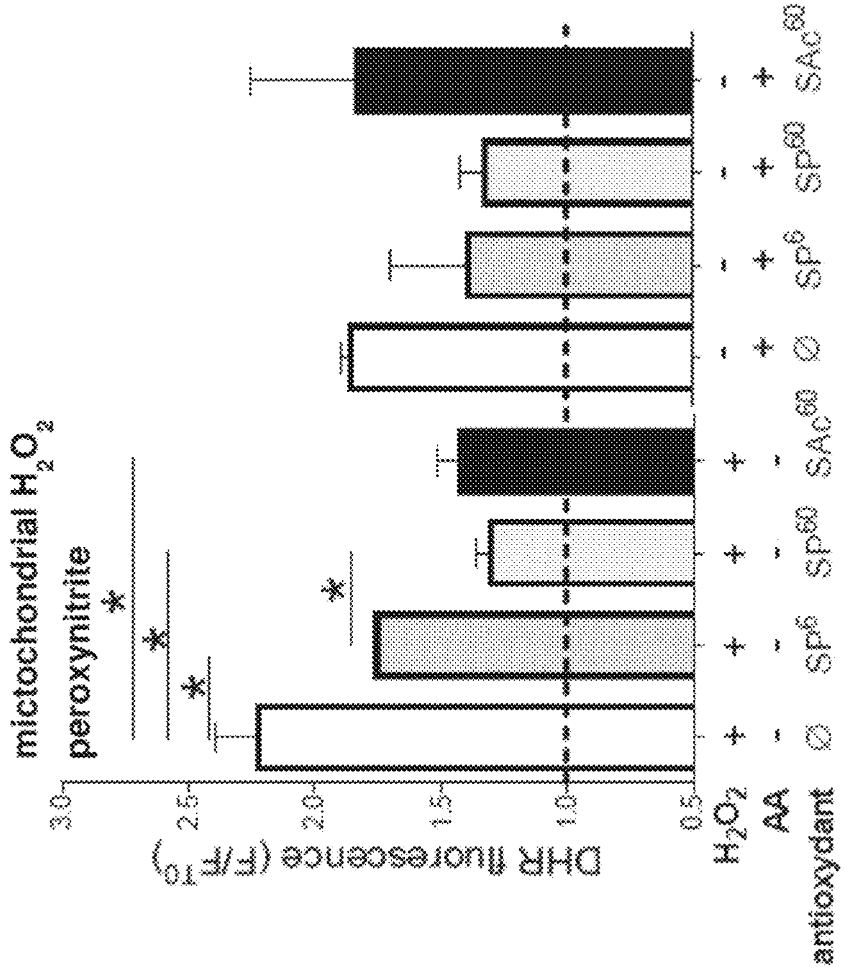

The AA conditions then allowed us to test the antioxidant capacity of sinapine and sinapic acid under a specific mitochondrial oxidative stress. In presence of AA, $H_2$DCF-DA fluorescence was not affected in any conditions, indicating no measurable cytosolic ROS production (FIGS. 7A and 7B). On the contrary, AA-induced increase in $DHR_{123}$ fluorescence was prevented by sinapine but not by sinapic acid pre-treatments (FIGS. 7C and 7D). While both antioxidants are able to scavenge cytosolic ROS, these last results clearly demonstrate that only sinapine was able to target mitochondrial ROS.

Example 7. Differential Cardioprotective Impact of Sinapine and Sinapic Acid in an Isolated Heart Model of Ischemia Reperfusion in Rats Here, we evaluated whether a cationic antioxidant devoid of any lipid affinity such as sinapine can protect the whole heart following an ischemic stress. We used the standard global ischemia-reperfusion model in the perfused isolated heart (FIG. 8). The contractile performances of the heart are evaluated by measuring the pressure developed within the left ventricle. The pressure developed (Pdev) is an index of the force developed during a contraction i.e. blood expulsion phase. The maximal and minimal first derivative of left intraventricular pressure ($dP/dt_{max}$ and $dP/dt_{min}$, respectively) give a dynamic information of the contraction and relaxation phases. In this model, accumulation of mitochondrial ROS are a key trigger of cardiac injuries and dysfunctions (Ambrosio et al., Reperfusion injury: Experimental evidence and clinical implications. Am. Heart J. 1999, 138. S69-75; Turrens et al. Mitochondrial generation of oxygen radicals during reoxygenation of ischemic tissues. Free Rad. Res. Com. 1991, 13, 681-689; Bulteau et al., Oxidative modification and inactivation of the proteasome during coronary occlusion/reperfusion. J. Biol. Chem. 2001, 276, 30057-30063). The potential cardioprotective effect of 60 μM sinapine was compared to 60 μM sinapic acid and to a known synthetic mitochondrial ROS scavenger, mito-TEMPO (MitoT, 0.1 μM) (Olgar et al. Aging related functional and structural changes in the heart and aorta: Mito-TEMPO improves aged-cardiovascular performance. Exp. Gerontol. 2018, 110, 172-181).

Importantly, this latter cationic antioxidant has a significant lipid affinity (50% of partition in octan-1-ol; experimental log D (pH 7.0)=0.0), while sinapine is a cationic antioxidant devoid of any lipid affinity (<0.2% of partition in octan-1-ol; experimental log D (pH 7.0)=−3.0 (FIG. 2).

No major modification was observed during the ischemic phase with the different compounds. Classically, after 10 min reperfusion, the heart does not fully recover when compared with the baseline level. This is illustrated by recovery of only 30% approx. of the Pdev, $dP/dt_{max}$ and $dP/dt_{min}$ in control hearts. The levels of recovery of Pdev and $dP/dt_{max}$ increased significantly to 44-50% in presence of MitoT, but the relaxation phase, $dP/dt_{min}$ was not affected by MitoT.

Interestingly, the cardioprotective effect of sinapine was larger with a recovery by 60-70% of all parameters (Pdev, $dP/dt_{max}$, and $dP/dt_{min}$) (FIG. 8B-D). Treatment with sinapic acid had no effect on any recovery parameter.

Figure 8E:
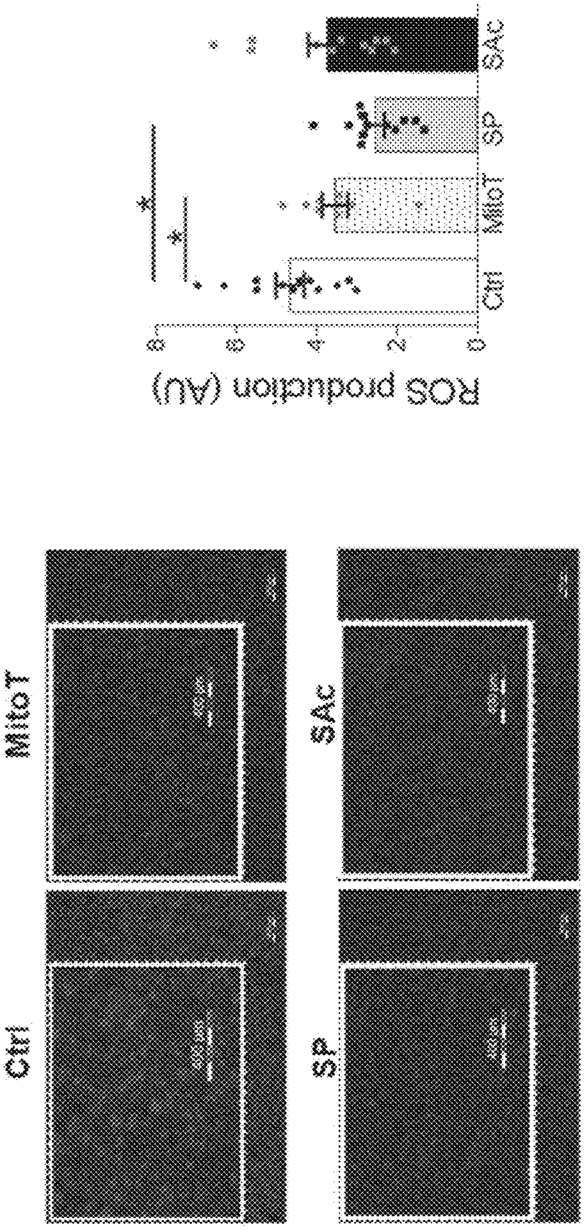
FIG. 8. Effect of sinapine and sinapic acid on cardiac functions following ischemia-reperfusion (IR) stress. (A) Examples of LV pressure during the ischemia-reperfusion protocol of the isolated heart perfused retrogradely using a Langendorff apparatus. Hearts were stabilized for 20 min and then perfused for 45 min with or without sinapic acid (60 μM), sinapine (60 μM) or MitoTempo (MitoT). Hearts were subjected to global no-flow ischemia for 20 min followed by 10 min of reperfusion. (B-D) Recovery of the developed pressure (Pdev), the maximal and minimal first derivative of left intraventricular pressure (dP/dtmax and dP/dtmin, respectively) 10 min post-IR. Values are normalized to the baseline level. (E) Determination of ROS production by dihydroethidium (DHE) staining 10 min after IR, in hearts pre-treated or not with MitoT (0.1 μM), sinapine (SP, 60 μM), or sinapic acid (SAc, 60 μM). Scale bar=400 μm, (n=12 control hearts, n=9 MitoT hearts, n=12 sinapine hearts, n=11 sinapic acid heart). * p<0.05.

Those functional results were influenced by the level of ROS produced in the tissue after ischemia-reperfusion, measured by dihydroethidium (DHE) staining on cardiac tissue (FIG. 8E). We observed that MitoT reduced significantly DHE fluorescence compared to control tissue by 24% indicating lower ROS production during reperfusion. Hearts pre-treated with sinapine produced even less ROS since DHE staining was reduced by 45% compared with control hearts. For sinapic acid pre-treated hearts, a modest tendency of reduced ROS production (−20% versus Ctrl) was observed but did not reach significance (p=0.12).

Altogether, the results indicate that targeting mitochondrial ROS is a cardioprotective strategy that can be achieved using a cationic antioxidant devoid of any lipid affinity such as sinapine, but not sinapic acid lacking the positively charged group.

Figure 9:
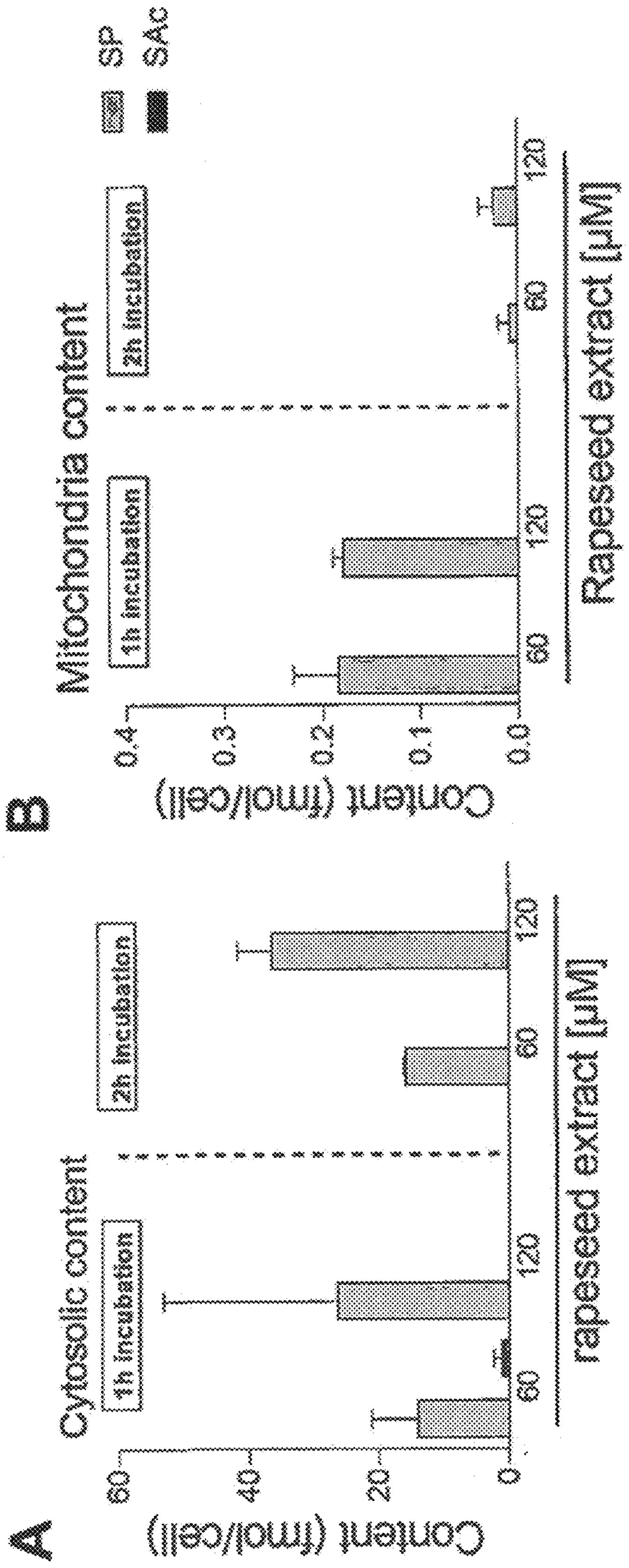
FIG. 9. Quantification of sinapine and sinapic acid entry in the cardiomyocytes incubated with rapeseed meal extract by HPLC. Myocytes were incubated for 1 or 2 h with different concentrations of natural rapeseed meal extract containing 4% wt of sinapine. After fractional separation, the amounts of sinapine (grey) and sinapic acid (black) were measured by LC-MS/MS in the cytosol (A) or in isolated mitochondria (B). (n=3 experiments with extracts).

Example 8. Subcellular Partitioning of a Rapeseed Meal Extract (Containing 4% Sinapine) in Rat Cardiomyocytes In this Example, we evaluated whether sinapine contained in a natural extract of rapeseed meal (obtained using a 30/70% hydroethanolic solution) can enter, similarly as pure sinapine, into both cytosol and mitochondria of freshly isolated adult cardiomyocytes (FIG. 9). We incubated the extracts in intact cardiomyocytes to reach two sinapine final concentrations (60 and 120 μM) for 1 or 2 h. Then, the mitochondrial fraction was separated from the cytosolic one using differential centrifugation as in Example 4. The levels of sinapine and sinapic acid were measured in each subcellular fraction using LC-MS/MS.

In cytosol, after one or two hours of rapeseed meal extract incubation, we detected sinapine in a dose dependent manner (FIG. 9A), while sinapic acid was not detected in substantial amounts, indicating no major sinapine hydrolysis. No time-dependency of the incubation was found on cellular levels of sinapine suggesting, similarly as for the pure sinapine, that, when present in a natural extract at low dosage, sinapine entry into cardiac cells is a rapid process taking place within an hour.

We also evaluated mitochondrial subfractions (FIG. 9B). After the extract containing sinapine was incubated for 1 h, sinapine was detected in mitochondria around 0.2 femtomol/cell. For two hours, the recovered amount of sinapine found in mitochondria significantly decreased below 0.05 femtomol/cell.

Example 9. Beneficial Effect of a Rapeseed Meal Extract Containing 4% (Wt) Sinapine In Vivo on Cardiac Contractile Function in Rats In this Example, it is shown that a rapeseed meal extract containing 4% (wt) of a cationic antioxidant with no lipid affinity (sinapine) had beneficial effects on cardiac contractile function after an exhausting exercise and during recovery.

Figure 10A:
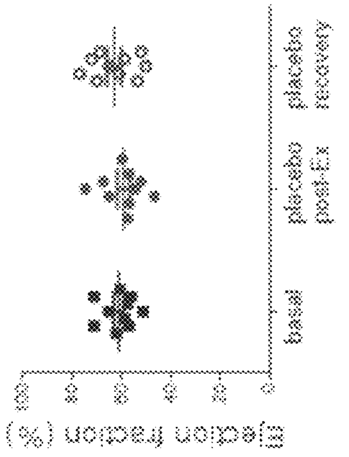
FIG. 10. Effects of rapeseed meal extract on the cardiovascular consequences of intense and prolonged exercise; in vivo cardiac contractile analysis. (n=10 animals/group. *=p<0.05. Kruskal Wallis test.)
Figure 10B:
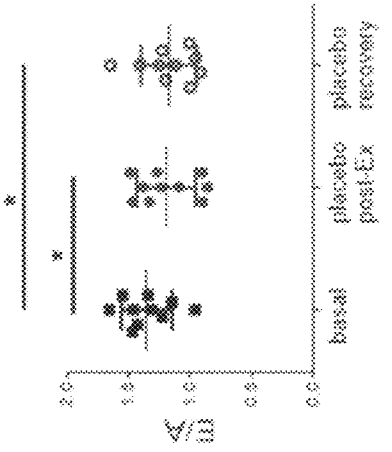
Figure 10C:
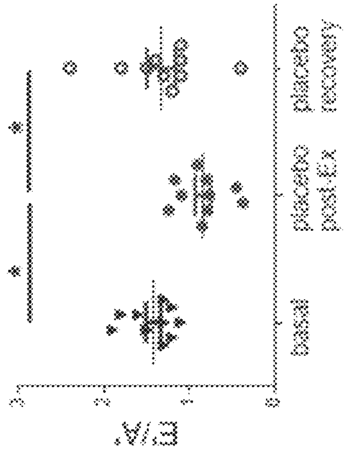
Figure 10F:
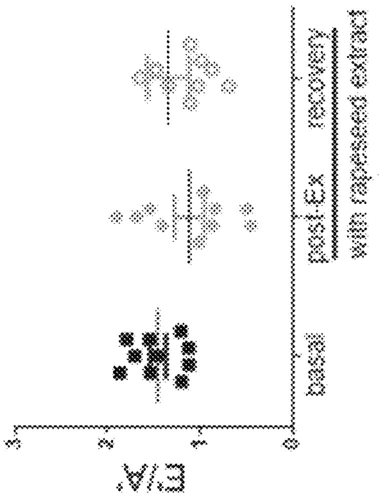
Figure 10E:
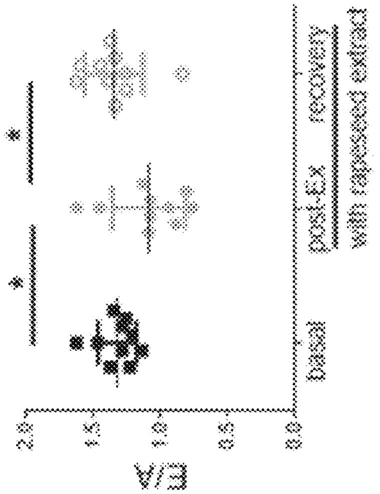
Figure 10D:
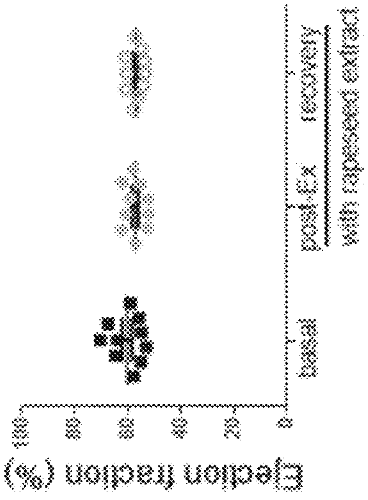

Cardiac contractile function was evaluated in vivo by echocardiography a week before exercise (basal), 30-min after exhausting exercise (post-Ex) and a week after exercise (recovery) in placebo animals (FIG. 10A-C) and animals orally treated with rapeseed meal extract 24 and 1 h before exercise. Systolic function of the left ventricle (LV), which is the phase of blood expulsion and which is indexed by ejection fraction parameter, was not altered in placebo (FIG. 10A) and extract treated animals (FIG. 10D). The diastolic function, i.e. relaxation phase of the LV, was indexed by two parameters: the E/A (FIG. 10B, E) and the E'/A' (FIG. 10C, F). For E/A, we measured the amount of blood inflow through the mitral valve during the filling phase of the ventricle and calculate the velocities of the blood inflow during the early filling phase (E wave) and late diastolic filling (A wave). For E'/A', we measured the movement of the myocardium close to the mitral valve during the filling phase of the ventricle and calculated the velocities of the myocardial displacement during the early filling phase (E' wave) and late diastolic filling (A' wave).

In placebo animals. E/A decreases by 12% after exercise due to 26% increase of A wave (active atrial filling). The E'/A' ratio decreases by 38% due to 61% increase of A'. After a week of recovery, E/A is decreased by 12% (due to 28% A wave increase). The EVA' ratio is normal due to E' wave increase by 37%.

In rapeseed treated animals, the E/A ratio decreases by 17% after exercise and is normal after recovery. The E'/A' was normal in all conditions.

Altogether, these results indicate that rapeseed meal extract containing 4% (wt) of a cationic antioxidant with no lipid affinity (sinapine) had cardioprotective effect on the exercise-induced diastolic dysfunction. The beneficial effect of rapeseed meal extract on the properties of relaxation of the heart is of importance for cardiac pathologies such as heart failure with preserved ejection fraction (HFpEF) that is a typical disease of cardiac relaxation and the classical ischemic or congenital heart failure with reduced ejection fraction (HFrEF) in which cardiac relaxation is altered in association with the systolic properties. Altering cardiac relaxation impacts the pump function of the heart and its capacity to fill properly the blood.

Figure 11A:
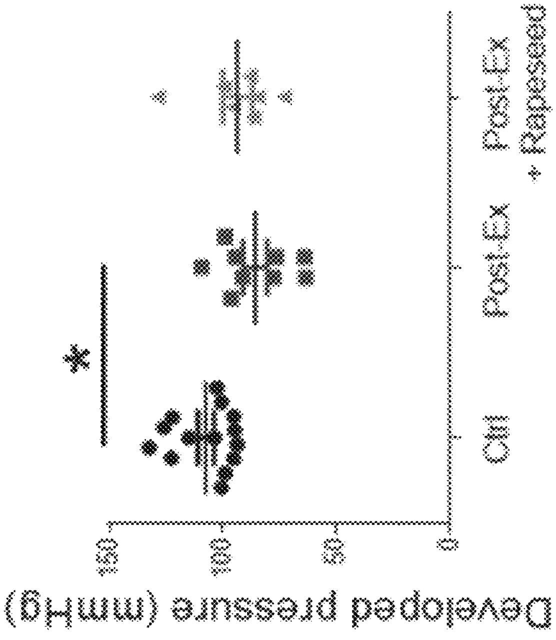
FIG. 11. Effects of rapeseed meal extract on the cardiovascular consequences of intense and prolonged exercise; ex vivo cardiac contractile analysis. (n=10 animals/group. *=p<0.05. ANOVA following by Bonferoni post-hoc test.)
Figure 11B:
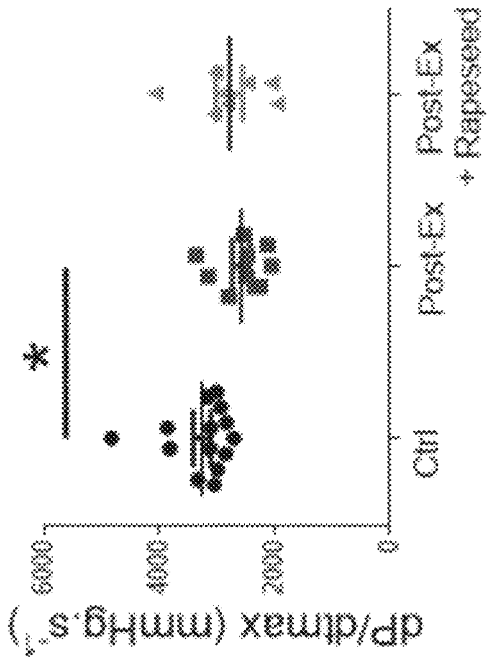
Figure 11C:
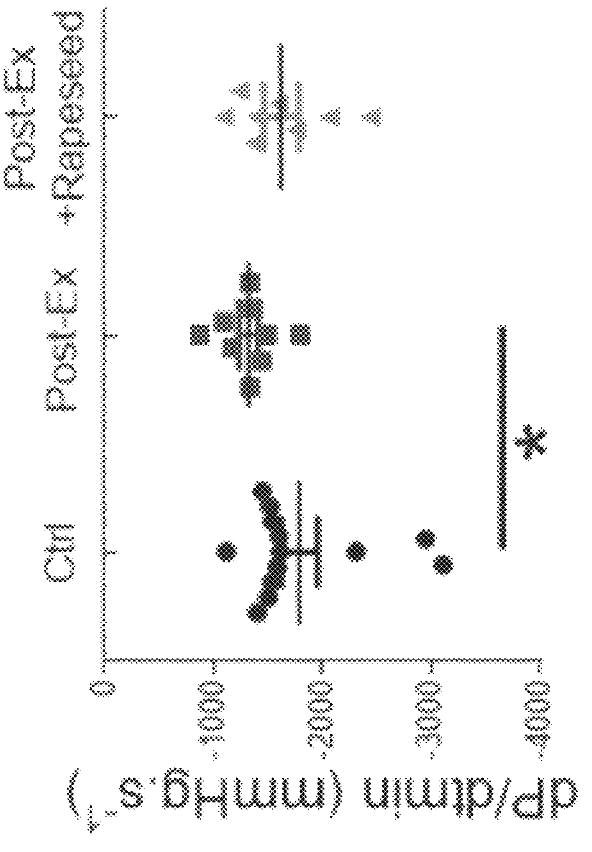

Example 10. Beneficial Effect of a Rapeseed Meal Extract Containing 4% (Wt) Sinapine Ex Vivo on Cardiac Contractile Function in Rats Cardiac contractile function was evaluated ex vivo on an isolated Langendorff system in the heart of sedentary animals (Ctrl), or 30 min after an exhausting exercise in animals orally treated with a placebo (Post-Ex) or a rapeseed meal extract (Post-Ex+ Rapeseed) 24 and 1 h before exercise. Systolic function of the left ventricle (LV) was indexed by (i) the developed pressure corresponding to the phase of contraction of the heart and blood ejection (FIG. 11A) and (ii) the maximal first derivative pressure (dP/dtmax) corresponding to the velocity at which the heart contracts (FIG. 11B). The diastolic function, i.e. relaxation of the LV, was indexed by the minimal first derivative pressure (dP/dtmin) corresponding to the velocity at which the heart relaxes (FIG. 11C).

An exhaustive exercise decreases the developed pressure (−20%) as well as maximal (−21%) and minimal (−26%) first derivative pressure in Post-Ex hearts compared to control (Ctrl) sedentary hearts. Interestingly, a rapeseed meal extract treatment prevented some of those functional modifications with a much lower reduction of developed pressure (−13%) as well as maximal (−14%) and minimal (−9%) first derivative pressure compared to control (Ctrl) sedentary hearts. The differences between rapeseed meal extract pre-treated hearts post-Ex and Ctrl sedentary hearts disappeared statistically. This shows that a pre-treatment with a natural extract containing a low level of a cationic antioxidant with no lipid affinity (sinapine) could limit the deleterious effects of prolonged exhaustive exercise on cardiac function analyzed ex vivo.

Example 11. Antiarrhythmic Effect in Rats of a Rapeseed Meal Extract Containing 4% (Wt) of Sinapine Here, we show that a rapeseed meal extract (obtained using a 30/70% hydroethanolic solution) containing 4% (wt) of a cationic antioxidant with no lipid affinity (sinapine) had beneficial effects on rhythmic cardiac function after exercise and during recovery evaluated by telemetry electrocardiogram (ECG). Rhythmic cardiac function was evaluated in vivo during 30 min a week before exercise (basal), following exhausting exercise (post-Ex) and a week after exercise (recovery) in placebo animals (red squares) and animals treated orally with a rapeseed meal extract before exercise (green triangles) by telemetry electrocardiogram.

While the number of arrhythmias increased after exercise in placebo animals, no detectable arrhythmias was observed in rapeseed animals, thus demonstrating the antiarrhythmic potential of an extract containing a low level (4%) of a cationic antioxidant with no lipid affinity (FIG. 12A).

We then investigated the RR interval, which is the average duration between two heart beats, index of heart rate frequency (FIG. 12, insert). The higher the RR interval, the lower the heart rate frequency (bradycardia), the better the cardiac performances. The RR interval is decreased after exercise (−23%) suggesting a tachycardia mostly due to the activation of sympathetic nervous system during exercise and recover after a week (+8%) in placebo animals (FIG. 12B) In rapeseed treated animals, RR interval decreased after exercise (−24%) and increased after a week (+10%) compared to basal condition. Here, the recovery with a rapeseed treatment allows to significantly improve the RR interval, which is not the case in the placebo group.

Figure 12C:
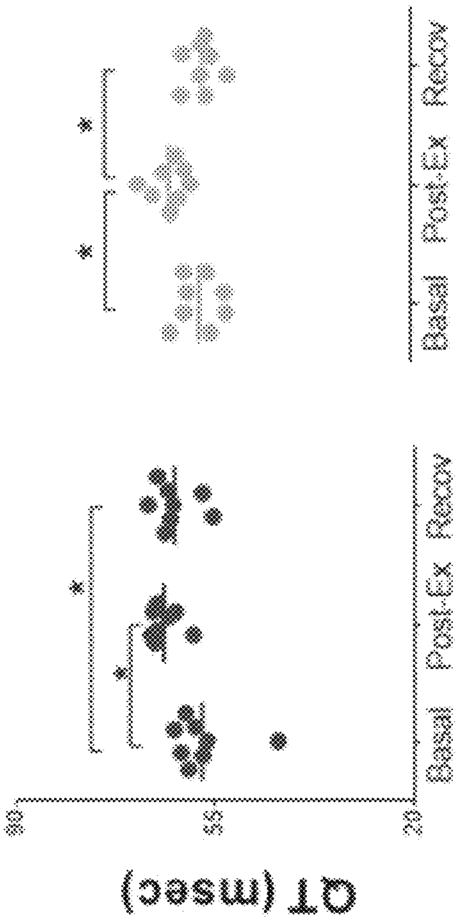
FIG. 12. Effects of rapeseed meal extract on the cardiovascular consequences of intense and prolonged exercise; in vivo cardiac rhythm analysis. (A) Comparison of the total number of arrhythmias. (B) Comparison of sinusal rhythm indexed by RR interval. (C) Depolarization and repolarization ventricular time indexed by QT segment. (n=10 animals/group. *=p<0.05. Kruskal Wallis test.)

The last parameter we studied in this Example was the QT segment which is the time for both ventricular depolarization and repolarization; it roughly estimates the duration of an average ventricular action potential. The QT interval on the ECG has gained clinical importance, primarily because prolongation of this interval can predispose to a potentially fatal ventricular arrhythmia known as "torsades de pointes". It is increased after exercise (+8%) and did not recover after a week (+10%) in placebo animals compared with basal conditions (FIG. 12C). In contrast, QT segment is increased after exercise (+9%) and recovered after a week (+1%) compared to basal condition in rapeseed treated animals. Treatment with a cationic antioxidant with no lipid affinity targeting mitochondria can thus be beneficial in this case. Indeed, in long QT syndrome, the heart muscle takes longer than normal to recharge between beats which can lead to chaotic heartbeats, fainting, seizures, and sudden death.

Altogether, the results indicate that rapeseed meal extract had cardioprotective effect on the exercise-induced rhythmic dysfunction particularly during recovery.

Example 12. Beneficial Effect of a Rapeseed Meal Extract Containing 4% (Wt) Sinapine on Recovery of the Skeletal Muscular Force in Rats (Ex Vivo)

Muscular function was evaluated ex vivo in sedentary-animals (Ctrl, open symbol), or a week after an exhausting exercise (recovery) in placebo animals (square symbol) and animals orally treated with a rapeseed meal extract (4% sinapine) before exercise (diamond symbol, dash line) in Extensor digitorum longus (EDL) and soleus isolated muscles. The body is composed of two skeletal muscle types depending of their function. The slow muscle type such as the Soleus have usually high capacities to resist to long physical effort (jogging, bicycle, etc.). The fast muscle type such as the EDL is involved in fast contractions (jump) and has usually low capacities to resist to long physical effort. They have thus different functional properties and responses to stress.

Figure 13:
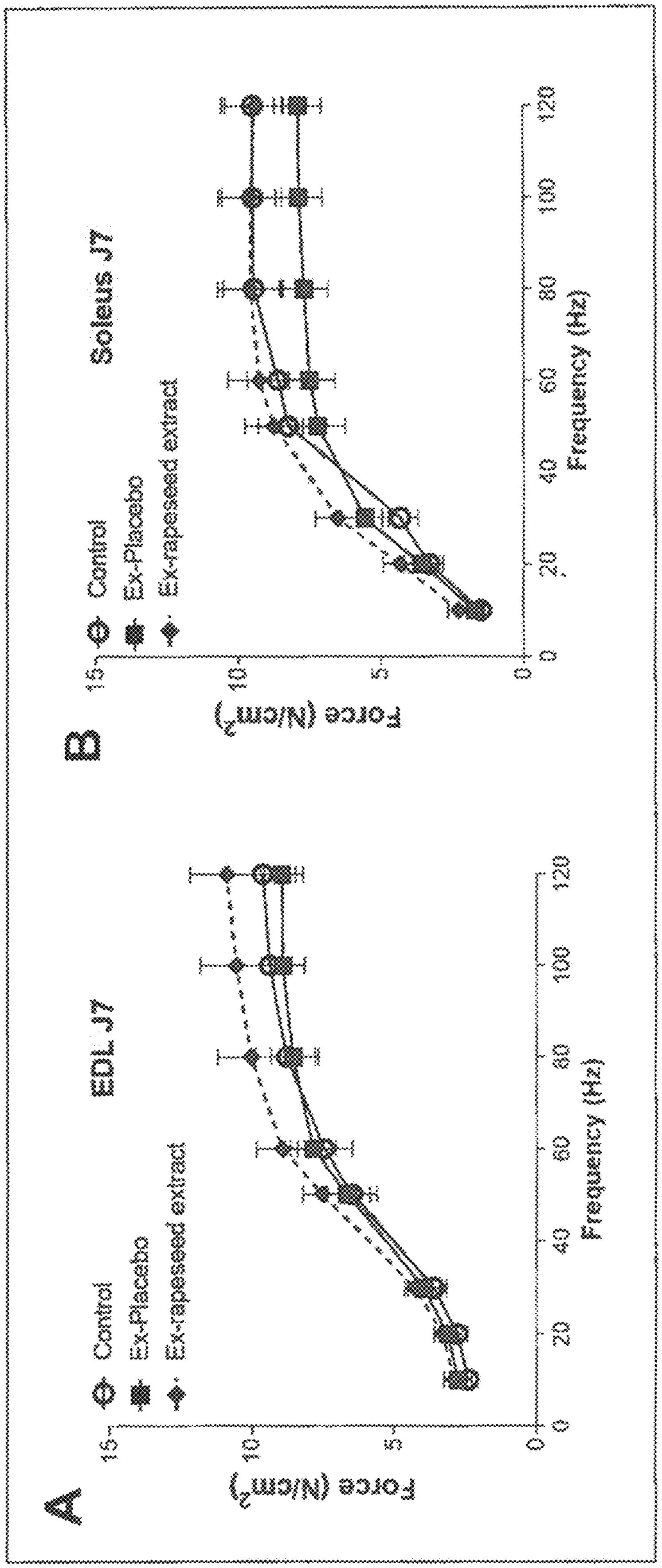
FIG. 13. Recovery effects of a rapeseed meal extract on the muscular force in EDL (left panel) and soleus (right panel) a week after an intense and prolonged exercise; ex vivo skeletal contractile analysis. (n=10 animals/group. *=p<0.05. Kruskal Wallis test.)

FIG. 13 shows that the rapeseed meal extract improved recovery of force in both EDL (left panel) and soleus (right panel). Therefore, a natural extract containing a low level of a cationic antioxidant with no lipid affinity (sinapine) exerts beneficial effects on muscular function during recovery.

Example 13. Beneficial Effect of a Rapeseed Meal Extract Containing 4% (Wt) Sinapine on Skeletal Contractile Fatigability in Rats (Ex Vivo)

Figure 14:
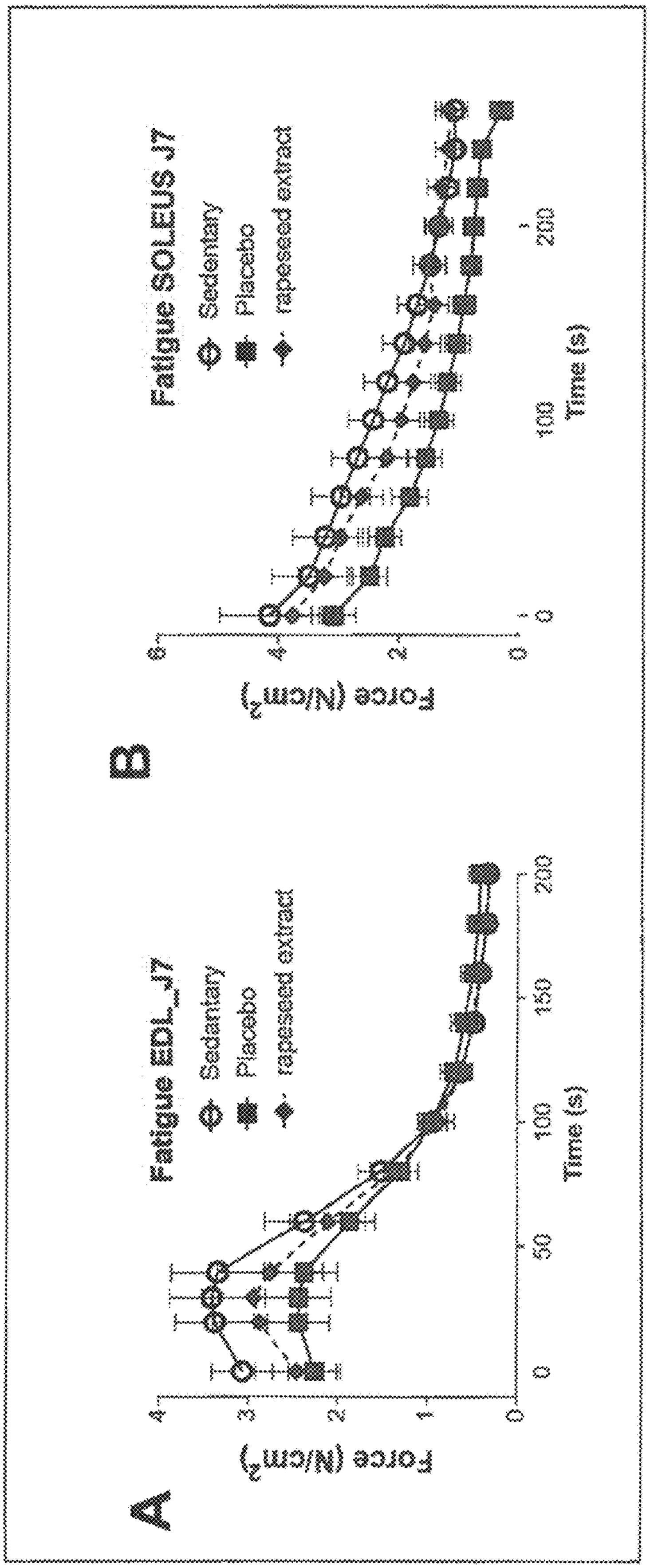
FIG. 14. Recovery effects of a rapeseed meal extract on the skeletal contractile fatigability in EDL (left panel) and soleus (right panel) a week after an intense and prolonged exercise (ex vivo). (n=10 animals/group. *=p<0.05. Kruskal Wallis test.

The fatigability of the muscle was evaluated ex vivo in control sedentary animals (Ctrl, open circle), or a week after and intense and prolonged exercise (recovery) in placebo animals (square symbol) and animals orally treated with a rapeseed meal extract before exercise (diamond symbol, dash line) in EDL (left panel) and soleus (right panel) isolated muscles. FIG. 14 shows that the recovery of muscle resistance to repeated effort was incomplete after 7 days in placebo animals for EDL (−30 to −40%) and soleus (−20 to −50%) muscle.

In contrast, the rapeseed meal extract improved recovery of force resistance in both EDL and soleus showing that a natural extract containing a low level of a cationic and hydrophilic antioxidant (sinapine) has beneficial effects on skeletal contractile fatigability during recovery.

Various illustrative embodiments of the disclosure include the following:

According to a first illustrative embodiment, disclosed is a compound having a lipid affinity of less than 15% is used in reducing, inhibiting or preventing the formation of mitochondrial reactive oxygen species.

According to a second illustrative embodiment, disclosed is a compound having a lipid affinity of less than 15%, is used in treating or preventing a pathological condition associated with increased levels of mitochondrial reactive oxygen species.

According to a third illustrative embodiment, disclosed is a method of reducing, inhibiting or preventing the formation of mitochondrial reactive oxygen species comprising the administration of a therapeutically effective amount of a compound having a lipid affinity of less than 15% to a subject in need thereof.

According to a fourth illustrative embodiment, disclosed is a method of treating or preventing a pathological condition associated with increased levels of mitochondrial reactive oxygen species comprising the administration of a therapeutically effective amount of compound having a lipid affinity of less than 15% to a subject in need thereof.

According to a fifth illustrative embodiment, disclosed is a use of a compound having a lipid affinity of less than 15% in the manufacture of a medicament for reducing, inhibiting or preventing the formation of mitochondrial reactive oxygen species.

According to a sixth illustrative embodiment, disclosed is a use of a compound having a lipid affinity of less than 15% in the manufacture of a medicament for treating or preventing a pathological condition associated with increased levels of mitochondrial reactive oxygen species.

According to a seventh illustrative embodiment, disclosed is a compound for use according to the second illustrative embodiment, or the method according to the fourth illustrative embodiment, or the use according to the sixth illustrative embodiment, wherein the pathological condition associated with increased levels of mitochondrial reactive oxygen species is selected from cancer, ischemic reperfusion injury, heart failure, peripheral artery diseases, hyperglycemia, diabetes, insulin resistance, neurodegenerative diseases, chronic obstructive pulmonary diseases, hypertension and inflammatory diseases.

According to an eighth illustrative embodiment, disclosed is a method of enhancing sports performance, comprising the administration of an effective amount of a compound having a lipid affinity of less than 15% to a subject in need thereof to reduce, inhibit or prevent the formation of mitochondrial reactive oxygen species.

According to a ninth illustrative embodiment, disclosed is a method of reducing, inhibiting or preventing the formation of mitochondrial reactive oxygen species during and/or after exercise comprising the administration of an effective amount of a compound having a lipid affinity of less than 15% to a subject in need thereof.

According to a tenth illustrative embodiment, disclosed is a method of enhancing muscle recovery during and/or after exercise comprising the administration of an effective amount of a compound having a lipid affinity of less than 15% to a subject in need thereof.

According to an eleventh illustrative embodiment, disclosed is a compound for use according to the first, second, or seventh illustrative embodiments, or the method according to the third, fourth, or seventh through tenth illustrative embodiments, or the use according to the fifth through seventh illustrative embodiments, (I)

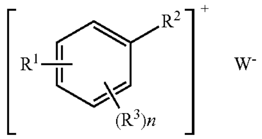

wherein the compound is of formula (I), or a pharmaceutically acceptable salt, derivative or salt of a derivative thereof, wherein, R1 is-OH, R2 is a cationic moiety, W— is a counterion, and each R3 is independently H or OR4, wherein R4 is H or C1-8 alkyl and n is 0 to 4.

According to a twelfth illustrative embodiment, disclosed is a compound for use according to the first, second, seventh, or eleventh illustrative embodiments, or a method according to the third, fourth, or seventh through eleventh illustrative embodiments, or the use according to the fifth through seventh or eleventh illustrative embodiments, wherein the compound is in the form of an extract obtained or obtainable from a plant of the Brassicaceae family.

According to a thirteenth illustrative embodiment, disclosed is a nutraceutical formulation, a dietary or food product for humans or animals, a nutritional supplement, a sports supplement, a fragrance or flavouring, a pharmaceutical or veterinary formulation, an oenological or cosmetic formulation consisting of, consisting essentially of or comprising a compound having a lipid affinity of less than 15%, a compound of formula (I) or an extract obtained or obtainable from a plant of the Brassicaceae family.

According to a fourteenth illustrative embodiment, disclosed is a nutraceutical formulation, a dietary or food product for humans or animals, a nutritional supplement, a sports supplement, a fragrance or flavouring, a pharmaceutical or veterinary formulation, an oenological or cosmetic formulation according to the thirteenth illustrative embodiment, wherein the nutraceutical formulation, a dietary or food product for humans or animals, a nutritional supplement, a sports supplement, a fragrance or flavouring, a pharmaceutical or veterinary formulation, an oenological or cosmetic formulation comprises the compound having a lipid affinity of less than 15%, the compound of formula (I) or extract obtained from or obtainable from a plant of the Brassicaceae family in an amount from about 0.5% by weight to about 100% by weight.

According to a fifteenth illustrative embodiment, disclosed is a nutraceutical formulation, a dietary or food product for humans or animals, a nutritional supplement, a sports supplement, a fragrance or flavouring, a pharmaceutical or veterinary formulation, an oenological or cosmetic formulation as defined in the thirteenth or fourteenth illustrative embodiments, further comprising a pharmaceutically or veterinary acceptable excipient or carrier or (functional) food acceptable ingredient.

According to a sixteenth illustrative embodiment, disclosed is a nutraceutical formulation, a dietary or food product for humans or animals, a nutritional supplement, a sports supplement, a fragrance or flavouring, a pharmaceutical or veterinary formulation, an oenological or cosmetic formulation as defined in the thirteenth or fourteenth illustrative embodiments, for use in reducing, inhibiting or preventing the formation of mitochondrial reactive oxygen species.

According to a seventeenth illustrative embodiment, disclosed is a method of reducing, inhibiting or preventing the formation of mitochondrial reactive oxygen species comprising the administration of a therapeutically effective amount of a nutraceutical formulation, a dietary or food product for humans or animals, a nutritional supplement, a sports supplement, a fragrance or flavouring, a pharmaceutical or veterinary formulation, an oenological or cosmetic formulation as defined in the thirteenth or fourteenth illustrative embodiments, to a subject in need thereof.

According to an eighteenth illustrative embodiment, disclosed is a use of a nutraceutical formulation, a dietary or food product for humans or animals, a nutritional supplement, a sports supplement, a fragrance or flavouring, a pharmaceutical or veterinary formulation, an oenological or cosmetic formulation as defined in the thirteenth or fourteenth illustrative embodiments in the manufacture of a medicament for reducing, inhibiting or preventing the formation of mitochondrial reactive oxygen species.

According to a nineteenth illustrative embodiment, disclosed is a nutraceutical formulation, a dietary or food product for humans or animals, a nutritional supplement, a sports supplement, a fragrance or flavouring, a pharmaceutical or veterinary formulation, an oenological or cosmetic formulation as defined in the thirteenth or fourteenth illustrative embodiments for use in treating or preventing a pathological condition associated with increased levels of mitochondrial reactive oxygen species.

According to a twentieth illustrative embodiment, disclosed is a method of treating or preventing a pathological condition associated with increased levels of mitochondrial reactive oxygen species comprising the administration of nutraceutical formulation, a dietary or food product for humans or animals, a nutritional supplement, a sports supplement, a fragrance or flavouring, a pharmaceutical or veterinary formulation, an oenological or cosmetic formulation as defined in the thirteenth or fourteenth illustrative embodiments to a subject in need thereof.

According to a twenty-first illustrative embodiment, disclosed is the use of nutraceutical formulation, a dietary or food product for humans or animals, a nutritional supplement, a sports supplement, a fragrance or flavouring, a pharmaceutical or veterinary formulation, an oenological or cosmetic formulation as defined in the thirteenth or fourteenth illustrative embodiments in the manufacture of a medicament treating or preventing a pathological condition associated with increased levels of mitochondrial reactive oxygen species.

According to a twenty-second illustrative embodiment, disclosed is the use or method according to the twentieth or twenty-first illustrative embodiments, wherein the pathological condition associated with increased levels of mitochondrial reactive oxygen species is selected from cancer, ischemic reperfusion injury, heart failure, peripheral artery diseases, hyperglycemia, diabetes, insulin resistance, neurodegenerative diseases, chronic obstructive pulmonary diseases, hypertension and inflammatory diseases.

According to a twenty-third illustrative embodiment, disclosed is a method of enhancing sports performance, comprising the administration of an effective amount of a nutraceutical formulation, a dietary or food product for humans or animals, a nutritional supplement, a sports supplement, a fragrance or flavouring, a pharmaceutical or veterinary formulation, an oenological or cosmetic formulation as defined in the thirteenth or fourteenth illustrative embodiments to a subject in need thereof to reduce, inhibit or prevent the formation of mitochondrial reactive oxygen species.

According to a twenty-fourth illustrative embodiment, disclosed is a method of reducing, inhibiting or preventing the formation of mitochondrial reactive oxygen species during exercise comprising the administration of an effective amount of a nutraceutical formulation, a dietary or food product for humans or animals, a nutritional supplement, a sports supplement, a fragrance or flavouring, a pharmaceutical or veterinary formulation, an oenological or cosmetic formulation as defined in the thirteenth or fourteenth illustrative embodiments to a subject in need thereof.

According to a twenty-fifth illustrative embodiment, disclosed is a method of enhancing muscle recovery during and/or after exercise comprising the administration of an effective amount of a nutraceutical formulation, a dietary or food product for humans or animals, a nutritional supplement, a sports supplement, a fragrance or flavouring, a pharmaceutical or veterinary formulation, an oenological or cosmetic formulation as defined in the thirteenth or fourteenth illustrative embodiments to a subject in need thereof.

The invention claimed is:

1. A method of a enhancing sports performance, or b enhancing muscle recovery during and/or after exercise comprising administering to a subject in need thereof a therapeutically effective amount of compound comprising (I)

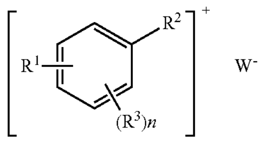

formula (I), or a pharmaceutically acceptable salt, derivative or salt of a derivative thereof, wherein, $R^1$ is —OH, $R^2$ is a cationic moiety, W is a counterion, and each $R^3$ is independently H or $OR^4$, wherein $R^4$ is H or $C_{1-8}$ alkyl and n is 0 to 4.

2. The method according to claim 1, wherein $R^2$ may be

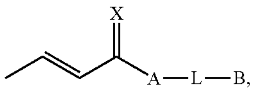

wherein X is O or S; A is O or NH; L is a linker group; and B is a cationic group.

3. The method according to claim 2, wherein the linker may be selected from a C1-8 alkylene or alkenylene group.

4. The method according to claim 2, wherein B may be a cationic quaternary ammonium group.

5. The method according to claim 1, wherein the compound of formula (I) is

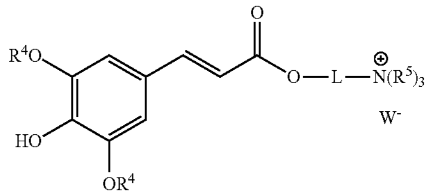

wherein each $R^5$ is independently selected from H or C1-8 alkyl group and wherein L is a linker group.

6. The method according to claim 1, wherein the compound of formula (I) is

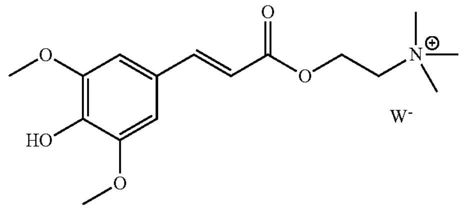

7. The method according to claim 1, wherein the compound is in the form of an extract obtained or obtainable from a plant of the Brassicaceae family.

8. The method according to claim 2, wherein the compound is in the form of an extract obtained or obtainable from a plant of the Brassicaceae family.

9. The method according to claim 1, wherein the compound of formula (I) is sinapine or a pharmaceutically acceptable salt, derivative or salt of a derivative thereof.

10. The method according to claim 7, wherein the compound of formula (I) is sinapine or a pharmaceutically acceptable salt, derivative or salt of a derivative thereof.

11. The method according to claim 8, wherein the compound of formula (I) is sinapine or a pharmaceutically acceptable salt, derivative or salt of a derivative thereof.

12. The method according to claim 1, wherein the compound having the formula (I) is provided in the form of a nutraceutical formulation, a dietary or food product for humans or animals, a nutritional supplement, a sports supplement, a fragrance or flavouring, a pharmaceutical or veterinary formulation, an oenological or cosmetic formulation.

13. The method according to claim 2, wherein the compound having the formula (I) is provided in the form of a nutraceutical formulation, a dietary or food product for humans or animals, a nutritional supplement, a sports supplement, a fragrance or flavouring, a pharmaceutical or veterinary formulation, an oenological or cosmetic formulation.

14. The method according to claim 7, wherein the compound having the formula (I) is provided in the form of a nutraceutical formulation, a dietary or food product for humans or animals, a nutritional supplement, a sports supplement, a fragrance or flavouring, a pharmaceutical or veterinary formulation, an oenological or cosmetic formulation.

15. The method according to claim 8, wherein the compound having the formula (I) is provided in the form of a nutraceutical formulation, a dietary or food product for humans or animals, a nutritional supplement, a sports supplement, a fragrance or flavouring, a pharmaceutical or veterinary formulation, an oenological or cosmetic formulation.

16. The method according to claim 12, wherein the nutraceutical formulation, a dietary or food product for humans or animals, a nutritional supplement, a sports supplement, a fragrance or flavouring, a pharmaceutical or veterinary formulation, an oenological or cosmetic formulation comprises compound of formula (I) or extract obtained from or obtainable from a plant of the Brassicaceae family in an amount from about 0.5% by weight to about 100% by weight.

17. The method according to claim 13, wherein the nutraceutical formulation, a dietary or food product for humans or animals, a nutritional supplement, a sports supplement, a fragrance or flavouring, a pharmaceutical or veterinary formulation, an oenological or cosmetic formulation comprises compound of formula (I) or extract obtained from or obtainable from a plant of the Brassicaceae family in an amount from about 0.5% by weight to about 100% by weight.

18. The method according to claim 14, wherein the nutraceutical formulation, a dietary or food product for humans or animals, a nutritional supplement, a sports supplement, a fragrance or flavouring, a pharmaceutical or veterinary formulation, an oenological or cosmetic formulation comprises compound of formula (I) or extract obtained from or obtainable from a plant of the Brassicaceae family in an amount from about 0.5% by weight to about 100% by weight.

19. The method according to claim 15, wherein the nutraceutical formulation, a dietary or food product for humans or animals, a nutritional supplement, a sports supplement, a fragrance or flavouring, a pharmaceutical or veterinary formulation, an oenological or cosmetic formulation comprises compound of formula (I) or extract obtained from or obtainable from a plant of the Brassicaceae family in an amount from about 0.5% by weight to about 100% by weight.

20. A method according to claim 12, wherein the dietary or food product for humans or animals, a nutritional supplement, a sports supplement, a fragrance or flavouring, a pharmaceutical or veterinary formulation, an oenological or cosmetic formulation further comprises a pharmaceutically or veterinary acceptable excipient or carrier or (functional) food acceptable ingredient.

21. The method according to claim 13, wherein the dietary or food product for humans or animals, a nutritional supplement, a sports supplement, a fragrance or flavouring, a pharmaceutical or veterinary formulation, an oenological or cosmetic formulation further comprises a pharmaceutically or veterinary acceptable excipient or carrier or (functional) food acceptable ingredient.

22. The method according to claim 14, wherein the dietary or food product for humans or animals, a nutritional supplement, a sports supplement, a fragrance or flavouring, a pharmaceutical or veterinary formulation, an oenological or cosmetic formulation further comprises a pharmaceutically or veterinary acceptable excipient or carrier or (functional) food acceptable ingredient.

23. The method according to claim 15, wherein the dietary or food product for humans or animals, a nutritional supplement, a sports supplement, a fragrance or flavouring, a pharmaceutical or veterinary formulation, an oenological or cosmetic formulation further comprises a pharmaceutically or veterinary acceptable excipient or carrier or (functional) food acceptable ingredient.

* * * * *